United States Patent [19]

Fujita et al.

[11] Patent Number: 5,688,823
[45] Date of Patent: Nov. 18, 1997

[54] THIAZOLIDINE AND OXAZOLIDINE DERIVATIVES THEIR PREPARATION AND THEIR MEDICAL USE

[75] Inventors: Takashi Fujita; Koichi Fujimoto; Takao Yoshioka; Hiroaki Yanagisawa; Toshihiko Fujiwara; Hiroyoshi Horikoshi; Minoru Oguchi; Kunio Wada, all of Tokyo, Japan

[73] Assignee: Sankyo Company, Limited, Tokyo, Japan

[21] Appl. No.: 604,702

[22] Filed: Feb. 21, 1996

Related U.S. Application Data

[62] Division of Ser. No. 410,033, Mar. 23, 1995, Pat. No. 5,578,620.

[30] Foreign Application Priority Data

Mar. 23, 1994 [JP] Japan .................................. 6-051541

[51] Int. Cl.$^6$ .................. A61K 31/42; C07D 263/44
[52] U.S. Cl. .................................. 514/376; 548/226
[58] Field of Search ........................... 548/226; 514/376

[56] References Cited

FOREIGN PATENT DOCUMENTS 9202520 2/1992 WIPO .

OTHER PUBLICATIONS

Cartello, J. Med. Chem. 37(23) 3977 (1994).

*Primary Examiner*—Robert Gerstl
*Attorney, Agent, or Firm*—Frishauf, Holtz, Goodman, Langer & Chick, P.C.

[57] ABSTRACT

Compounds of formula (I):

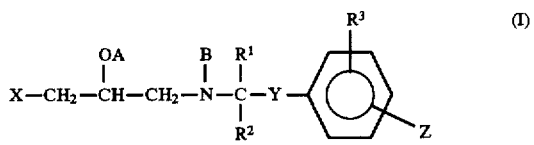

Z is a group of formula (iii), (iv),:

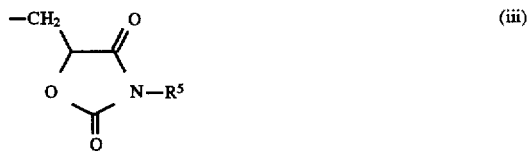

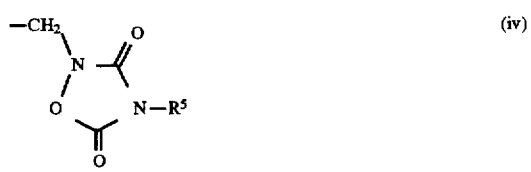

and salts, esters and solvates thereof and pro-drugs therefor are useful for the treatment and/or prophylaxis of a variety of disorders, including one or more of: hyperlipemia, hyperglycemia, obesity, glucose tolerance insufficiency, insulin resistance and diabetic complications.

31 Claims, No Drawings

THIAZOLIDINE AND OXAZOLIDINE DERIVATIVES THEIR PREPARATION AND THEIR MEDICAL USE

This is a division of application Ser. No. 08/410,033 filed Mar. 23, 1995 now U.S. Pat. No. 5,578,620.

BACKGROUND TO THE INVENTION

The present invention relates to a series of compounds which may be regarded as thiazolidine and oxazolidine derivatives. It also provides methods and compositions using these compounds, as well as processes for their preparation.

Compounds of this general type are disclosed in European Patent Publications No. 008 203, 139 421, 441 605, 208 420, 528 734, 177 353, 306 208 and 356 214, and in WO 92/07850, 92/07839, 91/07107, 92/02520 and 92/03425.

BRIEF SUMMARY OF INVENTION

Thus, it is an object of the present invention to provide a series of new chemical compounds which may be regarded as thiazolidine and oxazolidine derivatives or as ring-opened derivatives thereof.

It is a further, and more specific, object of the invention to provide such compounds, at least some of which may be useful for the treatment and/or prophylaxis of a variety of disorders, including one or more of: hyperlipemia, hyperglycemia, obesity, glucose tolerance insufficiency, insulin resistance and diabetic complications.

Other objects and advantages of the present invention will become apparent as the description proceeds.

Thus, the present invention provides compounds of formula (I):

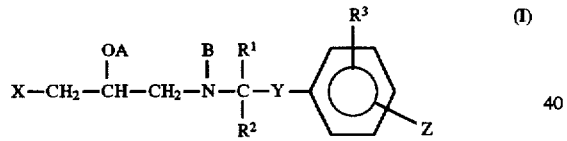

wherein:
- $R^1$ and $R^2$ are the same or different and each represents a hydrogen atom or an alkyl group having from 1 to 8 carbon atoms, or $R^1$ and $R^2$ together represent a group of formula —$(CH_2)_k$— (wherein k represents an integer of from 2 to 6);
- $R^3$ represents a hydrogen atom, an alkyl group having from 1 to 4 carbon atoms, an alkoxy group having from 1 to 4 carbon atoms, a halogen atom or a hydroxy group;
- A and B are the same or different and each represents a hydrogen atom, an alkyl group having from 1 to 8 carbon atoms, an aralkyl group in which an alkyl group having from 1 to 5 carbon atoms is substituted by an aryl group as defined below, an aliphatic carboxylic acyl group having from 1 to 11 carbon atoms, an aliphatic carboxylic acyl group which has from 2 to 6 carbon atoms and which is substituted by an aryl group as defined below, an aromatic carboxylic acyl group in which the aryl part is as defined below, a carbamoyl group of formula —$CONR^6R^7$,
  wherein $R^6$ and $R^7$ are the same or different and each represents a hydrogen atom, an alkyl group having from 1 to 11 carbon atoms, an aryl group as defined below or an aralkyl group in which an alkyl group having from 1 to 5 carbon atoms is substituted by an aryl group as defined below;
  or A and B together represent a group of formula >C=O, a group of formula >C=S, a group of formula —C(=O)—C(=O)—, a group of formula —$CH_2C$(=O)—, a group of formula —$CH_2CH_2$—, a group of formula —$SO_2$— or a group of formula —$CH_2SO_2$—;
- X represents a group of formula: W—$(CH_2)_m$—$X^1$—
  wherein W represents
    an aryl group as defined below,
    a heterocyclic group having 5 or 6 ring atoms of which from 1 to 3 are hetero-atoms selected from the group consisting of oxygen, sulfur and nitrogen hetero-atoms and being unsubstituted or being substituted by at least one substituent selected from the group consisting of substituents α as defined below or such a heterocyclic group which is fused to at least one ring system selected from the group consisting of carbocyclic and heterocyclic rings having 5 or 6 ring atoms and which is unsubstituted or is substituted by at least one substituent selected from the group consisting of substituents α as defined below,
  $X^1$ represents a single bond, an oxygen atom, a sulfur atom or a group of formula >$NR^4$
    wherein $R^4$ represents a hydrogen atom, an alkyl group having from 1 to 8 carbon atoms, an aralkyl group in which an alkyl group having from 1 to 5 carbon atoms is substituted by at least one aryl group as defined below or an aryl group as defined below, and
  m represents 0 or an integer of from 1 to 8;
- Y represents a group of formula: —$(CH_2)_n$—$Y^1$—
  wherein $Y^1$ represents a single bond, an oxygen atom or a sulfur atom, and g represents an integer of from 1 to 5;
- Z represents a group of formula (i), (ii), (iii), (iv), (v) or (vi):

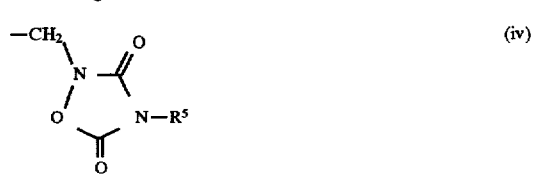

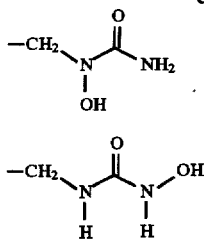

wherein R⁵ represents a hydrogen atom, a carboxyalkyl group having from 2 to 5 carbon atoms, an alkanoyloxyalkyl group having a total of from 2 to 12 carbon atoms, a cycloalkyl-substituted alkanoyloxyalkyl group having a total of from 6 to 12 carbon atoms, a cycloalkylcarbonyloxyalkyl group having a total of from 5 to 17 carbon atoms, an alkoxycarbonyloxyalkyl group having a total of from 3 to 17 carbon atoms, a cycloalkyl-substituted alkoxycarbonyloxyalkyl group having a total of from 6 to 17 carbon atoms or a cycloalkyloxycarbonyloxyalkyl group having a total of from 5 to 17 carbon atoms;

said aryl groups are carbocyclic aromatic groups which have from 6 to 14 ring carbon atoms and which are unsubstituted or are substituted by at least one substituent selected from the group consisting of substituents α, defined below; and said substituents α are selected from the group consisting of alkyl groups having from 1 to 4 carbon atoms, alkoxy groups having from 1 to 4 carbon atoms, haloalkyl groups having from 1 to 4 carbon atoms, hydroxy groups, halogen atoms, phenyl groups, nitro groups and groups of formula —NR$^a$R$^b$, wherein R$^a$ and R$^b$ are independently selected from the group consisting of hydrogen atoms, alkyl groups having from 1 to 8 carbon atoms, aralkyl groups in which an alkyl group having from 1 to 5 carbon atoms is substituted by an aryl group as defined above, aryl groups as defined above, aliphatic carboxylic acyl groups having from 1 to 11 carbon atoms, aliphatic carboxylic acyl groups which have from 2 to 6 carbon atoms and which are substituted by an aryl group as defined above, and aromatic carboxylic acyl groups in which the aryl part is as defined above, provided that any aryl group represented by or included in a group represented by R$^a$ or R$^b$ is not itself further substituted by a group of formula —NR$^a$R$^b$;

and salts, esters and solvates thereof and pro-drugs therefor.

The invention also provides a pharmaceutical composition for the treatment or prophylaxis of diabetes or hyperlipemia, which composition comprises an effective amount of an active compound in admixture with a pharmaceutically acceptable carrier or diluent, wherein said active compound is selected from the group consisting of compounds of formula (I), defined above, and salts, esters and solvates thereof and pro-drugs therefor.

The invention still further provides a method for the treatment or prophylaxis of diabetes or hyperlipemia in a mammal, which may be human, which method comprises administering to said mammal an effective amount of an active compound, wherein said active compound is selected from the group consisting of compounds of formula (I), defined above, and salts, esters and solvates thereof and pro-drugs therefor.

The invention also provides processes for the preparation of the compounds of the present invention, which processes are described in more detail hereafter.

DETAILED DESCRIPTION OF INVENTION

In the compounds of the present invention, where R¹ or R² represents an alkyl group, this may be a straight or branched chain alkyl group having from 1 to 8 carbon atoms, and examples include the methyl, ethyl, propyl, isopropyl, butyl, isobutyl, sec-butyl, t-butyl, pentyl, 2-pentyl, 3-pentyl, 2-methylbutyl, 3-methylbutyl, 1,1-dimethylpropyl, 1,2-dimethylpropyl, 2,2-dimethylpropyl, hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, heptyl, 2-heptyl, 3-heptyl, 4-heptyl, 3,3-dimethylpentyl, octyl, 1-methylheptyl, 2-ethylhexyl and 1,1,3,3-tetramethylbutyl groups. Preferred such alkyl groups are those straight and branched chain alkyl groups having from 1 to 6 carbon atoms, of which we prefer those groups having from 1 to 4 carbon atoms, and particularly the methyl and ethyl groups.

Alternatively, R¹ and R² may together represent a group of formula —(CH₂)$_k$—, wherein k represents an integer of from 2 to 6. Examples of such groups include the ethylene, trimethylene, tetramethylene, pentamethylene and hexamethylene groups, of which we prefer the trimethylene, tetramethylene and pentamethylene groups.

When R³ represents a straight or branched chain alkyl group, this may have from 1 to 4 carbon atoms, and examples of such alkyl groups include the methyl, ethyl, propyl, isopropyl, butyl, isobutyl, sec-butyl and t-butyl groups, of which we prefer the methyl group.

When R³ represents a straight or branched chain alkoxy group, this may have from 1 to 4 carbon atoms, and examples of such alkoxy groups include the methoxy, ethoxy, propoxy, isopropoxy, butoxy, isobutoxy, sec-butoxy and t-butoxy groups, of which we prefer the methoxy group.

When R³ represents a halogen atom, this may be, for example, a fluorine, chlorine, bromine or iodine atom, preferably a fluorine or chlorine atom.

When R³ represents a group or atom other than hydrogen, it can be at any position on the benzene ring, i.e. the o-, m- or p- position, relative to the position of attachment of the group represented by Y. Of these, the preferred position is the o- or m- position.

When A and/or B, which may be the same or different, each represents an alkyl group, this may be a straight or branched chain alkyl group having from 1 to 8 carbon atoms, and examples of such groups include the same alkyl groups as exemplified above in relation to R¹ and R².

When A and/or B represents an aralkyl group, this preferably has a total of from 7 to 11 carbon atoms, and is an alkyl group having from 1 to 5 carbon atoms which is substituted by an aryl group as defined above and exemplified below. Examples of the alkyl part of the group are those alkyl groups having from 1 to 5 carbon atoms which are included among the alkyl groups represented by R¹ (preferably the methyl and ethyl groups), and examples of the aryl part are included among those aryl groups listed hereafter in relation to W (preferably the phenyl and naphthyl groups, especially the phenyl group). Specific examples of preferred aralkyl groups include the benzyl, 2-phenylethyl (=phenethyl), 1-phenylethyl, 3-phenylpropyl, 2-phenylpropyl, 1-phenylpropyl, 4-phenylbutyl, 1-phenylbutyl, 5-phenylpentyl, 1-naphthylmethyl and 2-naphthylmethyl groups, of which the benzyl and phenethyl groups are preferred, the benzyl group being most preferred.

When A and/or B represents an aliphatic acyl group, this may be a straight or branched chain aliphatic acyl group having from 1 to 11 carbon atoms, and examples of such aliphatic acyl groups include the formyl, acetyl, propionyl, isopropionyl, butyryl, isobutyryl, pivaloyl, pentanoyl, hexanoyl, heptanoyl, octanoyl, nonanoyl, decanoyl and undecanoyl groups, of which the acetyl, propionyl, butyryl, isobutyryl and pivaloyl groups are preferred, the acetyl and pivaloyl groups being most preferred.

When A and/or B represents an aliphatic carboxylic acyl group which has from 2 to 6 carbon atoms and which is substituted by an aryl group as defined above, this preferably has a total of from 8 to 12 carbon atoms. Examples of the aliphatic acyl part of the group are those acyl groups having from 2 to 6 carbon atoms which are included among the aliphatic acyl groups represented by A above (preferably the acetyl and propionyl groups), and examples of the aryl part are included among those aryl groups listed hereafter in relation to W (preferably the phenyl and naphthyl groups, especially the phenyl group). Specific examples of preferred aromatic-substituted aliphatic acyl groups include the phenylacetyl, 3-phenylpropionyl, 4-phenylbutyryl, 5-phenylpentanoyl and 6-phenylhexanoyl groups, of which the phenylacetyl group is preferred.

When A and/or B represents an aromatic acyl group, the aryl group is as defined above, and examples of the aryl part are included among those aryl groups listed hereafter in relation to W (preferably the phenyl and naphthyl groups, especially the phenyl group). Preferred groups are those having a total of from 7 to 11 carbon atoms, and examples include the benzoyl, 1-naphthoyl and 2-naphthoyl groups, of which the benzoyl group is preferred.

When A and/or B represents a carbamoyl group, this may be an unsubstituted carbamoyl group or it may be a substituted carbamoyl group, preferably having from 2 to 12 carbon atoms in total. Such groups may be represented by the formula —CON$R^6$R$^7$, wherein $R^6$ and $R^7$ are the same or different and each represents a hydrogen atom, a straight or branched chain alkyl group having from 1 to 11 carbon atoms, an aralkyl group (for example as exemplified above in relation to A and B, and preferably having a total of from 7 to 11 carbon atoms) or an aryl group having from 6 to 10 ring carbon atoms. In the case where $R^6$ and $R^7$ are the same and both represent hydrogen atoms, the compound is an unsubstituted carbamoyl group.

Where $R^6$ and/or $R^7$ represents a straight or branched chain alkyl group having from 1 to 11 carbon atoms, this may be any of those alkyl groups exemplified above in relation to $R^1$ and $R^2$ and, in addition, the nonyl, decyl and undecyl groups. Of these groups, the methyl, ethyl and propyl groups are preferred, the methyl and ethyl groups being most preferred.

When $R^6$ and/or $R^7$ represents an aralkyl group, this may be as defined above and preferably has a total of from 7 to 11 carbon atoms. Examples of such aralkyl groups include those exemplified above in relation to A and B, preferably the benzyl and phenethyl groups most preferably the benzyl group.

When $R^6$ and/or $R^7$ represents an aryl group having from 6 to 10 carbon atoms, examples are included among those aryl groups listed hereafter in relation to W, particularly the phenyl, 1-naphthyl and 2-naphthyl groups, of which the phenyl group is most preferred.

Thus, the substituted carbamoyl groups are groups of the formula given above in which $R^6$ and $R^7$ comprise a combination of groups selected from those listed, and examples include:

1) a substituted carbamoyl group comprising a combination of a hydrogen atom and an alkyl group, such as the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, hexylcarbamoyl, heptylcarbamoyl, octylcarbamoyl, nonylcarbamoyl and decylcarbamoyl groups;

2) a substituted carbamoyl group comprising a combination of two alkyl groups, which may be the same or different, and preferably have from 1 to 4 carbon atoms, for example the dimethylcarbamoyl, N-methyl-N-ethylcarbamoyl, N-methyl-N-propylcarbamoyl, N-methyl-N-isopropylcarbamoyl, N-methyl-N-butylcarbamoyl, N-methyl-N-pentylcarbamoyl, N,N-diethylcarbamoyl, N-ethyl-N-propylcarbamoyl, N-ethyl-N-butylcarbamoyl, dipropylcarbamoyl, N-propyl-N-butylcarbamoyl and N,N-dibutylcarbamoyl groups;

3) a substituted carbamoyl group comprising a combination of a hydrogen atom and an aralkyl group, such as the benzylcarbamoyl, 2-phenylethylcarbamoyl, 1-phenylethylcarbamoyl, 3-phenylpropylcarbamoyl, 4-phenylbutylcarbamoyl, 5-phenylpentylcarbamoyl, 1-naphthylmethylcarbamoyl and 2-naphthylmethylcarbamoyl groups;

4) a substituted carbamoyl group comprising a combination of an alkyl group and an aralkyl group, such as the N-methyl-N-benzylcarbamoyl, N-ethyl-N-benzylcarbamoyl, N-propyl-N-benzylcarbamoyl, N-butyl-N-benzylcarbamoyl and N-methyl-N-(2-phenylethyl)carbamoyl groups;

5) a substituted carbamoyl group comprising a combination of an alkyl group and an aryl group, such as the N-methyl-N-phenylcarbamoyl, N-ethyl-N-phenylcarbamoyl, N-propyl-N-phenylcarbamoyl, N-butyl-N-phenylcarbamoyl, N-methyl-N-naphthylcarbamoyl and N-ethyl-N-naphthylcarbamoyl groups;

6) a substituted carbamoyl group comprising a combination of a hydrogen atom and an aryl group, such as the phenylcarbamoyl group;

7) a substituted carbamoyl group comprising a combination of two aryl groups, which may be the same or different, and are preferably the same, such as the diphenylcarbamoyl group.

When X represents a group of formula

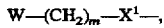

wherein m and W are as defined above, and $X^1$ represents a group of formula >NR$^4$ where $R^4$ represents a straight or branched chain alkyl group having from 1 to 8 carbon atoms, the alkyl group may be, for example, any of the same alkyl groups as exemplified above in relation to $R^1$ and $R^2$, preferably a methyl group.

When $R^4$ represents an aralkyl group, this may be as defined above and preferably has a total of from 7 to 11 carbon atoms. Examples of such aralkyl groups include those exemplified above in relation to A and B, preferably the benzyl and phenethyl groups, most preferably the benzyl group.

When $R^4$ represents an aryl group having from 6 to 10 carbon atoms, examples are included among those aryl groups listed hereafter in relation to W, particularly the phenyl, 1-naphthyl and 2-naphthyl groups, of which the phenyl group is most preferred.

When W represents an aryl group, this is a carbocyclic aryl group having from 6 to 10 ring carbon atoms and may be unsubstituted or may be substituted by at least one substituent selected from the group consisting of substituents α, defined above and exemplified below. Preferred examples of unsubstituted groups include the phenyl, 1-naphthyl and 2-naphthyl groups, of which the phenyl group is preferred. Although there is no restriction on the number of substituents except that imposed by the number of substitutable positions and possibly by steric constraints, we generally prefer from 1 to 5 substituents, more preferably from 1 to 3 substituents and most preferably 1 substituent. Examples of preferred substituted groups include the 2-, 3- and 4-chlorophenyl, 2-, 3- and 4-fluorophenyl, 2-, 3- and 4-bromophenyl, 2-, 3- and 4-methylphenyl, 2-, 3- and 4-ethylphenyl, 2-, 3- and 4-t-butylphenyl, 2-, 3- and 4-methoxyphenyl, 2-, 3- and 4-hydroxyphenyl, 2-, 3- and 4-phenylphenyl, 2-, 3- and 4-nitrophenyl, 2-, 3- and 4-aminophenyl, 2-, 3- and 4-methylaminophenyl, 2-, 3- and 4-N-acetyl-N-methylamino-phenyl, 2-, 3- and 4-benzylaminophenyl, 2-, 3- and 4-N-methyl-N-phenylaminophenyl, 2-, 3- and 4-trifluoromethylphenyl, 4-hydroxy-3,5-dimethylphenyl, 3,5-di-t-butyl-4-hydroxyphenyl, 4-hydroxy-2,3,5-trimethylphenyl and 2,5-dimethylphenyl groups.

When W represents a heterocyclic group, this is a group having 5 or 6 ring atoms, of which from 1 to 3 are hetero-atoms selected from the group consisting of oxygen, sulfur and nitrogen atoms. In the case of those groups having 3 ring hereto-atoms, we prefer that all three, two or one are nitrogen atoms, and correspondingly none, one or two are oxygen and/or sulfur atoms. In the case of those groups having 2 ring hereto-atoms, we prefer that two, one or none are nitrogen atoms, and correspondingly none, one or two are oxygen and/or sulfur atoms. The group may be saturated or unsaturated, and, in the case of the unsaturated groups, may be aromatic or non-aromatic. The heterocyclic group may also optionally be fused to a carbocyclic or heterocyclic ring system having 5 or 6 ring atoms. These groups may be substituted or unsubstituted and, if substituted, the substituents are selected from the group consisting of substituents α, defined above and exemplified below. Although there is no restriction on the number of substituents except that imposed by the number of substitutable positions and possibly by steric constraints, we generally prefer from 1 to 4 substituents, more preferably 1 or 2 substituents and most preferably 1 substituent.

Examples of unsaturated groups include the 2-furyl, 3-furyl, 2-thienyl, 3-thienyl, 2-thiazolyl, 4-thiazolyl, 1-pyrrolyl, 2-pyrrolyl, 3-pyridyl, 4-pyridyl, 2-pyrimidinyl, 5-pyrimidinyl, 2-pyranyl, 4-pyranyl, 3-isoxazolyl, 4-isoxazolyl, 5-isoxazolyl, 2-oxazolyl and 5-oxazolyl groups.

Examples of saturated heterocyclic groups which may be represented by W include the 2-tetrahydrofuryl, 3-tetrahydrofuryl, 2-tetrahydrothienyl, 3-tetrahydrothienyl, 1-pyrrolidinyl, 3-pyrrolidinyl, 2-piperazyl, piperidino, 2-piperidyl, morpholino, 3-morpholinyl, 2-tetrahydropyranyl, 4-tetrahydropyranyl, 1,4-dioxan-2-yl, 1,3-dioxan-4-yl and 1,3-dioxan-5-yl groups.

When W represents a fused heterocyclic group, the heterocyclic part, which may be any of the groups defined and exemplified above is fused to another group which may be carbocyclic or heterocyclic, preferably carbocyclic, and which may be saturated or unsaturated. Examples of groups which may be fused to the heterocyclic group include the benzene, cyclopentane, cyclohexane, furan, pyran and pyridine rings. Examples of such fused ring groups include the 2-benzofuranyl, 2-2H-chromenyl, 2-benzothienyl, 2-indolinyl, 3-indolinyl, 2-dihydrobenzofuranyl, 2-chromanyl, 1,4-benzodioxan-2-yl, 4-quinolyl and 1-isoquinolyl groups.

Among these heterocyclic groups, 5- or 6-membered unsaturated, saturated and fused heterocyclic groups with 1 or 2 oxygen, sulfur or/and nitrogen atoms are preferred, and 5- or 6-membered saturated and unsaturated heterocyclic groups with 1 or 2 oxygen, sulfur or/and nitrogen atoms are most preferred.

When substituent α represents an alkyl group, this may be a straight or branched chain alkyl group having from 1 to 4, preferably 1 or 2, carbon atoms, and examples include the methyl, ethyl, propyl, isopropyl, butyl, isobutyl, sec-butyl and t-butyl groups. Of these, we prefer those alkyl groups having 1 or 2 carbon atoms, most preferably the methyl group.

When substituent α represents an alkoxy group, this may be a straight or branched chain alkoxy group having from 1 to 4, preferably 1 or 2, carbon atoms, and examples include the methoxy, ethoxy, propoxy, isopropoxy, butoxy, isobutoxy, sec-butoxy and t-butoxy groups. Of these, we prefer those alkoxy groups having 1 or 2 carbon atoms, most preferably the methoxy group.

When substituent α represents a haloalkyl group, this may be a straight or branched chain haloalkyl group having from 1 to 4, preferably 1 or 2, carbon atoms, and examples include the chloromethyl, fluoromethyl, trichloromethyl, trifluoromethyl, difluoromethyl, dichloromethyl, 2,2,2-trichloroethyl, 2-chloroethyl, 2-fluoroethyl and 2,2,2-tribromoethyl groups.

When substituent α represents a halogen atom, this may be, for example, a fluorine, chlorine, bromine or iodine atom, preferably a fluorine or chlorine atom.

When substituent α represents an amino group, this is a group of formula —$NR^aR^b$, in which $R^a$ and $R^b$ are as defined above. More specifically:

1) When $R^a$ and/or $R^b$ represents a straight or branched chain alkyl group having from 1 to 8 carbon atoms, the alkyl group may include, for example, the same alkyl groups as exemplified above in relation to $R^1$ and $R^2$.

2) When $R^a$ and/or $R^b$ represents an aralkyl group preferably having a total of from 7 to 11 carbon atoms, the aralkyl group may include, for example, the same aralkyl groups as exemplified above in relation to A and B.

3) When $R^a$ and/or $R^b$ represents an aryl group having from 6 to 10 carbon atoms, the aryl group may include, for example, the same aryl groups as exemplified above in relation to $R^6$ and/or $R^7$.

4) When $R^a$ and/or $R^b$ represents a straight or branched chain aliphatic acyl group having from 1 to 11 carbon atoms, the aliphatic acyl group may include, for example, the same aliphatic acyl groups as exemplified above in relation to A and B.

5) When $R^a$ and/or $R^b$ represents an aromatic-aliphatic acyl group having from 8 to 12 carbon atoms, the aromatic aliphatic acyl group may include, for example, the same aromatic-aliphatic acyl groups as exemplified above in relation to A and B.

6) When $R^a$ and/or $R^b$ represents an aromatic acyl group having from 7 to 11 carbon atoms, the aromatic acyl group may include, for example, the same aromatic acyl groups as exemplified above in relation to A and B.

Thus, when substituent α is an amino group, this may be an unsubstituted amino groups or one of the following groups:

1) Examples of straight or branched chain alkylamino groups having from 1 to 8 carbon atoms include, for example, the methylamino, ethylamino, propylamino, isopropylamino, butylamino, isobutylamino, sec-butylamino, t-butylamino, pentylamino, 2-pentylamino, 3-pentylamino, 2-methylbutylamino, 3-methylbutylamino, 1,1-dimethylpropylamino, 1,2-dimethylpropylamino, 2,2- dimethylpropylamino, hexylamino, 2-hexylamino, 3-hexylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1,1,2-trimethylpropylamino, 1,2,2-trimethylpropylamino, heptylamino, 2-heptylamino, 3-heptylamino, 4-heptylamino, 3,3-dimethylpentylamino, octylamino, 1-methylheptylamino, 2-ethylhexylamino and 1,1,3,3-tetramethylbutylamino groups.

2) Examples of straight or branched chain dialkylamino groups in which each alkyl part has from 1 carbon atoms include, for example, the dimethylamino, diethylamino, dipropylamino, diisopropylamino, dibutylamino, diisobutylamino, di-sec-butylamino, di-t-butylamino, dipentylamino, dihexylamino, diheptylamino, dioctylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-t-butylamino, N-methyl-N-pentylamino, N-methyl-N-hexylamino, N-methyl-N-heptylamino, N-methyl-N-octylamino, N-ethyl-N-propyl-amino, N-ethyl-N-isopropylamino, N-ethyl-N-butylamino, N-ethyl-N-isobutylamino, N-ethyl-N-sec-butylamino, N-ethyl-N-t-butylamino, N-ethyl-N-pentylamino, N-ethyl-N-hexylamino, N-ethyl-N-heptylamino, N-ethyl-N-octylamino, N-propyl-N-isopropylamino, N-propyl-N-butylamino, N-propyl-N-isobutylamino, N-propyl-N-sec-butylamino, N-propyl-N-t-butylamino, N-propyl-N-pentylamino, N-propyl-N-hexylamino, N-propyl-N-heptylamino, N-propyl-N-octylamino, N-butyl-N-isopropylamino, N-butyl-N-isobutylamino, N-butyl-N-sec-butylamino, N-butyl-N-t-butylamino, N-butyl-N-pentylamino, N-butyl-N-hexylamino, N-butyl-N-heptylamino and N-butyl-N-octylamino groups.

3) Examples of aralkylamino groups preferably having a total of from 7 to 11 carbon atoms include, for example, the benzylamino, 2-phenylethylamino, 1-phenylethylamino, 3-phenylpropylamino, 2-phenylpropylamino, 1-phenylpropylamino, 4-phenylbutylamino, 1-phenylbutylamino, 5-phenylpentylamino, 1-naphthylmethylamino and 2-naphthylmethylamino groups.

4) Examples of arylamino groups having from 6 to 10 carbon atoms include, for example, the phenylamino, 1-naphthylamino, 2-naphthylamino groups.

5) Examples of straight or branched chain aliphatic acylamino groups having from 1 to 11 carbon atoms include, for example, the formamido, acetamido, propionamido, isopropionamido and butyramido groups.

6) Examples of aromatic-aliphatic acylamino groups having a total of from 8 to 12 carbon atoms include, for example, the phenylacetamido, 3-phenylpropionamido, 4-phenylbutyramido, 5-phenylpentanoylamino and 6-phenylhexanoylamino groups.

7) Examples of aromatic acylamino groups having from 7 to 11 carbon atoms include, for example, the benzamido, 1-naphthoylamino and 2-naphthoylamino groups.

When Z represents a group of formula (i), (ii), (iii) or (iv):

(i)

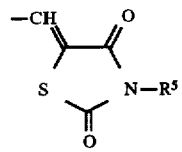

(ii)

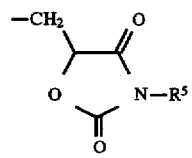

(iii)

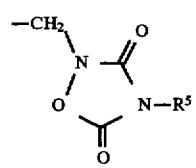

(iv)

$R^5$ is as defined above and exemplified below.

1) When $R^5$ represents a straight or branched chain carboxyalkyl group having from 2 to 5 carbon atoms, examples of such groups include the carboxymethyl, 1-carboxyethyl, 2-carboxyethyl, 1-carboxypropyl, 3-carboxypropyl, 1-carboxybutyl, 4-carboxybutyl and 1-carboxy-1-methylethyl groups.

2) When $R^5$ represents a straight or branched chain alkanoyloxyalkyl group having a total of from 2 to 12 carbon atoms, the alkanoyloxyalkyl group has an alkanoyl portion preferably having from 1 to 6 carbon atoms and an alkyl portion having from 1 to 6, preferably from 1 to 4, carbon atoms. Specific examples of such alkanoyloxyalkyl groups include the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups.

3) When $R^5$ represents a straight or branched chain alkanoyloxyalkyl group substituted by a cycloalkyl group and having a total of from 6 to 12 carbon atoms, the cycloalkyl part preferably has from 3 to 7 ring carbon atoms (for example, the cyclopropyl, cyclobutyl, cyclopentyl, cyclohexyl and cycloheptyl groups). The alkanoyloxyalkyl group has an alkanoyl portion preferably having from 2 to 6 carbon atoms and an alkyl portion having from 1 to 6, more preferably from 1 to 4 carbon atoms. Examples of such cycloalkyl-substituted alkanoyloxyalkyl groups include the cyclohexylacetoxymethyl, 1-(cyclohexylacetoxy)ethyl, 1-(cyclohexylacetoxy)propyl, 2-methyl-1-(cyclohexylacetoxy)propyl, cyclopentylacetoxymethyl, 1-(cyclopentylacetoxy)ethyl, 1-(cyclopentylacetoxy)propyl and 2-methyl-1-(cyclopentylacetoxy)propyl groups.

4) When $R^5$ represents a straight or branched chain cycloalkylcarbonyloxyalkyl group preferably having a total of from 5 to 17 carbon atoms, the cycloalkylcarbonyloxyalkyl group has a cycloalkyl portion having from 3 to 10, preferably from 3 to 7, carbon atoms, which is monocyclic or polycyclic, for example as exemplified above, a terpenyl group, such as a geranyl, neryl, linalyl, phytyl, menthyl (especially m- and p-menthyl), thujyl, caryl, pinanyl, bornyl, norcaryl, norpinanyl, norbornyl, menthenyl, camphenyl or norbornenyl group, or an adamantyl group. The alkyl portion thereof has from 1 to 6, preferably from 1 to 4, carbon atoms, and is preferably a methyl, ethyl or propyl group. If desired, the cycloalkyl portion may be substituted by at least one alkyl group with from 1 to 4 carbon atoms. Examples of such alkyl groups include the methyl, ethyl, propyl, butyl groups. Examples of such straight or branched cycloalkylcarbonyloxyalkyl groups with from 5 to 17 carbon atoms (which may additionally be substituted on the cycloalkyl ring by at least one alkyl substituent, as described above) include the 1-methylcyclohexylcarbonyloxymethyl, cyclopentylcarbonyloxymethyl, 1-cyclohexylcarbonyloxyethyl, 1-cyclopentylcarbonyloxymethyl, 1-cyclopentylcarbonyloxymethyl, 1-methylcyclopentylcarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)-propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantylcarbonyloxymethyl and 1-adamantylcarbonyloxymethyl groups.

5) When $R^5$ represents a straight or branched chain alkoxycarbonyloxyalkyl group having from 3 to 17 carbon atoms, the alkoxycarbonyloxyalkyl group has an alkoxy portion having from 1 to 10, preferably from 1 to 6, more preferably from 1 to 4, carbon atoms and an alkyl portion having from 1 to 6, preferably from 1 to 4, carbon atoms. Particularly preferred is a 1-(alkoxycarbonyloxy)ethyl group. Examples of such alkoxycarbonyloxyalkyl groups include the 1-methoxycarbonyloxyethyl, 1-ethoxycarbonyloxyethyl, 1-propoxycarbonyloxyethyl, 1-isopropoxycarbenyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups.

Another example of such an alkoxycarbonyloxyalkyl group has an alkoxy portion and an alkyl portion both having from 1 to 6, preferably from 1 to 4, carbon atoms. Examples of such alkoxycarbonyloxyalkyl groups include the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups.

6) When $R^5$ represents a straight or branched chain alkoxycarbonyloxyalkyl group substituted by a cycloalkyl group and having a total of from 6 to 17 carbon atoms, the cycloalkyl group has from 3 to 7 carbon atoms and may be as exemplified above. The alkoxycarbonyloxyalkyl group has an alkoxycarbonyl portion having from 2 to 6 carbon atoms and an alkyl portion having from 1 to 6, preferably from 1 to 4 carbon atoms. Examples of such cycloalkyl-substituted alkoxycarbonyloxyalkyl groups include the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy) ethyl, 1-(cyclopentylmethoxycarbonyloxy)ethyl and 1-(cyclohexylmethoxycarbonyloxy)ethyl groups.

7) When $R^5$ represents a straight or branched chain cycloalkyloxycarbonyloxyalkyl group having from 5 to 17 carbon atoms, the cycloalkyloxycarbonyloxyalkyl group has a cycloalkyl portion having from 3 to 10, preferably from 3 to 7, carbon atoms, which is monocyclic or polycyclic and may be as exemplified above. The alkyl portion thereof has from 1 to 6, preferably from 1 to 4, carbon atoms, and is preferably a methyl, ethyl or propyl group. If desired, the cycloalkyl portion may be substituted by at least one alkyl group with from 1 to 4 carbon atoms. Examples of such alkyl groups include the methyl, ethyl, propyl and butyl groups. Examples of such straight or branched chain cycloalkyloxycarbonyloxyalkyl groups with from 5 to 17 carbon atoms (which may additionally be substituted on the cycloalkyl ring by at least one alkyl substituent, as described above) include the 1-methylcyclopentyloxycarbonyloxymethyl, 1-methylcyclohexyloxycarbonyloxymethyl, cyclopentyloxycarbonyloxymethyl, 1-cyclohexyloxycarbonyloxyethyl, 1-cyclopentyloxycarbonyloxyethyl, 1-cycloheptyloxycarbonyloxyethyl, 2-methyl-1-(1-methylcyclohexyloxycarbonyloxy)propyl, 1-(1-methylcyclohexyloxycarbonyloxy)propyl, 2-(1-methylcyclohexyloxycarbonyloxy)propyl, 1-(cyclohexyloxycarbonyloxy)propyl, 2-(cyclohexyloxycarbonyloxy)propyl, 2-methyl-1-(1-methylcyclopentyloxycarbonyloxy)propyl, 1-(1-methylcyclopentyloxycarbonyloxy)propyl, 2-(1-methylcyclopentyloxycarbonyloxy)propyl, 1-(cyclopentyloxycarbonyloxy)propyl, 2-(cyclopentyloxycarbonyloxy)propyl, 1-(1-methylcyclopentyloxycarbonyloxy)ethyl, 1-(1-methylcyclopentyloxycarbonyloxy)propyl, adamantyloxycarbonyloxymethyl and 1-adamantyloxycarbonyloxyethyl groups.

When the compounds of the present invention contain a carboxy group, for example when $R^5$ in the formula for Z represents a carboxyalkyl group, the compounds of the invention can form esters, which may be prepared by conventional esterification techniques. There is no particular restriction on the nature of the ester, provided that, where the resulting compound is to be used medically, the compound is pharmaceutically acceptable, that is it is not less active, or unacceptably less active, nor more toxic, or unacceptably more toxic, than the parent compound. However, where the compound is to be used for non-medical uses, e.g. as an intermediate in the preparation of other compounds, even this restriction does not apply, and there is then no restriction on the nature of the esters which may be formed.

Examples of ester groups include:

alkyl groups having from 1 to 20 carbon atoms, more preferably from 1 to 10 carbon atoms, such as those exemplified in relation to $R^1$ and $R^2$ and higher alkyl groups as are well known in the art, such as the nonyl, decyl, dodecyl, tridecyl, pentadecyl, octadecyl, nonadecyl and icosyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituent such as substituents α defined and exemplified above, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl) ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred;

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents α defined and exemplified above, for example the 2-tri($C_1$–$C_4$)alkylsilylethyl groups, especially a 2-trimethylsilylethyl group;

phenyl groups, in which the phenyl group is unsubstituted or substituted by at least one substituent selected from the group consisting of substituents α as defined and exemplified above, preferably with at least one alkyl group having from 1 to 4 carbon atoms or acylamino group, for example the phenyl, tolyl and benzamidophenyl groups;

phenacyl groups, which may be unsubstituted or have at least one of substituents α defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, notcaryl, norpinanyl, norbornyl, menthenyl, camphenyl and norbornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups; cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the cyclohexylacetoxymethyl, 1-(cyclohexylacetoxy)ethyl, 1-(cyclohexylacetoxy)propyl, 2-methyl-1-(cyclohexylacetoxy)-propyl, cyclopentylacetoxymethyl, 1-(cyclopentylacetoxy) ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-(cyclohexyloxycarbonyloxy)ethyl, 1-(cyclohexylcarbonyloxy)ethyl, 1-(cyclopentyloxycarbonyloxy)ethyl, 1-(cyclopentylcarbonyloxy)ethyl, 1-(cycloheptyloxycarbonyloxy)ethyl, 1-(cycloheptylcarbonyloxy)ethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxymethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one substituent such as substituents α, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5, 6,7-tetrahydro1,3-benzodioxolen-4-yl groups.

Of the above groups, we especially prefer straight or branched chain alkyl groups having from 1 to 10 carbon atoms, for example the methyl, ethyl, propyl, isopropyl, butyl, sec-butyl, isobutyl, t-butyl, pentyl, 1-methylbutyl, 2-methylbutyl, 3-methylbutyl, 1,1-dimethylpropyl, 2,2-dimethylpropyl, 1,2-dimethylpropyl, 1-ethylpropyl, hexyl, 1-methylpentyl, 2-methylpentyl, 1,1-dimethylbutyl, 1,3-dimethylbutyl, 1-ethylbutyl, 2-ethylbutyl, 1-methyl-1-ethylpropyl, heptyl, 1-methyl-1-ethylbutyl, 2-methyl-2-ethylbutyl, octyl, 1-methylheptyl, 2-ethylhexyl and 1,1,3,3-tetramethylbutyl groups.

When the compound of the present invention contains a basic group in its molecule, for example when B represents a hydrogen atom, an alkyl group or an aralkyl group, when W in the formula for X has an amino group as a substituent or when $X^1$ represents a group of formula >NR$^4$, the compound of the present invention can be converted to salts with acids by conventional methods. There is no particular restriction on the nature of such salts, provided that, where the compounds are to be used medically, the compounds are pharmaceutically acceptable. However, where the compound is to be used for non-medical uses, e.g. as an intermediate in the preparation of other compounds, even this restriction does not apply, and there is then no restriction on the nature of the salts which may be formed. Examples of such salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. We prefer the pharmaceutically acceptable salts.

When $R^5$ in the formulae for Z represents a hydrogen atom or a carboxyalkyl group, the compound of the present invention can be converted into a salt with a base by conventional methods. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine. We prefer the pharmaceutically acceptable salts.

The compounds of formula (I) of the present invention can exist in the form of various isomers. Thus, as shown in formula (Ia):

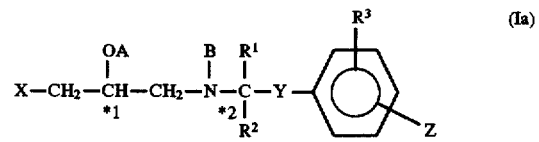

(wherein $R^1$, $R^2$, $R^3$, A, B, X, Y and Z are as defined above), the carbon atom marked with *1 is always an asymmetric carbon atom, and the carbon atom marked with *2 is an asymmetric carbon atom when $R^1$ and $R^2$ are different groups.

Furthermore, when Z represents a group of formula (i-a) or (iii-a):

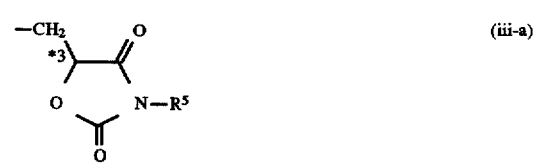

(wherein $R^5$ is as defined above), the carbon atom marked with *3 is also an asymmetric carbon atom.

Although these isomers are all represented herein by a single molecular formula (I), the present invention includes both the individual, isolated isomers and mixtures, including racemates, thereof and the isomers may be present in such mixtures in any proportions. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

In addition, when Z represents a group of formula (i), (ii), (iii) or (iv):

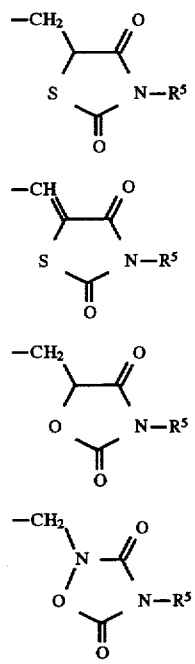

and $R^5$ represents a hydrogen atom, the resulting compounds can form tautomers, as shown by the following schemes α, β, γ and δ:

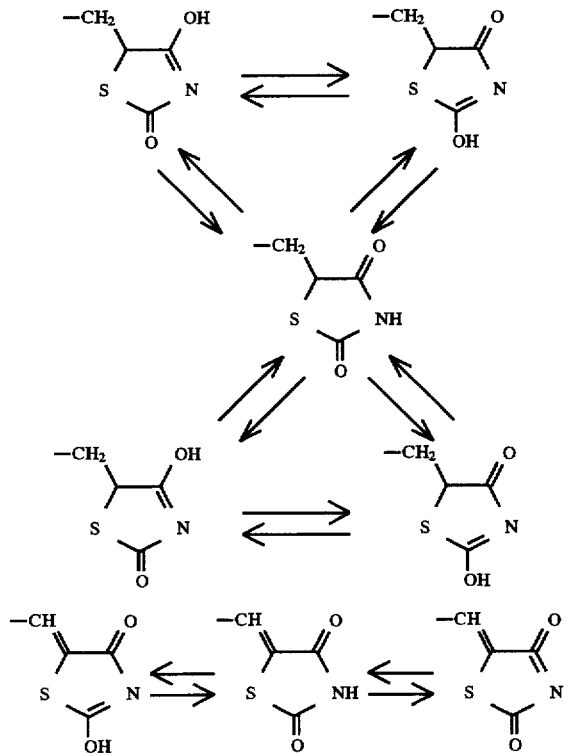

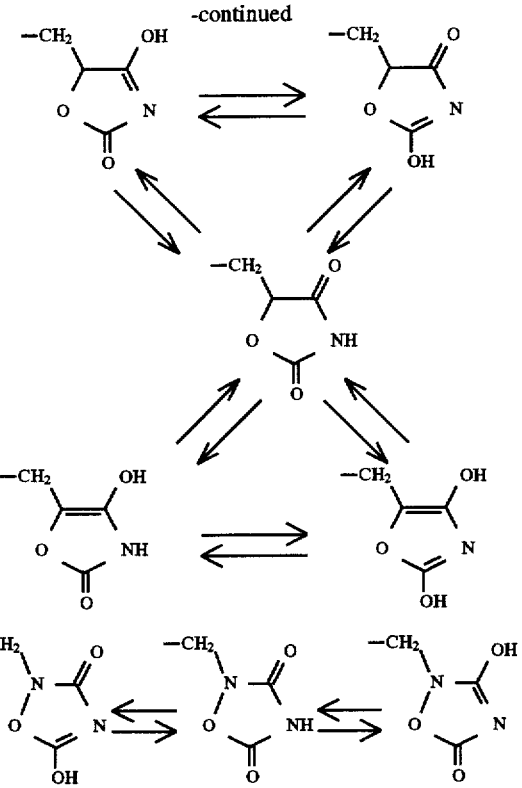

In the above formula (I), all tautomers based thereon and mixtures of equivalent weights or non-equivalent weights of these tautomers are represented by one formula. Thus, all of these isomers and mixtures of these isomers are included in the present invention.

Moreover, the present invention also includes all solvates, for example hydrates, of the compounds of formula (I) and salts and esters thereof, where the relevant compound is capable of forming a solvate.

The invention also embraces all compounds which could be converted in the living mammalian, for example human, body to a compound of formula (I) or a salt or ester thereof by the action of the metabolism, that is so-called "pro-drugs" of the compounds of formula (I) and salts and esters thereof.

Of the compounds of the present invention, we prefer those compounds of formula (I) and salts and esters thereof, in which:

(1) $R^1$ and $R^2$ are the same or different and each represents a hydrogen atom or an alkyl group having from 1 to 6 carbon atoms;

$R^3$ represents a hydrogen atom, an alkyl group having from 1 to 4 carbon atoms, a methoxy, ethoxy or propoxy group or a halogen atom;

A and B are the same or different and each represents a hydrogen atom, an alkyl group having from 1 to 4 carbon atoms, an aliphatic acyl group having from 1 to 6 carbon atoms or a carbamoyl group, or A and B together form a group of formula —C(=O)—, —C(=S)—, —CH$_2$C(=O)—, —CH$_2$CH$_2$— or -S(=O) (=O)—;

X represents a group of formula W—(CH$_2$)$_m$—X'—, wherein W represents an aryl group which has from 6 to 10 ring carbon atoms and which is unsubstituted or is substituted by from 1 to 3 substituents selected from the group consisting of substituents α, defined above

19

X' represents a single bond, an oxygen atom, a sulfur atom or a group of formula —N(—R$^4$)— (in which R$^4$ represents a hydrogen atom or an alkyl group having from 1 to 4 carbon atoms);

m is 0 or an integer of from 1 to 8;

Y is a group of formula —(CH$_2$)$_n$—Y'—,
wherein Y' represents a single bond, a oxygen atom or a sulfur atom, and n is an integer of from 1 to 5; and Z represents a group of formula (vii), (viii) or (ix):

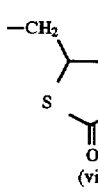 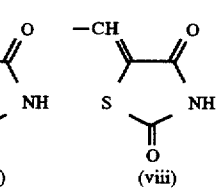 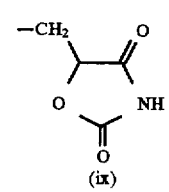

More preferred compounds of the present invention are those compounds of formula (I) and salts and esters thereof, in which:

(2) R$^1$ and R$^2$ are the same or different and each represents a hydrogen atom or an alkyl group having from 1 to 4 carbon atoms;

R$^3$ represents a hydrogen atom, a methyl, ethyl, methoxy or ethoxy group or a fluorine or chlorine atom;

A and B are the same or different and each represents a hydrogen atom, a methyl, ethyl, propyl, acetyl, propionyl, butyryl or carbamoyl group, or A and B together form a group of formula —C(=O)—, —C(=S)—, or —CH$_2$CH$_2$—;

X represents a group of formula W—(CH$_2$)$_m$—X'—,
wherein W represents a phenyl group which is unsubstituted or is substituted by from 1 to 3 substituents selected from the group consisting of substituents α, defined above X' represents a single bond, an oxygen atom, a sulfur atom or a group of formula —N(—R$^4$)— (wherein R$^4$ represents a hydrogen atom, or a methyl, ethyl or propyl group);

m is 0 or an integer of from 1 to 6;

Y is a group of formula —(CH$_2$)$_n$—Y'—,
wherein Y' represents a oxygen atom or a sulfur atom, and n is an integer of from 1 to 5; and Z represents a group of formula (vii) or (viii):

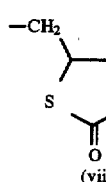 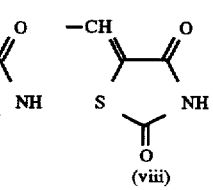

Still more preferred compounds of the present invention are those compounds of formula (I) and salts and esters thereof, in which:

(3) R$^1$ and R$^2$ both represent hydrogen atoms, or one of them represents a hydrogen atom and the other represents an alkyl group having from 1 to 4 carbon atoms;

R$^3$ represents a hydrogen atom, a methyl or methoxy group or a chlorine atom;

A and B are the same or different and each represents a hydrogen atom, a methyl, ethyl, acetyl, propionyl or carbamoyl group, or A and B together form a group of formula —C(=O)—, —C(=S)— or —CH$_2$CH$_2$—;

20

X represents a group of formula W—(CH$_2$)$_m$—X'—,
wherein W represents a phenyl group which is unsubstituted or is substituted by from 1 to 3 substituents selected from the group consisting of halogen atoms and methyl, ethyl, hydroxy, phenyl, amino, dimethylamino, methoxy and ethoxy groups, X' represents a single bond, an oxygen atom, a sulfur atom or a group of formula —NH— or —N(Me)—;

m is 0 or an integer of from 1 to 6;

Y represents a group of formula —(CH$_2$)$_n$—Y'—,
wherein Y' represents a oxygen atom or a sulfur atom, and n is an integer of from 1 to 3; and Z represents a group of formula (vii):

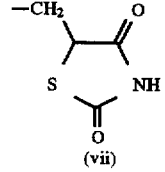

Even more preferred compounds of the present invention are those compounds of formula (I) and salts and esters thereof, in which:

(4) R$^1$ and R$^2$ both represent hydrogen atoms or one of them represents a hydrogen atom and the other represents a methyl, ethyl, propyl or isopropyl group;

R$^3$ represents a hydrogen atom, a methyl group or a chlorine atom;

A represents a hydrogen atom and B represents a hydrogen atom, or a methyl, ethyl or acetyl group, or A and B together form a group of formula —C(=O)— or —C(=S)—;

X represents a group of formula W—(CH$_2$)$_m$—X'—,
wherein W represents a halogen-substituted phenyl, phenylphenyl, methoxyphenyl or phenyl group, X' represents an oxygen atom or a sulfur atom;

m represents 0 or an integer of from 1 to 6;

Y represents a group of formula —CH$_2$O— or —(CH$_2$)$_2$—O—; and

Z represents a group of formula (vii):

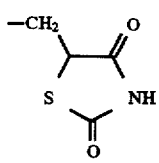

The most preferred compounds of the present invention are those compounds of formula (I) and salts and esters thereof, in which:

(5) R$^1$ and R$^2$ both represent hydrogen atoms or one of them represents a hydrogen atom and the other represents a methyl or ethyl group;

R$^3$ represents a hydrogen atom;

A represents a hydrogen atom and B represents a hydrogen atom or a methyl group, or A and B together form a group of formula —C(=O)— or —C(=S)—;

X represents a group of formula W—(CH$_2$)$_m$—O—,
wherein W represents a phenyl, 3-chlorophenyl, 4-chlorophenyl, 3-methoxyphenyl, 4-methoxyphenyl or 4-phenylphenyl group, and m represents 0 or an integer of from 1 to 6;

Y represents a group of formula —CH$_2$O—; and

Z represents a group of formula (vii):

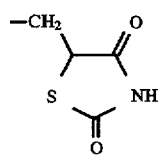
(vii)

Examples of certain compounds of the present invention are given in the following formulae (I-1) to (I-7):

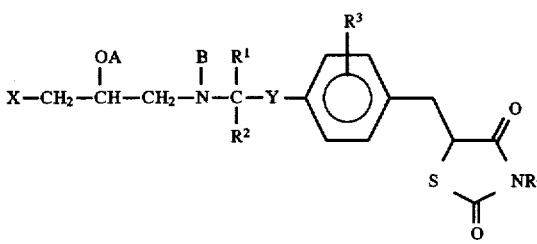
(I-1)

(I-2)

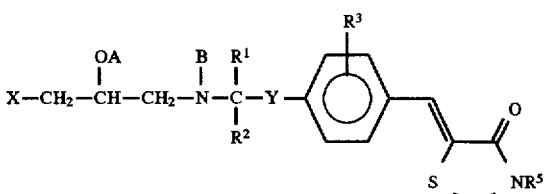
(I-3)

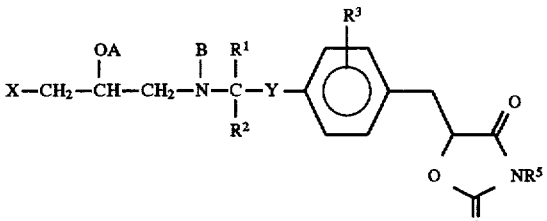
(I-4)

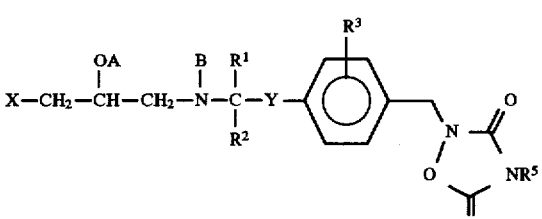

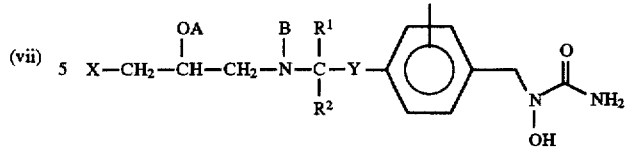
(I-5)

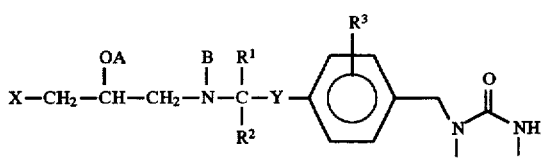
(I-6)

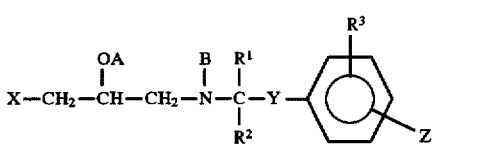
(I-7)

In the above formulae, the substituents are as defined in the following one of Tables 1 to 7, respectively. That is, Table 1 relates to formula (I-1), Table 2 relates to formula (I-2), and so on to Table 7, which relates to formula (I-7). In the Tables, the following abbreviations are used:

| | |
|---|---|
| Ac | acetyl |
| Boz | benzoyl |
| Bu | butyl |
| iBu | isobutyl |
| tBu | t-butyl |
| Bz | benzyl |
| Car | carbamoyl |
| Et | ethyl |
| Etc | ethoxycarbonyl |
| Hp | heptyl |
| Hx | hexyl |
| Me | methyl |
| Mec | methoxycarbonyl |
| Oc | octyl |
| Ph | phenyl |
| Piv | pivaloyl |
| Pn | pentyl |
| Pr | propyl |
| iPr | isopropyl |
| Pm | propionyl |
| Pyr | pyridyl |

In Table 7, the position of the substituents R$^3$ and Z with respect to Y is indicated in brackets in the Table after the identification of the substituent.

TABLE 1

| Cpd. No. | X | A | B | Y | R$^1$ | R$^2$ | R$^3$ | R$^5$ |
|---|---|---|---|---|---|---|---|---|
| 1-1 | Ph | H | H | —CH$_2$—O— | H | H | H | H |
| 1-2 | Ph | H | H | —CH$_2$—O— | Me | H | H | H |
| 1-3 | Ph | | —CO— | —CH$_2$—O— | H | H | H | H |
| 1-4 | Ph | | —CO— | —CH$_2$—O— | Me | H | H | H |
| 1-5 | Ph | | —CS— | —CH$_2$—O— | H | H | H | H |
| 1-6 | Ph | | —CS— | —CH$_2$—O— | Me | H | H | H |
| 1-7 | Ph | | —CH$_2$—CO— | —CH$_2$—O— | H | H | H | H |
| 1-8 | Ph | | —CH$_2$—CO— | —CH$_2$—O— | Me | H | H | H |
| 1-9 | Ph | | —CO—CO— | —CH$_2$—O— | H | H | H | H |
| 1-10 | Ph | | —CO—CO— | —CH$_2$—O— | Me | H | H | H |

TABLE 1-continued

| Cpd. No. | X | A | B | Y | $R^1$ | $R^2$ | $R^3$ | $R^5$ |
|---|---|---|---|---|---|---|---|---|
| 1-11 | Ph | | —SO₂— | —CH₂—O— | H | H | H | H |
| 1-12 | Ph | | —SO₂— | —CH₂—O— | Me | H | H | H |
| 1-13 | Ph | Ac | Ac | —CH₂—O— | H | H | H | H |
| 1-14 | Ph | Bz | Bz | —CH₂—O— | H | H | H | H |
| 1-15 | PhO— | H | H | —CH₂—O— | H | H | H | H |
| 1-16 | PhO— | H | H | —CH₂—O— | Me | H | H | H |
| 1-17 | PhO— | H | H | —CH₂—O— | iBu | H | H | H |
| 1-18 | PhO— | H | H | —CH₂—O— | H | H | Me | H |
| 1-19 | PhO— | H | H | —CH₂—O— | H | H | —OMe | H |
| 1-20 | PhO— | H | H | —CH₂—O— | H | H | Cl | H |
| 1-21 | PhO— | H | H | —CH₂—O— | H | H | OH | H |
| 1-22 | PhO— | H | H | —(CH₂)₂—O— | H | H | H | H |
| 1-23 | PhO— | H | H | —(CH₂)₃—O— | H | H | H | H |
| 1-24 | PhO— | H | H | —(CH₂)₅—O— | H | H | H | H |
| 1-25 | PhO— | H | Me | —CH₂—O— | H | H | H | H |
| 1-26 | PhO— | H | Bu | —CH₂—O— | H | H | H | H |
| 1-27 | PhO— | H | Bz | —CH₂—O— | H | H | H | H |
| 1-28 | PhO— | Me | Bz | —CH₂—O— | H | H | H | H |
| 1-29 | PhO— | Bz | H | —CH₂—O— | H | H | H | H |
| 1-30 | PhO— | H | Ac | —CH₂—O— | H | H | H | H |
| 1-31 | PhO— | Ac | Ac | —CH₂—O— | H | H | H | H |
| 1-32 | PhO— | H | Piv | —CH₂—O— | H | H | H | H |
| 1-33 | PhO— | Me | Ac | —CH₂—O— | H | H | H | H |
| 1-34 | PhO— | H | Boz | —CH₂—O— | H | H | H | H |
| 1-35 | PhO— | H | 3-PhPrn | —CH₂—O— | H | H | H | H |
| 1-36 | PhO— | H | H₂NCO— | —CH₂—O— | H | H | H | H |
| 1-37 | PhO— | H | MeNHCO— | —CH₂—O— | H | H | H | H |
| 1-38 | PhO— | H | BuNHCO— | —CH₂—O— | H | H | H | H |
| 1-39 | PhO— | H | Et₂NCO— | —CH₂—O— | H | H | H | H |
| 1-40 | PhO— | H | PhNHCO— | —CH₂—O— | H | H | H | H |
| 1-41 | PhO— | H | BzNHCO— | —CH₂—O— | H | H | H | H |
| 1-42 | PhO— | Ac | PhNHCO— | —CH₂—O— | H | H | H | H |
| 1-43 | PhO— | Me | EtNHCO— | —CH₂—O— | H | H | H | H |
| 1-44 | PhO— | Ac | Me | —CH₂—O— | H | H | H | H |
| 1-45 | PhO— | Ac | Me | —CH₂—O— | Me | H | H | H |
| 1-46 | PhO— | Ac | Me | —CH₂—O— | Me | H | H | —CH₂OAc |
| 1-47 | PhO— | | —CO— | —CH₂—O— | H | H | H | H |
| 1-48 | PhO— | | —CO— | —CH₂—O— | Me | H | H | H |
| 1-49 | PhO— | | —CO— | —(CH₂)₂—O— | H | H | H | H |
| 1-50 | PhO— | | —CS— | —CH₂—O— | H | H | H | H |
| 1-51 | PhO— | | —CS— | —CH₂—O— | Me | H | H | H |
| 1-52 | PhO— | | —SO₂— | —CH₂—O— | H | H | H | H |
| 1-53 | PhO— | | —COCO— | —CH₂—O— | H | H | H | H |
| 1-54 | PhO— | | —CH₂CO— | —CH₂—O— | H | H | H | H |
| 1-55 | PhO— | | —(CH₂)₂— | —CH₂—O— | H | H | H | H |
| 1-56 | PhO— | | —(CH₂)₂— | —CH₂—O— | Me | H | H | H |
| 1-57 | PhO— | | —(CH₂)₂— | —CH₂—O— | Me | Me | H | H |
| 1-58 | PhO— | | —(CH₂)₂— | —(CH₂)₂—O— | Me | Me | H | H |
| 1-59 | PhO— | | —(CH₂)₂— | —(CH₂)₂—O— | Me | H | Cl | H |
| 1-60 | PhN(Me)— | | —(CH₂)₂— | —CH₂—O— | H | H | OH | H |
| 1-61 | PhO— | | —(CH₂)₂— | —CH₂—O— | H | H | H | —CH₂OPiv |
| 1-62 | PhO— | | —CH₂SO₂— | —CH₂—O— | H | H | H | H |
| 1-63 | BzO— | H | H | —CH₂—O— | H | H | H | H |
| 1-64 | BzO— | H | H | —CH₂—O— | Me | H | H | H |
| 1-65 | BzO— | | —CO— | —CH₂—O— | H | H | H | H |
| 1-66 | BzO— | | —CS— | —CH₂—O— | Me | H | H | H |
| 1-67 | BzO— | | —CO— | —(CH₂)₂—O— | H | H | H | H |
| 1-68 | 2-PhEtO— | H | H | —CH₂—O— | H | H | H | H |
| 1-69 | 2-PhEtO— | H | H | —CH₂—O— | Me | H | H | H |
| 1-70 | 2-PhEtO— | | —CO— | —CH₂—O— | H | H | H | H |
| 1-71 | 2-PhEtO— | | —CS— | —CH₂—O— | Me | H | H | H |
| 1-72 | 2-PhEtO— | | —CH₂CO— | —CH₂—O— | H | H | H | —CH₂CO₂Me |
| 1-73 | 3-PhPrO— | H | H | —CH₂—O— | H | H | H | H |
| 1-74 | 3-PhPrO— | H | H | —CH₂—O— | Me | H | H | H |
| 1-75 | 3-PhPrO— | | —CO— | —CH₂—O— | H | H | Cl | H |
| 1-76 | 3-PhPrO— | | —CS— | —CH₂—O— | H | H | H | H |
| 1-77 | 4-PhBuO— | H | H | —CH₂—O— | H | H | H | H |
| 1-78 | 4-PhBuO— | H | H | —CH₂—O— | Me | Me | H | H |
| 1-79 | 4-PhBuO— | | —CO— | —CH₂—O— | H | Me | H | H |
| 1-80 | 4-PhBuO— | | —(CH₂)₂— | —CH₂—O— | H | H | H | H |
| 1-81 | 5-PhPnO— | H | H | —CH₂—O— | H | H | H | H |
| 1-82 | 5-PhPnO— | | —CO— | —CH₂—O— | H | H | H | H |
| 1-83 | 6-PhHxO— | H | H | —CH₂—O— | H | H | H | H |
| 1-84 | 6-PhHxO— | | —CO— | —CH₂—O— | H | H | H | H |
| 1-85 | 7-PhHpO— | H | H | —CH₂—O— | H | H | H | H |
| 1-86 | 7-PhHpO— | | —CO— | —CH₂—O— | H | H | H | H |

TABLE 1-continued

| Cpd. No. | X | A | B | Y | R¹ | R² | R³ | R⁵ |
|---|---|---|---|---|---|---|---|---|
| 1-87 | 8-PhOcO— | H | H | —CH₂—O— | H | H | H | H |
| 1-88 | 8-PhOcO— | | —CO— | —CH₂—O— | H | H | H | H |
| 1-89 | 8-PhOcO— | | —CS— | —CH₂—O— | Me | H | H | H |
| 1-90 | 8-PhOcO— | | —CS— | —CH₂—O— | Me | H | H | —CH(Me)OAc |
| 1-91 | 3-ClPhO— | H | H | —CH₂—O— | H | H | H | H |
| 1-92 | 3-ClPhO— | H | H | —CH₂—O— | Me | H | H | H |
| 1-93 | 3-ClPhO— | | —CO— | —CH₂—O— | H | H | H | H |
| 1-94 | 3-ClPhO— | | —CO— | —CH₂—O— | Me | H | H | H |
| 1-95 | 3-ClPhO— | | —CS— | —CH₂—O— | Me | H | H | H |
| 1-96 | 3-ClPhO— | | —CH₂—O— | —CH₂—O— | Me | H | H | H |
| 1-97 | 2-ClPhO— | H | H | —CH₂—O— | Me | H | H | H |
| 1-98 | 2-ClPhO— | | —CO— | —CH₂—O— | H | H | H | H |
| 1-99 | 4-ClPhO— | H | H | —CH₂—O— | H | H | H | H |
| 1-100 | 4-ClPhO— | | —CO— | —CH₂—O— | H | H | H | H |
| 1-101 | 4-ClPhO— | | —CS— | —(CH₂)₂—O— | Me | H | H | EtcMe |
| 1-102 | 3-MePhO— | H | H | —CH₂—O— | Me | H | H | H |
| 1-103 | 3-MePhO— | | —CO— | —CH₂—O— | H | H | H | H |
| 1-104 | 4-tBuPhO— | H | H | —CH₂—O— | H | H | H | H |
| 1-105 | 3-MeOPhO— | H | H | —CH₂—O— | H | H | H | H |
| 1-106 | 3-MeOPhO— | | —CS— | —CH₂—O— | Me | H | H | H |
| 1-107 | 4-MeOPhO— | | | —CH₂—O— | Me | H | H | H |
| 1-108 | 3-BrPhO— | H | H | —CH₂—O— | Me | H | H | H |
| 1-109 | 3-BrPhO— | | —CO— | —CH₂—O— | H | H | H | H |
| 1-110 | 3-HOPhO— | H | H | —CH₂—O— | H | H | H | H |
| 1-111 | 3-HOPhO— | | —CO— | —CH₂—O— | Me | H | H | H |
| 1-112 | 3-NO₂PhO— | H | H | —CH₂—O— | Me | H | H | H |
| 1-113 | 3-NO₂PhO— | | —CO— | —CH₂—O— | Me | H | H | H |
| 1-114 | 3-NH₂PhO— | H | H | —CH₂—O— | Me | H | H | H |
| 1-115 | 3-NH₂PhO— | | —CO— | —CH₂—O— | Me | H | H | H |
| 1-116 | 4-MeNHPhO— | H | H | —CH₂—O— | Me | H | H | H |
| 1-117 | 3-MeNAcPhO— | H | H | —CH₂—O— | Me | H | H | H |
| 1-118 | 3-MeNAcPhO— | | —CO— | —CH₂—O— | Me | H | H | H |
| 1-119 | 3-BzNHPhO— | | —CS— | —CH₂—O— | Me | H | H | H |
| 1-120 | 3-BzNHPhO— | | —CS— | —CH₂— | H | H | H | H |
| 1-121 | 3-PhNMePhO— | H | H | —CH₂— | H | H | H | H |
| 1-122 | 3-PhNMePhO— | | —CO— | —(CH₂)₃O— | H | H | H | H |
| 1-123 | PhO— | H | H | —CH₂—S— | H | H | H | H |
| 1-124 | PhO— | | —CO— | —CH₂—S— | H | H | H | H |
| 1-125 | 3-CF₃PhO— | H | H | —CH₂—S— | H | H | H | H |
| 1-126 | 3-CF₃PhO— | | —CO— | —CH₂—S— | Me | H | H | H |
| 1-127 | PhS— | H | H | —CH₂—O— | H | H | H | H |
| 1-128 | PhS— | | —CO— | —CH₂—O— | Me | H | H | H |
| 1-129 | 4-HOPhS— | | —CH₂SO₂— | —CH₂—O— | H | H | H | H |
| 1-130 | Me(2-Pyr)N— | H | H | —CH₂—O— | H | H | H | H |
| 1-131 | Me(2-Pyr)N— | | —CO— | —CH₂—O— | Me | H | H | H |
| 1-132 | Me(2-Pyr)N— | | —CS— | —CH₂—O— | Me | H | H | H |
| 1-33 | Me(2-Pyr)N— | | —CH₂CO— | —CH₂—O— | Me | H | H | —CH₂CO₂Me |
| 1-134 | Me(2-Pyr)N— | | —(CH₂)₂— | —(CH₂)₅—O— | H | H | H | H |
| 1-135 | Me(2-Pyr)N— | | —(CH₂)₂— | —CH₂— | H | H | H | H |
| 1-136 | iPr(2-Pyr)N— | | —CO— | —CH₂—O— | H | H | H | —CH₂OPiv |
| 1-137 | iPr(2-Pyr)N— | | —SO₂— | —CH₂—O— | Me | Me | Cl | H |
| 1-138 | 2-PyrS— | H | H | —CH₂—O— | Me | H | H | H |
| 1-139 | 3-HO-2-PyrS— | | —CO— | —CH₂—O— | H | H | H | H |
| 1-140 | 4-PyrS— | H | H | —CH₂—O— | Me | H | H | H |
| 1-141 | 4-PyrS— | | —CO— | —CH₂—O— | Me | H | H | 2-EtcEt |
| 1-142 | 4-PyrS— | | —CS— | —CH₂—O— | Me | H | H | H |
| 1-143 | PhO— | H | H | —CH₂—O— | —(CH₂)₂— | H | H | H |
| 1-144 | PhO— | H | H | —CH₂—O— | —(CH₂)₃— | H | H | H |
| 1-145 | PhO— | H | H | —CH₂—O— | —(CH₂)₄— | H | H | H |
| 1-146 | PhO— | H | H | —CH₂—O— | —(CH₂)₅— | H | H | H |
| 1-147 | 3-ClPhO— | | —CO— | —CH₂—O— | —(CH₂)₅— | H | H | MecMe |
| 1-148 | 4-MePhS— | | —CO— | —(CH₂)₂—O— | —(CH₂)₅— | H | H | H |
| 1-149 | Me(2-Pyr)N— | | —CS— | —(CH₂)₂—O— | —(CH₂)₄— | —OMe | H | |
| 1-150 | Me(2-Pyr)N— | | —(CH₂)₂— | —CH₂—O— | —(CH₂)₄— | Me | | —CH—OPiv<br>\|<br>Me |
| 1-151 | Bz(2-Pyr)N— | H | H | —CH₂—O— | Me | H | H | H |
| 1-152 | Bz(2-Pyr)N— | | —CO— | —CH₂—O— | H | H | H | H |
| 1-153 | Ph(2-Pyr)N— | H | H | —CH₂—O— | H | H | H | H |
| 1-154 | Ph(2-Pyr)N— | | —CS— | —CH₂—O— | H | H | H | H |
| 1-155 | Ph(2-Pyr)N— | H | Ac | —CH₂—O— | H | H | H | H |
| 1-156 | Me(2-Pyr)N— | Ac | MeCar | —CH₂—O— | Me | H | H | H |
| 1-157 | Me(2-Pyr)N— | EtCar | EtCar | —CH₂—O— | H | H | H | H |
| 1-158 | 3-ClPhO— | H | H | —CH₂—S— | Me | H | H | H |

TABLE 1-continued

| Cpd. No. | X | A | B | Y | $R^1$ | $R^2$ | $R^3$ | $R^5$ |
|---|---|---|---|---|---|---|---|---|
| 1-159 | 3-ClPhO— | | —CO— | —CH$_2$—S— | Me | H | H | H |
| 1-160 | 5-PhPnO— | H | H | —CH$_2$—O— | Me | H | H | H |
| 1-161 | 4-PhBuO— | H | H | —CH$_2$—O— | Me | H | H | H |
| 1-162 | 6-PhHxO— | H | H | —CH$_2$—O— | Me | H | H | H |
| 1-163 | 8-PhOcO— | H | H | —CH$_2$—O— | Me | H | H | H |
| 1-164 | BzO— | | —CO— | —CH$_2$—O— | Me | H | H | H |
| 1-165 | 2-PhEtO— | | —CO— | —CH$_2$—O— | Me | H | H | H |
| 1-166 | 3-PhPrO— | | —CO— | —CH$_2$—O— | Me | H | H | H |
| 1-167 | 5-PhPnO— | | —CO— | —CH$_2$—O— | Me | H | H | H |
| 1-168 | 6-PhHxO— | | —CO— | —CH$_2$—O— | Me | H | H | H |
| 1-169 | 8-PhOcO— | | —CO— | —CH$_2$—O— | Me | H | H | H |
| 1-170 | 7-PhHpO— | | —CO— | —CH$_2$—O— | Me | H | H | H |
| 1-171 | 3-FPhO— | | —CO— | —CH$_2$—O— | Me | H | H | H |
| 1-172 | 3-FPhO— | | —CS— | —CH$_2$—O— | Me | H | H | H |
| 1-173 | 4-MeOPhO— | | —CO— | —CH$_2$—O— | Me | H | H | H |
| 1-174 | 4-MeOPhO— | | —CS— | —CH$_2$—O— | Me | H | H | H |
| 1-175 | 3-(NMe$_2$)PhO— | H | H | —CH$_2$—O— | H | H | H | H |
| 1-176 | 3-(NMe$_2$)PhO— | H | H | —CH$_2$—O— | Me | H | H | H |
| 1-177 | 3-(NMe$_2$)PhO— | | —CO— | —CH$_2$—O— | Me | H | H | H |
| 1-178 | 4-(NMe$_2$)PhO— | | —CS— | —CH$_2$—O— | H | H | H | H |
| 1-179 | 4-PhPhO— | H | H | —CH$_2$—O— | Me | H | H | H |
| 1-180 | 4-PhPhO— | | —CO— | —CH$_2$—O— | Me | H | H | H |
| 1-181 | 4-PhPhO— | | —CS— | —CH$_2$—O— | Me | H | H | H |
| 1-182 | PhS— | H | H | —CH$_2$—O— | Me | H | H | H |
| 1-183 | PhN(Me)— | H | H | —CH$_2$—O— | Me | H | H | H |
| 1-184 | PhN(Me)— | | —CO— | —CH$_2$—O— | Me | H | H | H |
| 1-185 | (3-ClPh)N(Me)— | | —CS— | —CH$_2$—O— | H | H | H | H |
| 1-186 | 3-ClBzO— | H | H | —CH$_2$—O— | Me | H | H | H |
| 1-187 | 3-ClBzO— | | —CO— | —CH$_2$—O— | Me | H | H | H |
| 1-188 | 3-ClBzO— | | —CS— | —CH$_2$—O— | Me | H | H | H |
| 1-189 | 3-ClBzO— | | —CS— | —CH$_2$—O— | Me | H | H | Na |
| 1-190 | 3-ClPhO— | H | H | —CH$_2$—O— | H | Et | H | H |
| 1-191 | 3-ClPhO— | | —CO— | —CH$_2$—O— | H | Et | H | H |
| 1-192 | 3-ClPhO— | | —CS— | —CH$_2$—O— | H | Et | H | H |
| 1-193 | 3-ClPhO— | | —CO— | —CH$_2$—O— | Pr | H | H | H |
| 1-194 | 3-ClPhO— | | —CS— | —CH$_2$—O— | Pr | H | Me | H |
| 1-195 | 3-ClPhO— | | —CO— | —CH$_2$—O— | iPr | H | H | H |
| 1-196 | 3-ClPhO— | | —CS— | —CH$_2$—O— | iPr | H | H | H |
| 1-197 | 3-ClPhO— | | —CO— | —CH$_2$—O— | Me | Me | H | H |
| 1-198 | 3-ClPhO— | | —CO— | —(CH$_2$)$_2$—O— | H | H | H | H |
| 1-199 | 3-ClPhO— | | —CS— | —(CH$_2$)$_2$—O— | H | H | H | H |
| 1-200 | 3-ClPhO— | | —CO— | —(CH$_2$)$_3$—O— | H | H | H | H |
| 1-201 | 3-ClPhO— | | —(CH$_2$)$_2$— | —CH$_2$—O— | Me | H | H | H |
| 1-202 | 3-MeOPhO— | | —CO— | —CH$_2$—O— | H | H | H | H |
| 1-203 | 3-MeOPhO— | | —CS— | —CH$_2$—O— | H | H | H | H |
| 1-204 | 7-PhHpO— | H | H | —CH$_2$—O— | Me | H | H | H |
| 1-205 | PhO— | H | Me | —CH$_2$—O— | Me | H | H | H |
| 1-206 | 3-ClPhO— | H | Me | —CH$_2$—O— | Me | H | H | H |
| 1-207 | 4-PhPhO— | H | H | —CH$_2$—O— | H | H | H | H |
| 1-208 | 4-PhPhO— | | —CO— | —CH$_2$—O— | H | H | H | H |
| 1-209 | 4-PhPhO— | | —CS— | —CH$_2$—O— | H | H | H | H |

TABLE 2

| Cpd. No. | X | A | B | Y | $R^1$ | $R^2$ | $R^3$ | $R^5$ |
|---|---|---|---|---|---|---|---|---|
| 2-1 | PhO— | H | H | —CH$_2$—O— | H | H | H | H |
| 2-2 | PhO— | | —CO— | —CH$_2$—O— | H | H | H | H |
| 2-3 | 3-ClPhO— | H | H | —CH$_2$—O— | Me | H | H | H |
| 2-4 | 3-ClPhO— | | —CS— | —CH$_2$—O— | Me | H | H | —CH$_2$OAc |
| 2-5 | 3-ClBzO— | H | Me | —CH$_2$—O— | Me | H | H | H |
| 2-6 | 4-BrPhO— | | —CH$_2$SO$_2$— | —(CH$_2$)$_4$—O— | Me | Me | H | H |
| 2-7 | 3-FPhO— | | —(CH$_2$)$_2$— | —(CH$_2$)$_3$—O— | Pn | H | H | H |
| 2-8 | 4-CF$_3$PhO— | H | H | —CH$_2$—O— | Me | H | OH | —CH$_2$CO$_2$Bu |
| 2-9 | 3-NO$_2$PhO— | | —CO— | —CH$_2$—O— | H | H | H | —CH$_2$CO$_2$Bu |
| 2-10 | 3-(3-MePh)PrO— | | —CS— | —CH$_2$—O— | H | H | H | H |
| 2-11 | 3,5-diMe-4-HOBzO— | | —COCO— | —CH$_2$—O— | Me | H | Me | H |
| 2-12 | 2-(4-FPh)EtO— | | —CO— | —CH$_2$—O— | Me | H | Me | H |
| 2-13 | 3-(3,5-ditBu-4-HOPh)PrO— | H | Ac | —CH$_2$—O— | Me | H | H | H |
| 2-14 | 2-ClPhO— | H | MeCar | —CH$_2$—O— | Me | H | H | H |

TABLE 3

| Cpd. No. | X | A | B | Y | R¹ | R² | R³ | R⁵ |
|---|---|---|---|---|---|---|---|---|
| 3-1 | PhO— | H | H | —CH₂—O— | H | H | H | H |
| 3-2 | PhO— |  | —CO— | —CH₂—O— | Me | H | H | H |
| 3-3 | 3-ClPhO— |  | —CO— | —CH₂—O— | Me | H | H | H |
| 3-4 | 3-ClPhO— | Ac | Ac | —CH₂—O— | H | H | H | H |
| 3-5 | 4-HO-2,3,5-triMePhO— | H | H | —(CH₂)₂—O— | Me | Me | H | H |
| 3-6 | 3-(4-ClPh)PrO— | H | PhCar | —CH₂—O— | iBu | H | H | 2-CO₂HEt |
| 3-7 | 2,5-diMePhO— |  | —CS— | —CH₂—O— | H | H | H | H |
| 3-8 | 2,5-diMePhO— |  | —CS— | —CH₂—O— | H | H | Me | H |
| 3-9 | 4-MeOPhO— | H | Me₂NCO— | —CH₂—O— | H | H | H | H |
| 3-10 | Ph |  | —CH₂CO— | —CH₂—O— | Pn | H | H | H |
| 3-11 | PhS— | H | H | —CH₂—O— | Me | H | H | H |
| 3-12 | PhS— |  | —CO— | —CH₂—O— | H | H | H | H |
| 3-13 | Me(2-Pyr)N— | H | H | —CH₂—O— | H | H | H | H |
| 3-14 | Me(2-Pyr)N— |  | —CS— | —CH₂—O— | Me | H | H | H |

TABLE 4

| Cpd. No. | X | A | B | Y | R¹ | R² | R³ | R⁵ |
|---|---|---|---|---|---|---|---|---|
| 4-1 | PhO— | H | H | —CH₂—O— | Me | H | H | H |
| 4-2 | PhO— |  | —CO— | —CH₂—O— | H | H | H | H |
| 4-3 | PhS— |  | —CO— | —CH₂—O— | H | H | H | H |
| 4-4 | PhS— |  | —CS— | —CH₂—O— | H | H | H | H |
| 4-5 | PhS— | H | Ac | —CH₂—O— | H | H | H | H |
| 4-6 | 3-ClPhO— | H | H | —CH₂— | H | H | H | H |
| 4-7 | 3-ClPhO— | H | EtCar | —CH₂—O— | Me | Me | —OMe | —CH₂OAc |
| 4-8 | Ph |  | —SO₂— | —CH₂—O— | Me | H | H | H |
| 4-9 | 2-CF₃PhO— | H | PhO— | —CH₂—O— | H | H | H | H |
| 4-10 | 4-Me₂NPhO— |  | —COCO— | —CH₂—O— | H | H | H | H |
| 4-11 | Me(2-Pyr)N— | H | H | —CH₂—O— | H | H | H | H |
| 4-12 | Me(2-Pyr)N— |  | —CO— | —(CH₂)₂—O— | H | H | H | 2-CO₂HEt |
| 4-13 | Et(2-Pyr)N— |  | —CH₂CO— | —CH₂—O— | Me | H | Cl | H |
| 4-14 | Pn(2-Pyr)N— | H | H | —CH₂—O— | H | H | OH | H |

TABLE 5

| Cpd. No | X | A | B | Y | R¹ | R² | R³ |
|---|---|---|---|---|---|---|---|
| 5-1 | Ph |  | —CO— | —CH₂—O— | H | H | H |
| 5-2 | PhO— |  | —CS— | —CH₂—O— | H | H | H |
| 5-3 | PhO— | H | H | —(CH₂)₄—O— | Me | Me | —OiPr |
| 5-4 | 3-ClPhO— |  | —CO— | —CH₂—O— | Me | Me | H |
| 5-5 | 4-ClBzO— |  | —CO— | —CH₂—O— | Me | H | H |
| 5-6 | 2-(3-ClPh)EtO— |  | —CO— | —CH₂—O— | H | H | H |
| 5-7 | 4-HOPhS— |  | —CO— | —CH₂—O— | H | H |  |
| 5-8 | 3-CF₃PhO— |  | —CH₂CO— | —CH₂—O— | H | H | H |
| 5-9 | 3-CF₃PhO— |  | —COCO— | —CH₂—O— | Bu | H | H |
| 5-10 | Ac(2-Pyr)N— | Ac | Ac | —CH₂—O— | H | H | H |
| 5-11 | Bz(2-Pyr)N— | H | Ac | —CH₂—O— | H | H | H |
| 5-12 | Bu(2-Pyr)N— |  | —CO— | —CH₂—O— | H | H | H |
| 5-13 | Me(2-Pyr)N— |  | —CH₂SO₂— | —CH₂—O— | Bu | H | H |
| 5-14 | 3-(3,5-ditBu-4-HOPh)PrO— |  | —CO— | —(CH₂)₂—O— | H | H | H |

TABLE 6

| Cpd. No. | X | A | B | Y | R¹ | R² | R³ |
|---|---|---|---|---|---|---|---|
| 6-1 | Ph |  | —CO— | —CH₂—O— | H | H | H |
| 6-2 | PhO— |  | —CS— | —CH₂—O— | H | H | H |
| 6-3 | PhO— |  | —CS— | —CH₂—O— | H | H | Cl |
| 6-4 | PhO— |  | —(CH₂)₂— | —(CH₂)₂—O— | Me | H | H |
| 6-5 | 3-ClPhO— |  | —CO— | —CH₂—O— | H | H | H |
| 6-6 | 4-HO-2,3,5-triMePhO— |  | —CO— | —CH₂—O— | H | H | H |
| 6-7 | 4-HO-2,3,5-triMePhO— |  | —CO— | —CH₂—O— | H | H | —OMe |
| 6-8 | PhS— |  | —CO— | —CH₂—O— | H | H | H |
| 6-9 | 3-CF₃PhO— |  | —CS— | —CH₂—O— | H | H | H |

TABLE 6-continued
| Cpd. No. | X | A | B | Y | R$^1$ | R$^2$ | R$^3$ |
|---|---|---|---|---|---|---|---|
| 6-10 | Me(2-Pyr)N— | | —CO— | —CH$_2$—O— | H | H | H |
| 6-11 | Me(2-Pyr)N— | | —CS— | —CH$_2$—O— | H | H | H |
| 6-12 | Me(2-Pyr)N— | | —CS— | —(CH$_2$)$_3$—O— | Me | Me | H |
| 6-13 | 2-PyrS— | | —CO— | —CH$_2$—O— | H | H | H |
| 6-14 | 2-PyrS— | | —CO— | —CH$_2$—O— | Me | Me | H |
TABLE 7
| Cpd. No. | X | A | B | Y | R$^1$ | R$^2$ | R$^3$ | Z | |
|---|---|---|---|---|---|---|---|---|---|
| 7-1 | PhO— | H | H | —CH$_2$—O— | H | H | H | 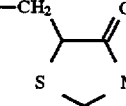 | (m-) |
| 7-2 | PhO— | | —CO— | —CH$_2$—O— | H | H | H | 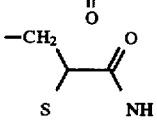 | (m-) |
| 7-3 | PhO— | | —CS— | —CH$_2$—O— | H | H | H | 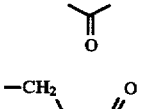 | (m-) |
| 7-4 | 3-ClPhO— | | —CO— | —CH$_2$—O— | H | H | H | 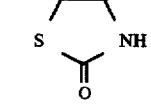 | (m-) |
| 7-5 | 3-ClPhO— | | —CO— | —CH$_2$—O— | H | H | H | 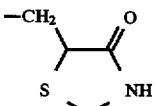 | (m-) |
| 7-6 | 3-ClPhO— | | —CO— | —CH$_2$—O— | H | H | H | 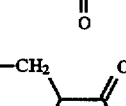 | (m-) |
| 7-7 | 3-ClPhO— | | —CO— | —CH$_2$—O— | H | H | H | 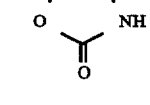 | (o-) |
| 7-8 | 3-ClPhO— | | —CO— | —CH$_2$—O— | H | H | H | 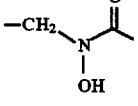 | (m-) |

TABLE 7-continued

| Cpd. No. | X | A | B | Y | R¹ | R² | R³ | Z | |
|---|---|---|---|---|---|---|---|---|---|
| 7-9 | 3-ClPhO— | | —CO— | —CH₂—O— | H | H | H | —CH₂—N(O)—C(=O)—... NH (oxazolidinedione ring) | (o-) |
| 7-10 | 3-CF₃PhO— | | —CO— | —CH₂—O— | H | H | H | —CH₂—CH(—)—C(=O)—... S, NH (thiazolidinedione ring) | (m-) |
| 7-11 | 4-PhBuO— | | —CO— | —CH₂—O— | H | H | H | —CH₂—N(OH)—C(=O)—NH₂ | (m-) |
| 7-12 | 2-(3-ClPh)EtO— | | —(CH₂)₂— | —CH₂—O— | Me | Me | Me (p-) | —CH₂—N(OH)—C(=O)—NH₂ | (m-) |
| 7-13 | Me(2-Pyr)N— | | —CO— | —(CH₂)₄—O— | H | H | H | —CH₂—N(OH)—C(=O)—NH₂ | (m-) |
| 7-14 | 2-PyrS— | | —COCO— | —CH₂—O— | H | H | H | —CH₂—N(O)—C(=O)—... NCH₂CO₂Et (oxazolidinedione ring) | (m-) |

Of the compounds listed above, we particularly prefer the following, that is to say Compounds No. 1-2, 1-4, 1-48, 1-49, 1-51, 1-64, 1-69, 1-79, 1-91, 1-92, 1-93, 1-94, 1-95, 1-128, 1-158, 1-159, 1-160, 1-161, 1-162, 1-163, 1-164, 1-165, 1-166, 1-167, 1-168, 1-169, 1-170, 1-171, 1-173, 1-176, 1-177, 1-179, 1-180, 1-181, 1-184, 1-186, 1-187, 1-188, 1-189, 1-190, 1-191, 1-192, 1-193, 1-195, 1-197, 1-200, 1-201, 1-204, 1-205, 1-206, 1-207, 1-208 and 1-209, of which Compounds No. 1-2, 1-4, 1-51, 1-64, 1-69, 1-79, 1-91, 1-93, 1-94, 1-95, 1-158, 1-159, 1-160, 1-161, 1-162, 1-164, 1-169, 1-170, 1-173, 1-177, 1-179, 1-180, 1-181, 1-186, 1-187, 1-188, 1-189, 1-190, 1-191, 1-192, 1-193, 1-195, 1-204, 1-205, 1-206 and 1-209 are more preferred. Still more preferred compounds are Compounds No. 1-2, 1-4, 1-64, 1-91, 1-93, 1-94, 1-95, 1-159, 1-161, 1-162, 1-164, 1-173, 1-179, 1-186, 1-191, 1-193, 1-195, 1-205 and 1-206.

The most preferred compounds are Compounds No.:
1-2. 5-{4-[2-(3-Phenyl-2-hydroxypropylamino)propoxy]-benzyl}thiazolidine-2,4-dione;
1-93. 5-{4-[2-(5-3'-Chlorophenoxymethyl-2-oxo-oxazolidin-3-yl)ethoxy]benzyl}thiazolidine-2,4-dione;
1-94. 5-{4-[2-(5-3'-Chlorophenoxymethyl-2-oxo-oxazolidin-3-yl)propoxy]benzyl}thiazolidine-2,4-dione;
1-95. 5-{4-[2-(5-3'-Chlorophenoxymethyl-2-thioxo-oxazolidin-3-yl)propoxy]benzyl}thiazolidine-2,4-dione;
1-162. 5-{4-[2-(3-6'-Phenylhexyloxy-2-hydroxypropyl-amino)propoxy]benzyl}thiazolidine-2,4-dione; and
1-191. 5-{4-[2-(5-3'-Chlorophenoxymethyl-2-oxo-oxazolidin- 3-yl)butoxy]benzyl}thiazolidine-2,4-dione, of which we especially prefer Compounds No. 1-2, 1-94 and 1-95.

The compounds of the present invention may be prepared by a variety of processes well known in the art for the preparation of compounds of this general type. For example they may be prepared by the following Reaction Schemes A, B, C and F:

Reaction Scheme A

This represents a general scheme that may be used to prepare any of the compounds of the present invention:

Reaction Scheme A:

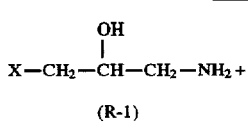

(R-1)

-continued
Reaction Scheme A:

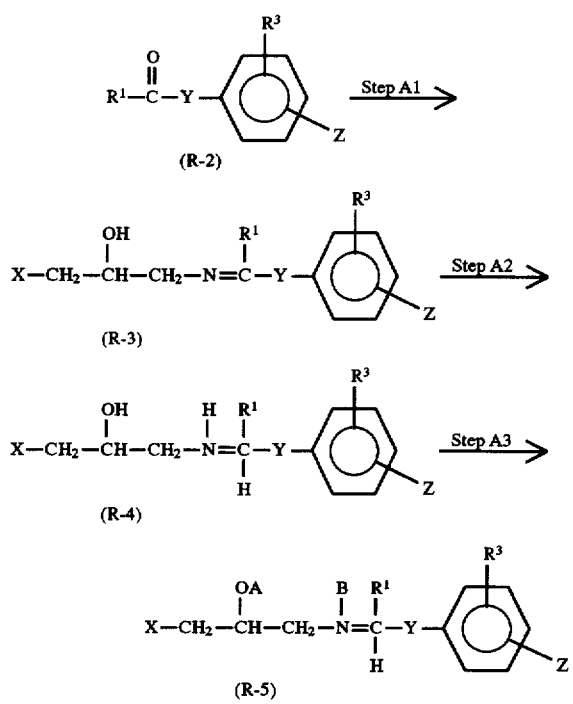

In the above formulae, X, Y, $R^1$, $R^3$, A, B and Z are as defined above).

Step A1

In Step A1, a compound of formula (R-3) is obtained by reacting an amino alcohol of formula (R-1) and a compound of formula (R-2). The compound (R-2) is a known compound and may be obtained by known methods, for example, by reacting a haloacetone and a phenol compound by a conventional method, for example as disclosed in Japanese Provisional Patent Publication (Kokai) No. Hei-6-25118).

The reaction of Step A1 may be carried out in the presence or absence of a dehydrating agent, for example: an anhydride of an alkali metal carbonate, such as anhydrous sodium carbonate or anhydrous potassium carbonate; an anhydride of an alkali metal sulfate, such as anhydrous sodium sulfate; an anhydride of an alkaline earth metal chloride, such as anhydrous calcium chloride; an anhydride of an alkaline earth metal sulfate, such as anhydrous magnesium sulfate; or a molecular sieve.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; halogenated hydrocarbons, such as chloroform, methylene chloride and carbon tetrachloride; ethers, such as diethyl ether, tetrahydrofuran and dioxane; amides, such as dimethylformamide, dimethylacetamide and hexamethylphosphoric triamide; alcohols, such as methanol and ethanol; sulfoxides, such as dimethyl sulfoxide or sulfolane; or a mixture of any two or more of these solvents.

The reaction can take place over a wide range of temperatures, and the precise reaction temperature is not critical to the invention. In general, we find it convenient to carry out the reaction at a temperature of from that of ice-cooling up to reflux temperature. The time required for the reaction may also vary widely, depending on many factors, notably the reaction temperature and the nature of the reagents and solvent employed. However, provided that the reaction is effected under the preferred conditions outlined above, a period of from 0.5 hour to 10 hours will usually suffice.

The reaction is preferably carried out in a hydrocarbon type or alcohol type solvent for a period of from 1 hour to 5 hours at a temperature which may range from that of ice-cooling to the reflux temperature. More preferably, the reaction is carried out in benzene for a period of from 1 hour to 3 hours under reflux, to effect dehydration.

Step A2

In Step A2, a compound of formula (R-4) is obtained by reducing the compound of formula (R-3).

The reaction is generally carried out by hydrogenation in the presence of a reducing agent or in the presence of a catalyst.

When the compound of formula (R-3) is hydrogenated in the presence of a reducing agent, the reducing agent may be, for example, a metal hydride, such as lithium borohydride, sodium borohydride, sodium cyanoborohydride, lithium aluminum hydride or diisopropyl aluminum hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; alcohols, such as methanol, ethanol and isopropanol; or a mixture of any two or more of these solvents.

The reaction can take place over a wide range of temperatures, and the precise reaction temperature is not critical to the invention. In general, we find it convenient to carry out the reaction at a temperature of from that of ice-cooling up to heating, for example under reflux. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

The reaction is preferably carried out in an alcohol type solvent in the presence of sodium borohydride or sodium cyanoborohydride for a period of from 1 hour to 1 day under ice-cooling or at a temperature from that of ice-cooling to 50° C.

When the compound of formula (R-3) is hydrogenated in the presence of a catalyst, examples of suitable catalysts include conventional catalytic hydrogenation catalysts, such as palladium-on-carbon and platinum oxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; amides, such as dimethylformamide and dimethylacetamide; alcohols, such as methanol, ethanol and isopropanol; organic acid esters, such as methyl acetate and ethyl acetate; or a mixture of any two or more of these solvents.

Step A3

In Step A3 a compound of formula (R-5) is obtained by alkylating, aralkylating, acylating or carbamoylating the compound of formula (R-4).

The alkylation and the aralkylation are generally carried out by reacting the compound of formula (R-4) with an alkyl halide or an aralkyl halide, or with an alkyl or aralkyl ester of an alkanesulfonic acid or with an arylsulfonic acid (e.g. methanesulfonic acid, benzenesulfonic acid or toluenesulfonic acid) in the presence or absence of an acid binding agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; sulfoxides, such as dimethyl sulfoxide; halogenated hydrocarbons, such as methylene chloride, chloroform and 1,2-dichloroethane; sulfolane; or a mixture of any two or more of these solvents.

The reaction can take place over a wide range of temperatures, and the precise reaction temperature is not critical to the invention. In general, we find it convenient to carry out the reaction at a temperature of from that of ice-cooling up to heating, for example under reflux. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

The acylation is generally carried out in the presence or absence of an acid binding agent. Suitable acylating agents include acyl halides and acid anhydrides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; sulfoxides, such as dimethyl sulfoxide; halogenated hydrocarbons, such as methylene chloride, chloroform and 1,2-dichloroethane; sulfolane; or a mixture of any two or more of these solvents.

The reaction can take place over a wide range of temperatures, and the precise reaction temperature is not critical to the invention. In general, we find it convenient to carry out the reaction at a temperature of from that of ice-cooling up to heating, for example under reflux. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

When A and B are combined to represent a group, such as >C=O, >C=S, —C(=O)—C(=O)—, —CH$_2$C(=O)—, —SO$_2$— or —CH$_2$SO$_2$—, a carbonylating agent (e.g. phosgene, diphosgene, triphosgene, carbonyl diimidazole or a chloroformic acid ester, such as ethyl chloroformate), a thiocarbonylating agent (e.g. thiophosgene or thiocarbonyl diimidazole), oxalyl chloride, a haloacetyl halide (e.g. chloroacetyl chloride or bromoacetyl bromide), sulfuryl chloride or a halomethanesulfonyl halide (e.g. chloromethanesulfonyl chloride) is preferably used as a reaction reagent.

The reaction is generally carried out in the presence or absence of an acid binding agent. When the acid binding agent is used, it may be, for example, an organic base, such as triethylamine, diisopropylethylamine or pyridine; or an inorganic base, such as sodium carbonate, sodium hydrogencarbonate, potassium carbonate or potassium hydrogencarbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; halogenated hydrocarbons, such as chloroform, methylene chloride, 1,2-dichloroethane and carbon tetrachloride; ethers, such as diethyl ether, tetrahydrofuran and dioxane; amides, such as dimethylformamide, dimethylacetamide and hexamethylphosphoric triamide; ureas, such as N,N'-dimethylimidazolidinone; sulfoxides, such as dimethyl sulfoxide; nitriles, such as acetonitrile and propionitrile; sulfolane; or a mixture of any two or more of these solvents.

The reaction will take place over a wide range of temperatures, and the precise reaction temperature chosen is not critical to the invention. In general, we find it convenient to carry out the reaction at a temperature in the range from the temperature of ice-cooling up to the reflux temperature of the reaction mixture, more preferably at the temperature of ice-cooling or at a temperature in the range of from that temperature to 50° C. The time required for the reaction may likewise vary widely, depending on many factors, notably the reaction temperature and the nature of the reagents. However, in most cases, a period of from 0.5 hour to 50 hours, more preferably from 5 hours to 50 hours, will normally suffice.

Reaction Scheme B

This provides several ways of obtaining specific compounds of the present invention, using the same starting material as in Reaction Scheme A:

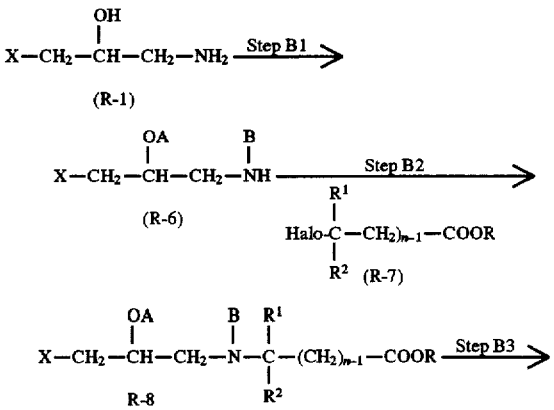

-continued
Reaction Scheme B1:
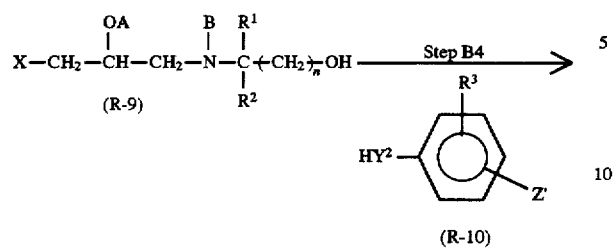
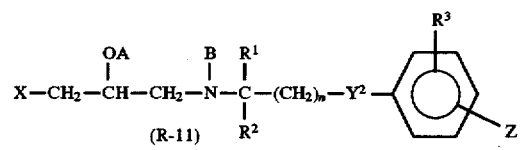
Reaction Scheme B2:
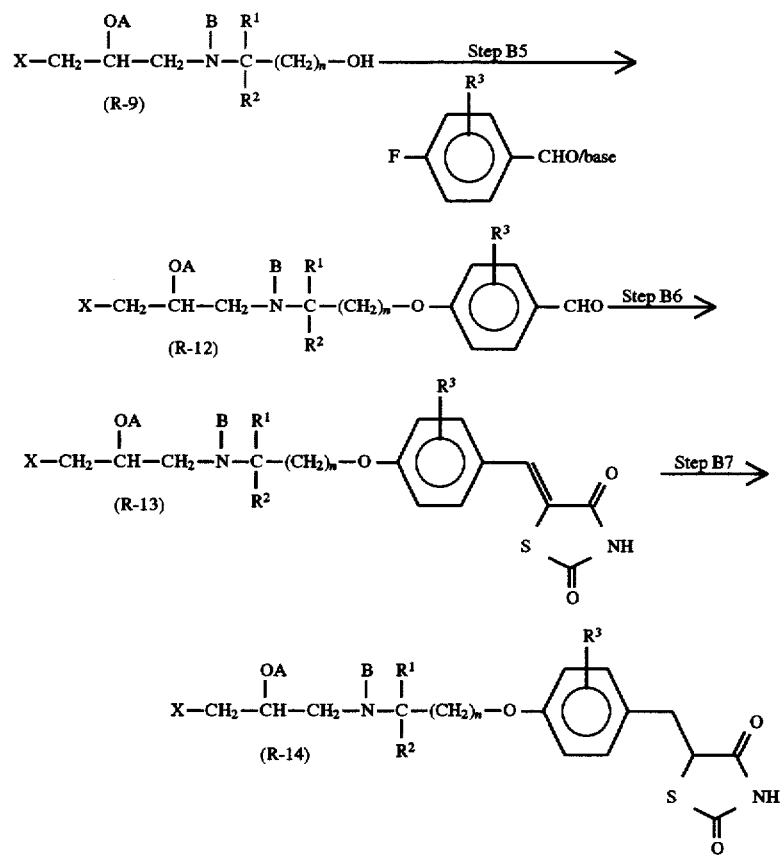
Reaction Scheme B3:
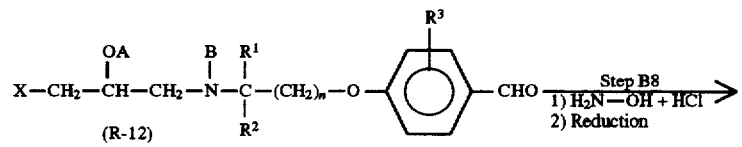

-continued
Reaction Scheme B3:

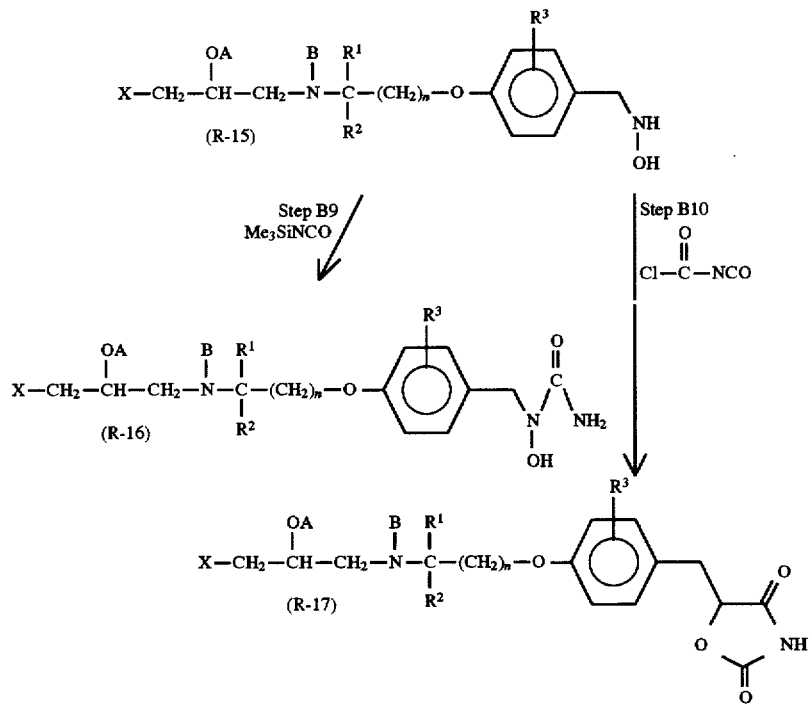

In the above formulae:

X, A, B, R$^1$, R$^2$, R$^3$, n and Z are as defined above;

R represents a straight or branched chain lower alkyl group, preferably having from 1 to 6, more preferably from 1 to 4, carbon atoms, such as those exemplified above in relation to R$^1$, especially a methyl or ethyl group;

Y$^2$ represents an oxygen atom or a sulfur atom;

Halo represents a halogen atom, such as a chlorine atom, a bromine atom or an iodine atom; and Z' represents group of formula (i), (ii), (iii) or (iv), wherein R$^5$ represents a triphenylmethyl group.

Step B1

In Step B1, a compound of formula (R-6) is obtained by alkylating, aralkylating, acylating or carbamoylating the compound of formula (R-1). This reaction is essentially the same as that described in Step A3 of Reaction Scheme A, and may be carried out under the same reaction conditions and using the same reagents.

Step B2

In Step B2, a compound of formula (R-8) is obtained by reacting the compound of formula (R-6) with a compound of formula (R-7) in the presence or absence of a base. When B represents an acyl group or a carbamoyl group, it is preferred that the compound of formula (R-6) is first contacted with a base, such as sodium hydride, and then the resulting compound is reacted with the compound of formula (R-7).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; sulfoxides, such as dimethyl sulfoxide; halogenated hydrocarbons, such as methylene chloride, chloroform and 1,2-dichloroethane; sulfolane; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating. The time required for the reaction may likewise vary widely, depending on many factors, notably the reaction temperature and the nature of the reagents. However, in most cases, a period of from 0.5 hour to several days will normally suffice.

Step B3

In Step B3, a compound of formula (R-9) is obtained by reducing the compound of formula (R-8). There is no particular restriction on the nature of the reducing agent employed, and any reducing agent commonly used in reactions of this type may equally be used here. Examples include: metal hydrides, such as sodium borohydride, lithium borohydride, lithium aluminum hydride and diisobutyl aluminum hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide: alcohols, such as methanol, ethanol and isopropanol: or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating. The time required for the reaction may likewise vary widely, depending on many factors, notably the reaction temperature and the nature of the reagents. However, in most cases, a period of from 0.5 hour to several days will normally suffice.

The reaction is preferably carried out in an alcohol type solvent in the presence of lithium borohydride for a period of from 1 hour to 1 day at a temperature which may range from room temperature to the reflux temperature of the reaction mixture.

Step B4

In Step B4, a compound of formula (R-11) is obtained by first subjecting the compound of formula (R-9) and a compound of formula (R-10) to a common Mitsunobu reaction [O. Mitsunobu, Synthesis, p. 1 (1981)] and then removing the triphenylmethyl group.

The reaction in the first stage reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; halogenated hydrocarbons, such as chloroform, methylene chloride and carbon tetrachloride; ethers, such as diethyl ether, tetrahydrofuran and dioxane; amides, such as dimethylformamide, dimethylacetamide and hexamethylphosphoric triamide; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating, more preferably at the temperature of ice-cooling or within the temperature range from that of ice-cooling to 60° C. The time required for the reaction may likewise vary widely, depending on many factors, notably the reaction temperature and the nature of the reagents. However, in most cases, a period of from several hours to several days, more preferably from 5 hours to 3 days, will normally suffice.

The second stage reaction is generally carried out by contacting the resulting compound with an acid, such as acetic acid, trifluoroacetic acid or hydrochloric acid, in the presence or absence of a solvent, or by subjecting the resulting compound to a catalytic hydrogenation reaction in a solvent.

When the reaction is carried out by contacting the resulting compound with an acid in the presence or absence of a solvent, this can be achieved by a conventional method (e.g. T. W. Green, Protective Groups in Organic Synthesis, John Wiley & Sons; and J. F. W. McOmie, Protective Groups in Organic Chemistry, Plenum Press).

When the resulting compound is subjected to a catalytic hydrogenation reaction in a solvent, any catalyst commonly used in reactions of this type may be used, for example palladium-on-carbon.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, dioxane and tetrahydrofuran; alcohols, such as methanol, ethanol and isopropanol; acids, such as formic acid, acetic acid and propionic acid; amides, such as dimethylformamide, dimethylacetamide and hexamethylphosphoric triamide; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several hours to several days, more preferably from 1 hour to 3 days, will normally suffice.

The reaction is generally carried out at atmospheric pressure or under pressure, preferably under superatmospheric pressure.

Step B5

In Step B5, a compound of formula (R-12) is obtained by reacting the compound of formula (R-9) with a 4-fluorobenzaldehyde derivative, such as 2-methoxy-4-fluorobenzaldehyde or 3-methyl-4-fluorobenzaldehyde, in the presence of a base, such as sodium hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylacetamide, dimethylformamide and hexamethylphosphoric triamide; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating, more preferably at the temperature of ice-cooling or within the temperature range from that of ice-cooling to 60° C. The time required for the reaction may likewise vary widely, depending on many factors, notably the reaction temperature and the nature of the reagents. However, in most cases, a period of from several hours to several days, more preferably from 3 hours to 3 days, will normally suffice.

Step B6

In Step B6, a compound of formula (R-13) is obtained by reacting the compound of formula (R-12) with thiazolidin-2,4-dione.

The reaction may be carried out in the presence or absence of a catalyst. When the reaction is carried out in the presence of a catalyst, examples of suitable catalysts include sodium acetate, piperidinium acetate and piperidinium benzoate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; alcohols, such as methanol, ethanol and isopropanol; amides, such as dimethylformamide, dimethylacetamide and hexamethylphosphoric triamide; halogenated hydrocarbons, such as dichloromethane, chloroform and 1,2-dichloroethane;

nitriles, such as acetonitrile and propionitrile; esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction with heating. The time required for the reaction may likewise vary widely, depending on many factors, notably the reaction temperature and the nature of the reagents. However, in most cases, a period of from several hours to several days will normally suffice.

Step B7

In Step B7, a compound of formula (R-14) is obtained by subjecting the compound of formula (R-13) to reduction, for example by a catalytic hydrogenation reaction or reduction by a metal hydride.

When the compound of formula (R-13) is subjected to a catalytic hydrogenation reaction, any catalyst commonly used in reactions of this type may be used, for example palladium-on-carbon.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, dioxane and tetrahydrofuran; alcohols, such as methanol, ethanol and isopropanol; acids, such as formic acid, acetic acid and propionic acid; amides, such as dimethylformamide, dimethylacetamide and hexamethylphosphoric triamide; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several hours to several days, more preferably from 1 hour to 3 days, will normally suffice.

The reaction is generally carried out at atmospheric pressure or under pressure, preferably under superatmospheric pressure.

When the compound of formula (R-13) is subjected to reduction by a metal hydride, the reaction can be carried out by a method disclosed in WO 93/1309.

Step B8

In Step B8, a compound of formula (R-15) is obtained by reacting the compound of formula (R-12) with hydroxylamine, followed by reduction.

The reaction of the compound of formula (R-12) with hydroxylamine (hydrochloride) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; alcohols, such as methanol, ethanol and isopropanol; amides, such as dimethylformamide, dimethylacetamide and hexamethylphosphoric triamide; halogenated hydrocarbons, such as dichloromethane, chloroform and 1,2-dichloroethane; nitriles, such as acetonitrile and propionitrile; esters, such as ethyl formate and ethyl acetate; amines, such as pyridine and triethylamine; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several hours to several days, more preferably from 1 hour to 3 days, will normally suffice.

The reduction reaction to be carried out subsequently is essentially the same as that described in Step A2 of Reaction Scheme A, and may be carried out under the same reaction conditions and using the same reagents.

Step B9

In Step B9, a compound of formula (R-16) is obtained by reacting the compound of formula (R-15) with trimethylsilyl isocyanate.

The reaction is normally and preferably effected in the presence of a solvent. There is no particular restriction on the nature of the solvent to be employed, provided that it has no adverse effect on the reaction or on the reagents involved and that it can dissolve the reagents, an least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; halogenated hydrocarbons, such as dichloromethane, chloroform and 1,2-dichloroethane; nitriles, such as acetonitrile and propionitrile; esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating, more preferably at the temperature of ice-cooling or within the temperature range from that of ice-cooling to 60° C. The time required for the reaction may likewise vary widely, depending on many factors, notably the reaction temperature and the nature of the reagents. However, in most cases, a period of from several hours to several days, more preferably from 1 hour to 3 days, will normally suffice.

Step B10

In Step B10, a compound of formula (R-17) is obtained by reacting the compound of formula (R-15) with chlorocarbonyl isocyanate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; amides, such as dimethylformamide, dimethylacetamide and hexamethylphosphoric triamide; halogenated hydrocarbons, such as dichloromethane, chloroform and 1,2-dichloroethane; nitriles, such as acetonitrile and propionitrile; esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating, more preferably at the temperature of ice-cooling or within the temperature range from that of ice-cooling to 60° C. The time required for the reaction may likewise vary widely, depending on many factors, notably the reaction temperature and the nature of the reagents. However, in most cases, a period of from several tens of minutes to 1 day will normally suffice.

Reaction Scheme C

This reaction scheme provides an alternative method of preparing the compound of formula (R-9) (see Reaction Schemes B1 and B2).

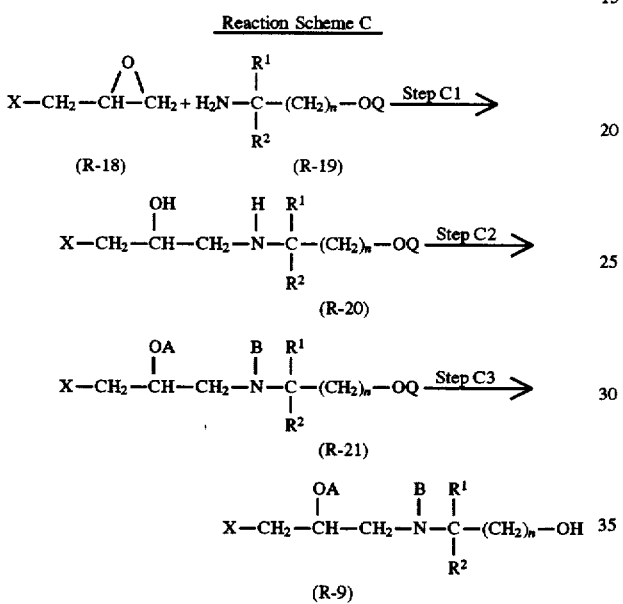

In the above formulae:

X, A, B, $R^1$ $R^2$ and n are as defined above and

Q represents a protecting group for an alcohol, for example, a t-butyldimethylsilyl group.

Step C1

In Step C1, a compound of formula (R-20) is obtained by reacting a compound of formula (R-18) and a compound of formula (R-19).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; alcohols, such as methanol, ethanol and isopropanol; amides, such as dimethylformamide, dimethylacetamide and hexamethylphosphoric triamide; halogenated hydrocarbons, such as methylene chloride, chloroform and 1,2-dichloroethane; nitriles, such as acetonitrile and propionitrile, esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction with heating, preferably at 50° C. or at the reflux temperature of the reaction mixture. The time required for the reaction may likewise vary widely, depending on many factors, notably the reaction temperature and the nature of the reagents. However, in most cases, a period of from several tens of minutes to several days will normally suffice.

Step C2

In Step C2, a compound of formula (R-21) is obtained by alkylating, aralkylating, acylating or carbamoylating the compound of formula (R-20). This reaction is essentially the same as that described in Step A3 of Reaction Scheme A, and may be carried out under the same reaction conditions and using the same reagents.

Step C3

In Step C3, the compound of formula (R-9) is obtained by removing the protecting group Q from the compound of formula (R-21).

The reaction is generally carried out by contacting the compound of formula (R-21) with an acid, such as acetic acid, trifluoroacetic acid, hydrochloric acid or hydrofluoric acid, or by contacting it with a compound generating fluoride ions, such as tributylammonium fluoride in the presence or absence of a solvent, or by subjecting it to a catalytic hydrogenation reaction in a solvent.

The reaction involving contacting the compound with an acid or a fluoride ion in the presence or absence of a solvent can be achieved by a conventional method (e.g. T. W. Green, Protective Groups in Organic Synthesis, John Wiley & Sons; and J. F. W. McOmie, Protective Groups in Organic Chemistry, Plenum Press).

When the compound of formula (R-21) is subjected to a catalytic hydrogenation reaction, any catalyst commonly used in reactions of this type may be used, for example palladium-on-carbon.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, dioxane and tetrahydrofuran; alcohols, such as methanol, ethanol and isopropanol; acids, such as formic acid, acetic acid and propionic acid; amides, such as dimethylformamide, dimethylacetamide and hexamethylphosphoric triamide; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several hours to several days, more preferably from 1 hour to 3 days, will normally suffice.

The reaction is generally carried out at atmospheric pressure or under pressure, preferably under superatmospheric pressure.

Reaction Scheme C1

The compound of formula (R-19) used in Step C1 may be prepared as shown in Reaction Scheme C1:

Reaction Scheme C1

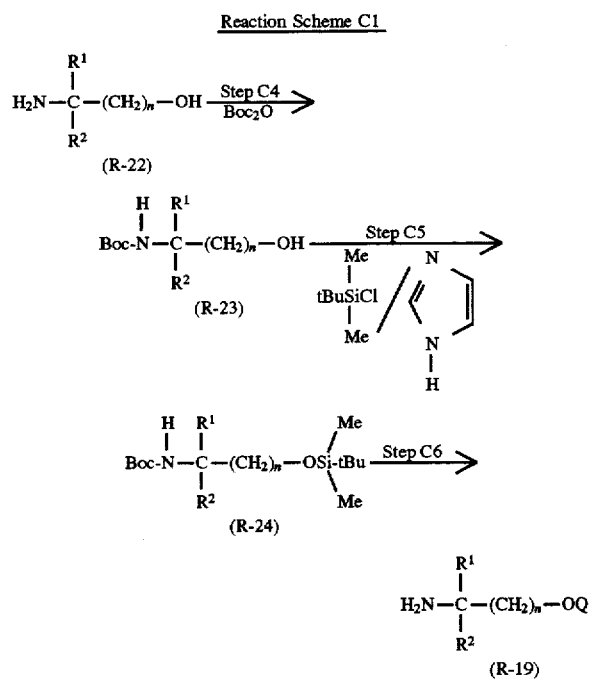

In the above formulae, $R^1$ $R^2$ and n are as defined above, and Boc represents a t-butoxycarbonyl group.

Thus, the compound of formula (R-19) can be obtained by converting the compound of formula (R-22) to an N-t-butoxycarbonylated compound of formula (R-23), followed by Q-silylation to give a compound of formula (R-24), and then eliminating the t-butoxycarbonyl group. These reactions can be carried out by conventional methods (e.g. T. W. Green, Protective Groups in Organic Synthesis, John Wiley & Sons; and J. F. W. McOmie, Protective Groups in Organic Chemistry, Plenum Press).

Reaction Scheme D

This reaction scheme illustrates a process for preparing a compound of formula (R-27), which is a compound of formula (R-6) in which A and B are combined to represent a carbonyl group, and which may then be used as described in Reaction Scheme B, above.

Reaction Scheme D

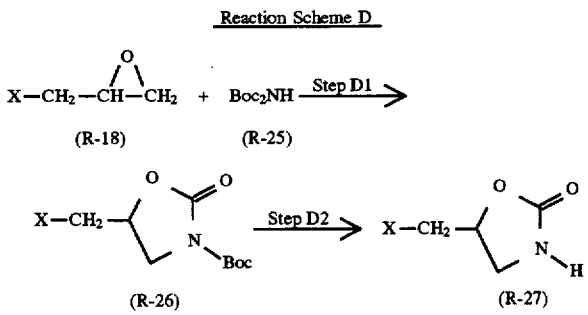

In the above formulae, X and Boc are as defined above.

Step D1

In Step D1, a compound of formula (R-26) is obtained by first reacting a compound of formula (R-25) with sodium hydride and then reacting the resulting compound with the compound of formula (R-18).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons such as benzene, toluene, xylene, hexane and heptane; ethers such as diethyl ether, tetrahydrofuran and dioxane; amides such as dimethylformamide, dimethylacetamide and hexamethylphosphoric triamide; halogenated hydrocarbons such as methylene chloride, chloroform and 1,2-dichloroethane; nitriles such as acetonitrile and propionitrile; esters such as ethyl formate and ethyl acetate; or a mixture of any two or more of these solvents. Of these, we prefer the amides.

The first stage reaction will take place over a wide range of temperatures, and the precise reaction temperature chosen is not critical to the invention. In general, we find it convenient to carry out the reaction at a temperature in the range of from that of ice-cooling up to heating. The time required for the reaction may likewise vary widely, depending on many factors, notably the reaction temperature and the nature of the reagents. However, in most cases, a period of from 0.5 hour to 5 hours will normally suffice.

The second stage reaction will take place over a wide range of temperatures, and the precise reaction temperature chosen is not critical to the invention. In general, we find it convenient to carry out the reaction at a temperature in the range of from room temperature to 100° C. The time required for the reaction may likewise vary widely, depending on many factors, notably the reaction temperature and the nature of the reagents. However, in most cases, a period of from 1 hour to several days will normally suffice.

Step D2

In Step D2, a compound of formula (R-27) is obtained by subjecting the compound of formula (R-26) to a reaction for removing the t-butoxycarbonyl group represented by Boc (e.g. as described by T. W. Green, Protective Groups in Organic Synthesis, John wiley & sons; and J. F. W. McOmie, Protective Groups in Organic Chemistry, Plenum Press).

Reaction Scheme E

This reaction scheme illustrates a method of preparing a compound (R-1), which is used as the starting material in Reaction Schemes A and B, above.

Reaction Scheme E

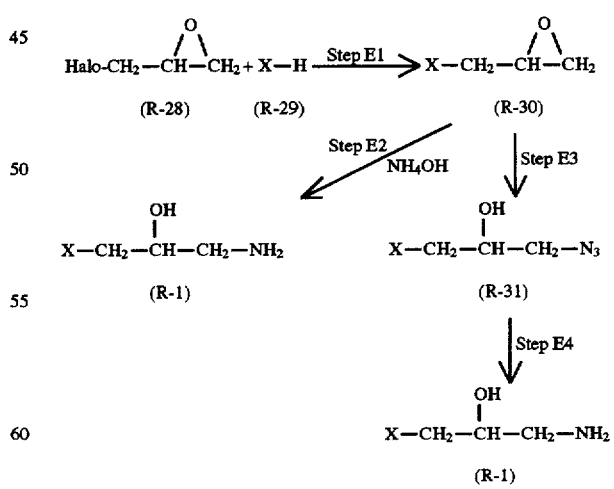

In the above formulae, X and Halo are as defined above.

Step E1

In Step E1, a compound of formula (R-30) is obtained by reacting a compound of formula (R-29) with a compound of formula (R-28). The reaction is generally carried out in the presence or absence of a base. There is no particular resrtiction on the nature of the base to be used, and any base commonly used in reactions of this type may equally be used here. Examples include: alkali metal carbonates, such as sodium carbonate and potassium carbonate; alkali metal hydrogencarbonates, such as sodium hydrogencarbonate; alkali metal hydrides, such as sodium hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; alcohols, such as methanol, ethanol and isopropanol; amides, such as dimethylformamide, dimethylacetamide and hexamethylphosphoric triamide; halogenated hydrocarbons, such as methylene chloride, chloroform and 1,2-dichloroethane; nitriles, such as acetonitrile and propionitrile; esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several tens of minutes to several days will normally suffice.

Step E2

In Step E2, the compound of formula (R-1) is obtained by reacting the compound of formula (R-30) with ammonia.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane: ethers, such as diethyl ether, tetrahydrofuran and dioxane: alcohols, such as methanol, ethanol and isopropanol: amides, such as dimethylformamide, dimethylacetamide and hexamethylphosphoric triamide: halogenated hydrocarbons, such as methylene chloride, chloroform and 1,2-dichloroethane; nitriles, such as acetonitrile and propionitrile: esters, such as methyl formate, ethyl formate and ethyl acetate; water: or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several tens of minutes to several hours will normally suffice.

The reaction may also be carried out under atmospheric pressure or in a sealed tube.

Step E3

In Step E3, a compound of formula (R-31) is obtained by reacting the compound of formula (R-30) with an alkali metal azide, for example, lithium azide, sodium azide or potassium azide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; alcohols, such as methanol, ethanol and isopropanol; amides, such as dimethylformamide, dimethylacetamide and hexamethylphosphoric triamide; halogenated hydrocarbons, such as methylene chloride, chloroform and 1,2-dichloroethane; nitriles, such as acetonitrile and propionitrile; esters, such as methyl formate, ethyl formate and ethyl acetate; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several tens of minutes to several days will normally suffice.

Step E4

In Step E4, the compound of formula (R-1) is obtained by reacting the compound of formula (R-31) with lithium aluminum hydride or by subjecting the compound of formula (R-31) to a catalytic hydrogenation reaction.

The reaction of the compound of formula (R-31) with lithium aluminum hydride is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane; or a mixture of any two or more of these solvents.

The reaction will take place over a wide range of temperatures, and the precise reaction temperature chosen is not critical to the invention. In general, we find it convenient to carry out the reaction at a temperature in the range of from that of ice-cooling up to heating. The time required for the reaction my likewise vary widely, depending on many factors, notably the reaction temperature and the nature of the reagents. However, in most cases, a period of from several tens of minutes to 1 day will normally suffice.

When the compound of formula (R-31) is hydrogenated in the presence of a catalyst, examples of suitable catalysts include conventional catalytic hydrogenation catalysts, such as palladium-on-carbon and platinum oxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane and heptane; ethers, such as diethyl ether, tetrahydrofuran and dioxane: alcohols, such as methanol, ethanol and isopropanol: amides, such as dimethylformamide, dimethylacetamide and hexamethylphosphoric triamide: halogenated hydrocarbons, such as methylene chloride, chloroform and 1,2-dichloroethane; nitriles, such as acetonitrile and propionitrile; esters, such as ethyl formate and ethyl acetate; or a mixture of any two or more of these solvents.

The reaction will take place over a wide range of temperatures, and the precise reaction temperature chosen is not critical to the invention. In general, we find it convenient to carry out the reaction at a temperature in the range of about room temperature or under heating. The time required for the reaction may likewise vary widely, depending on many factors, notably the reaction temperature and the nature of the reagents. However, in most cases, a period of from several tens of minutes to several hours will normally suffice.

The reaction is generally carried out at atmospheric pressure or under pressure, preferably under superatmospheric pressure.

Reaction Scheme F

This reaction scheme provides an alternative means of preparing compounds of formula (R-36), which are included in the compounds of formula (I) of the present invention.

In the above formulae, X,, A, B, $R^1$, $R^2$, $R^3$, $Y^2$, R, n and Halo are as defined above.

Step F1

In Step F1, a compound of formula (R-32) is obtained by reacting the compound of formula (R-9) with fluoro-4-nitrobenzene in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons such as benzene, toluene and xylene; ethers such as diethyl ether, tetrahydrofuran and dioxane; amides such as dimethylformamide, dimethylacetamide and hexamethylphosphoric triamide; or a mixture of any two or more of these solvents.

There is no particular restriction on the nature of the base to be used, provided that it has no adverse effect on the reaction, and any base commonly used in reactions of this type may equally be used here. Examples of suitable bases include: sodium hydride, potassium hydride, sodium hydroxide, potassium hydroxide, butyllithium and lithium diisopropylamide.

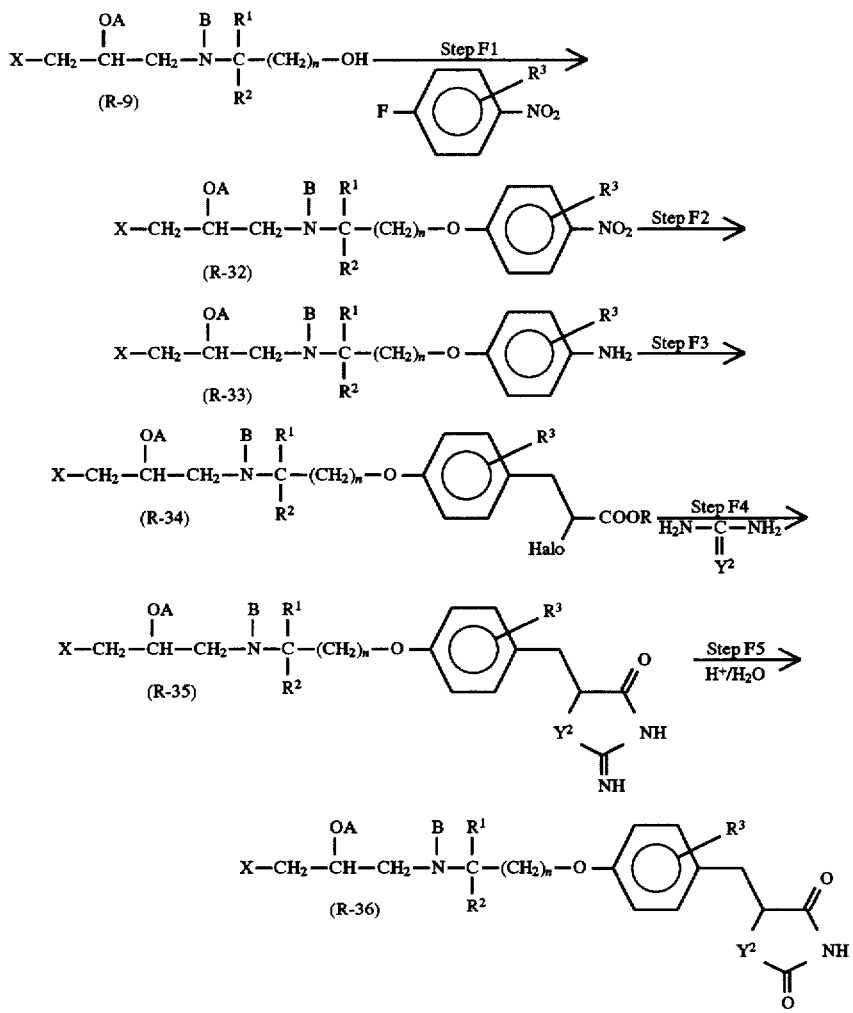

The reaction will take place over a wide range of temperatures, and the precise reaction temperature chosen is not critical to the invention. In general, we find it convenient to carry out the reaction at a temperature in the range of from that of ice-cooling up to heating. The time required for the reaction may likewise vary widely, depending on many factors, notably the reaction temperature and the nature of the reagents. However, in most cases, a period of from 1 hour to several days will normally suffice.

Step F2

In Step F2, a compound of formula (R-33) is obtained by reducing the compound of formula (R-32).

The reaction may be carried out using a conventional catalytic hydrogenation reaction or a conventional reduction process of a nitro group with zinc-acetic acid or tin-hydrochloric acid.

Step F3

In Step F3, a compound of formula (R-34) is obtained by subjecting the compound of formula (R-33) to a Meerwein arylation reaction. The reaction is generally carried out according to the method of Japanese Provisional Patent Publication (Kokai) No. Sho 55-22657 and the method of S. Oae et al. (Bull. Chem. Soc. Jpn., Vol. 53, P. 1065 (1980)).

Step F4

In Step F4, a compound of formula (R-35) is obtained by reacting the compound of formula (R-34) with a compound of formula:

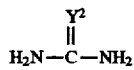

(wherein $Y^2$ represents an oxygen atom or a sulfur atom). The resulting compound of formula (R-35) can be isolated, but it can be used in Step F5 without isolation.

Step F5

In Step F5, a compound of formula (R-36) is obtained by subjecting the compound of formula (R-35) to an acid catalyzed hydrolysis reaction. Steps F4 and F5 are generally carried out according to the method described in Japanese Provisional Patent Publication (Kokai) No. Sho 55-22657.

After completion of any of the above reactions, the desired compounds obtained by the respective steps can be purified by conventional methods; suitable methods include column chromatography, recrystallization or reprecipitation or any combination thereof. For example, in one suitable recovery procedure, the reaction mixture is extracted by adding a solvent thereto, and the solvent is then evaporated from the extract. The resulting residue is applied to a chromatography column using, for example, silica gel, to obtain a pure desired compound.

BIOLOGICAL ACTIVITY

The compounds of the present invention showed excellent hypoglycemic activity in a test system using genetically diabetic animals. Accordingly, it is expected that the compounds of the invention will be useful for the treatment and/or prevention of diabetes, diabetic complications, hyperlipidemia, obesity-related hypertension, osteoporosis and the like.

The compounds of the present invention can be administered in various forms, depending on the disorder to be treated and the condition of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as a vehicle, a binder, a disintegrator, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, for the treatment of diabetes, diabetic complications and/or hyperlipemia, a daily dosage of from 0.01 to 2000 mg of the compound is recommended for an adult human patient, and this may be administered in a single dose or in divided doses.

The activity of the compounds of the present invention is illustrated by the following Experiments.

Experiment 1

Hypoglycemic Activity

The test animals used were hyperglycemic male mice of the KK strain, each having a body weight more than 40 g. Each animal was orally administered a test compound in the amount shown in the following Table 8 and then allowed to feed freely for 18 hours. At the end of this time, blood was collected from the tail veins without anesthesia. The blood glucose level (BGL) was determined by means of a glucose analyzer (GL-101, manufactured by Mitsubishi Kasei Co. or Glucoroder manufactured by Shino Test Co.).

The blood glucose lowering rate was calculated by the following equation:

$$\text{Blood glucose lowering rate } (\%) = [(BGL_s - BGL_t)/BGL_s] \times 100$$

where:

$BGL_s$ is the BGL in the group administered a solvent only, but no active compound; and $BGL_t$ is the BGL in the group administered a test compound.

The results are shown in the following Table 8, in which each compound of the present invention is identified by the number of one of the following Examples in which its preparation is illustrated.

TABLE 8

| Cpd. of Example No. | Dose (mg/kg) | Rate of lowering glucose (%) |
|---|---|---|
| 1 | 1 | 28.5 |
| 6 | 1 | 19.2 |
| 7 | 1 | 36.3 |
| 11 | 1 | 24.3 |
| 13 | 1 | 29.9 |
| 15 | 1 | 19.1 |
| 18 | 1 | 10.5 |
| 19 | 1 | 15.8 |
| 20 | 1 | 37.9 |
| 22 | 1 | 14.3 |
| 28 | 1 | 13.6 |
| 29 | 1 | 18.1 |
| 31 (less polar) | 1 | 21.6 |
| 35 | 1 | 13.5 |
| 36 (polar) | 1 | 13.7 |
| 41 | 1 | 18.2 |

TABLE 8-continued

| Cpd. of Example No. | Dose (mg/kg) | Rate of lowering glucose (%) |
|---|---|---|
| 45 (polar) | 1 | 23.9 |
| 45 (less polar) | 1 | 27.2 |
| 47 (polar) | 1 | 34.7 |
| 50 (less polar) | 1 | 17.5 |
| 51 (polar) | 1 | 20.8 |

As apparent from Table 8, the compounds of the present invention exhibited excellent activity.

Experiment 2

Inhibition of Aldose Reductase

Bovine lens aldose reductase was separated and partially purified by the method of S. Hyman and J. H. Kinoshita [J. Biol. Chem., 240, 877 (1965)] and K. Inagaki, I. Miwa and J. Okuda [Arch. Biochem. Biophys., 316, 337 (1982)], and its activity was determined photometrically by the method of Varma et al. [Biochem. Pharmac., 25, 2505 (1976)]. Inhibition of enzyme activity was measured for the compounds of the present invention at a concentration of 5 µg/ml, and the results are shown in the following Table 9.

TABLE 9

| Cpd. of Example No. | Inhibition (%) at 5 µg/ml | $IC_{50}$ (µg/ml) |
|---|---|---|
| 1 | 89.6 | 0.11 |
| 2 | 63.2 | 2.8 |
| 4 | 84.5 | 1.1 |
| 8 | 67.2 | 2.2 |
| 10 (less polar) | 60.1 | 2.0 |
| 10 (polar) | 88.3 | 0.40 |
| 16 | 59.2 | 3.3 |
| 19 | 56.1 | 3.9 |
| 20 | 69.1 | 1.8 |
| 21 | 58.7 | 2.5 |
| 22 | 70.1 | 1.7 |
| 23 | 70.7 | 1.6 |
| 24 (less polar) | 71.7 | 0.98 |
| 25 (less polar) | 57.1 | 2.0 |
| 25 (polar) | 82.0 | 0.22 |
| 26 | 74.2 | 0.55 |
| 27 | 54.9 | 1.9 |
| 30 | 68.6 | 1.8 |
| 31 (less polar) | 67.8 | 1.9 |
| 31 (polar) | 88.1 | 0.42 |
| 32 | 54.6 | 2.9 |
| 33 | 85.5 | 0.32 |
| 34 | 62.0 | 1.9 |
| 37 | 55.2 | 3.9 |
| 38 | 80.1 | 0.71 |
| 40 | 80.9 | 0.87 |
| 41 | 57.4 | 3.2 |
| 42 | 74.0 | 0.95 |
| 43 | 65.9 | 0.61 |
| 46 | 61 | 2.9 |
| 47 (less polar) | 57.6 | 1.6 |
| 47 (polar) | 86.6 | 0.23 |
| 49 | 77.8 | 0.49 |
| 50 | — | 0.32 |
| 52 | 72.8 | 0.94 |
| 53 | 77.6 | 1.1 |
| 54 | 69.1 | 1.0 |
| 55 | 62.7 | 1.4 |

Experiment 3

Toxicity

The toxicity of the compounds of the present invention was tested on male F344 rats, divided into groups of 5. The test compound was administered orally to each test animal at a dose of 50 mg/kg of body weight for 2 weeks. The test compounds used were those of Examples 20, 45 (polar, less polar) and 47 (polar). The animals were observed for 2 succesive weeks, and, during that period, they showed no abnormalities which could be attributed to the test coumpounds. In hematological examinations, they showed only a slighly decrease in red blood cell counts which could be attributed to the compound of Example 45 (less polar). In view of the substantial dose administered to each animal, the zero mortality rate indicates that the compounds of the present invention have very low toxicity.

The compounds of the present invention thus have excellent activities combined with a very low toxicity, rendering them ideally suited to therapeutic use.

The present invention is further illustrated by the following non-limiting Examples. In these Examples, the Compound Nos. given are those assigned in the foregoing Tables 1 to 7. Preparation of certain of the starting materials used in some of these Examples is illustrated by the subsequent Preparations. The specific rotation data were obtained by measurement at room temperature.

EXAMPLE 1

5-{4-[2-(5-3'-Chlorophenoxymethyl-2-Oxooxazolidin-3-yl)propoxyl]benzyl}thiazolidine-2,4-dione (Compound No. 1-94)

3 ml of trifluoroacetic acid were added, whilst ice-cooling, to 330 mg of 5-{4-[2-(5-3'-chlorophenoxy-methyl-2-oxooxazolidin-3-yl)propoxy]benzyl}-3-triphenylmethylthiazolidine-2,4-dione (prepared as described in Preparation 6), and the mixture was stirred at room temperature for 2 hours. At the end of this time, the reaction mixture was neutralized by adding an aqueous solution of sodium hydrogencarbonate and was then extracted with ethyl acetate. The extract was washed with an aqueous solution of sodium chloride and then dried over anhydrous sodium sulfate. The ethyl acetate was removed from the extract by evaporation under reduced pressure, and the resulting residue was purified by silica gel column chromatography, using a 2:3 by volume mixture of ethyl acetate and hexane as the eluent, to give 160 mg of the title compound, melting at 50.9° C. to 52.5° C. and having an Rf value of 0.45 (on silica gel thin layer chromatography, using a 2:1 by volume mixture of ethyl acetate and hexane as the developing solvent).

EXAMPLE 2

5-{4-[2-(3-3'-Chlorophenoxy-2-hydroxypropylamino)-propoxy]benzyl}thiazolidine-2,4-dione (Compound No. 1-92)

148 mg of sodium cyanoborohydride were added, whilst ice-cooling, to a solution of 100 mg of 3-(3-chloro-phenoxy)-2-hydroxypropylamine (prepared as described in Preparation 13) and 139 mg of 5-[4-(2-oxopropoxy)benzyl]-thiazolidine-2,4-dione in 3 ml of anhydrous methanol. The mixture was stirred at room temperature for 7 hours under a stream of nitrogen gas. At the end of this time, the reaction mixture was left to stand overnight, after which it was poured into water and extracted with ethyl acetate. The extract was washed with a saturated aqueous solution of sodium chloride and dried over anhydrous sodium sulfate.

The solvent was then removed from the extract by evaporation under reduced pressure, and the resulting residue was purified by silica gel thin layer chromatography (using a 8:1 by volume mixture of ethyl acetate and ethanol as the developing solvent) to give 92 mg of the title compound having an Rf value of 0.30 (on silica gel thin layer chromatography, using a 10:1 by volume mixture of ethyl acetate and ethanol as the developing solvent).

EXAMPLE 3

5-{4-[2-(3-Phenoxy-2-hydroxypropylamino) propoxy]-benzyl}thiazolidine-2,4-dione (Compound No. 1-16)

A procedure similar to that described in Example 2 was repeated, except that 0.98 g of 3-phenoxy-2-hydroxypropylamine (prepared as described in Preparation 15), 3.39 g of 5-[4-(2-oxopropoxy)benzyl]thiazolidine- 2,4-dione, 1.11 g of sodium cyanoborohydride and 60 ml of anhydrous methanol were used. The resulting crude product was purified by silica gel column chromatography (using a 10:1 by volume mixture of ethyl acetate and ethanol as the eluent) to give 1.92 g of the title compound, melting at 64° C. to 68° C.

EXAMPLE 4

5-{4-[2-(5-Phenoxymethyl-2-oxooxazolidin-3-yl)-propoxy]benzyl}thiazolidine-2,4-dione (Compound No. 1-48)

211 mg of N,N'-carbonyldiimidazole were added to a solution of 500 mg of 5-{4-[2-(3-phenoxy-2-hydroxypropylamino)propoxy]benzyl}thiazolidine-2,4-dione (prepared as described in Example 3) in 5 ml of anhydrous dimethylformamide, whilst ice-cooling, and the mixture was then stirred at room temperature for 5 hours. At the end of this time, the dimethylformamide was removed from the reaction mixture by evaporation under reduced pressure, and water was added to the resulting residue, which was then extracted with ethyl acetate. The extract was further washed with an aqueous solution of sodium chloride and dried over anhydrous sodium sulfate. The ethyl acetate was removed from the extract by evaporation under reduced pressure, and the resulting residue was purified by silica gel column chromatography, using a gradient elution method, with mixtures of ethyl acetate and hexane ranging from 1:1 to 2:1 by volume as the eluent, to give 410 mg of the title compound, melting at 54° C. to 56° C.

EXAMPLE 5

5-{4-[2-(3-3'-Chlorophenoxy-2-hydroxypropylamino)-ethoxy]benzyl}thiazolidine-2, 4-dione (Compound No. 1-91)

Following a procedure similar to that described in Example 2, 600 mg of 3-(3-chlorophenoxy)-2-hydroxypropylamine (prepared as described in Preparation 13), 800 mg of 5-[4-(2-oxoethoxy)benzyl]thiazolidine-2,4-dione (prepared as described in Preparation 20), 570 mg of sodium cyanoborohydride and 40 ml of anhydrous methanol were used, to give 180 mg of the title compound having an Rf value of 0.35 (on silica gel thin layer chromatography, using a 1:4 by volume mixture of ethanol and ethyl acetate as the developing solvent).

EXAMPLE 6

5-{4-[2-(5-3'-Chlorophenoxymethyl-2-oxooxazolidin-3-yl)ethoxy]benzyl}thiazolidine-2,4-dione (Compound No. 1-93)

Following a procedure similar to that described in Example 4, 180 mg of 5-{4-[2-(3-3'-chlorophenoxy-2-hydroxypropylamino)ethoxy]benzyl}thiazolidine-2,4-dione (prepared as described in Example 5), 65 mg of N,N'-carbonyldiimidazole and 10 ml of anhydrous dimethylformamide were used, to give 53 mg of the title compound, melting at 58° C. to 63° C. and having an Rf value of 0.27 (on silica gel thin layer chromatography, using a 2:1 by volume mixture of ethyl acetate and hexane as the developing solvent).

EXAMPLE 7

5-{4-[2-(3-Phenyl-2-hydroxypropylamino)propoxy]-benzyl}thiazolidine-2,4-dione (Compound No. 1-2)

550 mg of 3-phenyl-2-hydroxypropylamine (prepared as described in Preparation 17) and 1.0 g of 5-[4-(2-oxopropoxy)benzyl]thiazolidine-2,4-dione were suspended in 30 ml of anhydrous benzene, and the resulting suspension was heated under reflux for 30 minutes while removing water. Subsequently, the solvent was removed by evaporation under reduced pressure. The resulting oily product was dissolved in 20 ml of anhydrous methanol, 670 mg of sodium cyanoborohydride was added to the solution, whilst ice-cooling, and the mixture was stirred for 2 hours in a stream of nitrogen gas. After this, the reaction mixture was left to stand overnight, and then the solvent was removed by evaporation under reduced pressure. Water was added to the resulting residue, which was then extracted with ethyl acetate. The extract was washed with a saturated aqueous solution of sodium chloride and dried over anhydrous sodium sulfate. The solvent was removed from the extract by evaporation under reduced pressure, and the resulting residue was applied to a silica gel chromatography column, which was eluted with a 5:1 by volume mixture of ethyl acetate and ethanol, and crystallized from ethyl acetate, to give 590 mg of the title compound, melting at 145° C. to 152° C.

EXAMPLE 8

5-{4-[2-(5-Benzyl-2-oxooxazolidin-3-yl)propoxy]-benzyl}thiazolidine-2,4-dione (Compound No. 1-4)

Following a procedure similar to that described in Example 4, 300 mg of 5-{4-[2-(3-phenyl-2-hydroxypropylamino)propoxy]benzyl}thiazolidine-2,4-dione (prepared as described in Example 7), 120 mg of N,N'-carbonyldiimidazole and 10 ml of anhydrous dimethylformamide were used. The resulting crude product was applied to a silica gel chromatography column, which was then eluted with a 3:2 by volume mixture of ethyl acetate and hexane, to give 200 mg of the title compound, melting at 60° C. to 70° C.

EXAMPLE 9

5-{4-[2-(3-3'-Chlorophenoxy-2-hydroxypropylamino)-propylthio] benzyl}thiazolidine-2,4-dione (Compound No. 1-158)

Following a procedure similar to that described in Example 2, 1.0 g of 3-(3-chlorophenoxy)-2-hydroxypropylamine (prepared as described in Preparation 13), 1.5 g of 5-[4-(2-oxopropylthio)benzyl]thiazolidine-2,4-dione (prepared as described in Preparation 18), 940 mg of sodium cyanoborohydride and 30 ml of anhydrous methanol were used. The resulting crude product was applied to a silica gel chromatography column, and eluted using a 10:1 by volume mixture of ethyl acetate and ethanol, to give 1.52 g of the title compound having an Rf value of 0.44 (on silica gel thin layer chromatography, using a 10:1 by volume mixture of ethyl acetate and ethanol as the developing solvent).

EXAMPLE 10

5-{4-[2-(5-3'-Chlorolphenoxymethyl-2-oxooxazolidin-3-yl)propylthio]benzyl}thiazolidine-2,4-dione (Compound No. 1-159)

Following a procedure similar to that described in Example 4, 300 mg of 5-{4-[2-(3-3'-chlorophenoxy-2-hydroxypropylamino)propylthio]benzyl}thiazolidine-2,4-dione (prepared as described in Example 9), 470 mg of N,N'-carbonyldiimidazole and 20 ml of anhydrous dimethylformamide were used. The resulting crude product was applied to a silica gel chromatography column, and eluted using a 3:2 by volume mixture of ethyl acetate and hexane, to give a more polar diastereomer and a less polar diastereomer separately. The respective diastereomers were purified by reverse phase preparative high performance liquid chromatography [column, YMC-Pack ODS-A, a trade name for a product manufactured by YMC Co.; eluent, a 100:100:1:1 by volume mixture of acetonitrile, water, acetic acid and triethylamine], to give 110 mg of the title compound having an Rf value of 0.15 (on silica gel thin layer chromatography, using a 1:1 by volume mixture of ethyl acetate and hexane as the developing solvent) from the more polar diastereomer and 120 mg of the title compound having an Rf value of 0.25 (on silica gel thin layer chromatography, using a 1:1 by volume mixture of ethyl acetate and hexane as the developing solvent) from the less polar diastereomer.

EXAMPLE 11

5-[4-{2(R)-[5(S)-(3-Chlorophenoxymethyl)-2-oxooxazolidin-3-yl]propoxy}benzyl]thiazolidine-2,4-dione (Compound No. 1-94)

A procedure similar to that described in Example 1 was repeated, except that 0.96 g of 5-[4-{2(R)-[5(S)-(3-chlorophenoxymethyl)-2-oxooxazolidin-3-yl]propoxy}benzyl]-3-triphenylmethylthiazolidine-2,4-dione (prepared as described in Preparation 29), 4 ml of methylene chloride and 4 ml of trifluoroacetic acid were used, to give 0.52 g of the title compound having a melting point of 48° C. to 53° C. (softening) and having $[\alpha]_D$=+54.0° (methanol, c=1.000).

EXAMPLE 12

5-[4-{2(S)-[5(R)-(3-Chlorophenoxymethyl)-2-oxooxazolidin-3-yl]propoxy}benzyl]thiazolidine-2,4-dione (Compound No. 1-94)

A procedure similar to that described in Example 1 was repeated, except that 0.73 g of 5-[4-{2(S)-[5(R)-(3-chlorophenoxymethyl)-2-oxooxazolidin-3-yl]propoxy}benzyl]-3-triphenylmethylthiazolidine-2,4-dione (prepared as described in Preparation 37), 4 ml of methylene chloride and 4 ml of trifluoroacetic acid were used, to give 0.39 g of the title compound having a melting point of 55° C. to 60° C. (softening) and having $[\alpha]_D$=−52.4° (methanol, c=0.990).

EXAMPLE 13

5-[4-{2(S)-[5(S)-(3-Chlorophenoxymethyl)-2-9oxooxazolidin-3-yl]-propoxy}benzyl]thiazolidine-2,4-dione (Compound No. 1-94)

A procedure similar to that described in Example 1 was repeated, except that 286 mg of 5-[4-{2(S)-[5(S)-(3-chlorophenoxymethyl)-2-oxooxazolidin-3-yl]-propoxy}benzyl]-3-triphenylmethylthiazolidine-2,4-dione (prepared as described in Preparation 41), 1 ml of trifluoroacetic acid and 1 ml of methylene chloride were used, to give 150 mg of the title compound, melting at 54° C. to 56° C. and having $[\alpha]_D$=+41.8° (methanol, c=0.975).

EXAMPLE 14

5-[4-{2(R)-[5(R)-(3-Chlorophenoxymethyl)-2-oxooxazolidin-3-yl]propoxy}benzyl]thiazolidine-2,4-dione (Compound No. 1-94)

A procedure similar to that described in Example 1 was repeated, except that 0.57 g of 5-[4-{2(R)-[5(R)-(3-chlorophenoxymethyl)-2-oxooxazolidin-3-yl]propoxy}benzyl]-3-triphenylmethylthiazolidine-2,4-dione (prepared as described in Preparation 45), 2 ml of trifluoroacetic acid and 2 ml of methylene chloride were used, to give 280 mg of the title compound, melting at 52° C. to 53° C. and having $[\alpha]_D$=−39.7° (methanol, c=0.965).

EXAMPLE 15

5-{4-[2-(3-Benzyloxy-2-hydroxypropylamino)propoxy]-benzyl}thiazolidine-2,4-dione (Compound No. 1-64)

A procedure similar to that described in Example 2 was repeated, except that 545 mg of 3-benzyloxy-2-hydroxypropylamine (prepared as described in Preparation 48), 700 mg of 5-[4-(2-oxopropoxy)benzyl]thiazolidine-2,4-dione, 470 mg of sodium cyanoborohydride and 60 ml of anhydrous methanol were used. The resulting crude product was applied to a silica gel chromatography column, and eluted using a gradient elution method, with mixtures of ethyl acetate and ethanol in ratios ranging from 10:1 to 5:1 by volume as the eluent. The resulting product was further purified by reverse phase preparative high performance liquid chromatography [YMC-Pack ODS-A (trade name, manufactured by YMC Co.), using a 50:50:1:1 by volume mixture of acetonitrile, water, acetic acid and triethylamine as the eluent], to give 130 mg of the title compound as a pale yellow glassy solid having an Rf value of 0.16 (on silica gel thin layer chromatography, using a 10:1 by volume mixture of ethyl acetate and ethanol as the developing solvent).

EXAMPLE 16

5-{4-[2-(3-5'-Phenylpentyloxy-2-hydroxypropylamino)propoxy]benzyl}thiazolidine-2,4-dione (Compound No. 1-160).

A procedure similar to that described in Example 2 was repeated, except that 820 mg of 3-(5-phenylpentyloxy)-2-hydroxypropylamine (prepared as described in Preparation 51), 840 mg of 5-[4-(2-oxopropoxy)benzyl]-thiazolidine-2,4-dione, 540 mg of sodium cyanoborohydride and 80 ml of anhydrous methanol were used. The resulting crude product was applied to a silica gel chromatography column, and eluted using a gradient elution method, with mixtures of ethyl acetate and ethanol in ratios ranging from 10:1 to 5:1 by volume as the eluent. The resulting product was further purified by reverse phase preparative high performance liquid chromatography [YMC-Pack ODS-A (trade name, manufactured by YMC Co.), using a 50:50:1:1 by volume mixture of acetonitrile, water, acetic acid and triethylamine as the eluent], to give 250 mg of the title compound as a pale yellow oil having an Rf value of 0.35 (on silica gel thin layer chromatography, using a 5:1 by volume mixture of ethyl acetate and ethanol as the developing solvent).

EXAMPLE 17

5-{4-[2-3-3'-Phenylpropoxy-2-hydroxypropylamino)
-propoxyl]benzyl}thiazolidine-2,4-dione
(Compound No. 1-74)

A procedure similar to that described in Example 2 was repeated, except that 720 mg of 3-(3-phenylpropoxy)-2-hydroxypropylamine (prepared as described in Preparation 54), 800 mg of 5-[4-(2-oxopropoxy)benzyl]-thiazolidine-2,4-dione, 540 mg of sodium cyanoborohydride and 70 ml of anhydrous methanol were used. The resulting crude product was applied to a silica gel chromatography column, and eluted using a gradient elution method, with mixtures of ethyl acetate and ethanol in ratios ranging from 10:1 to 5:1 by volume as the eluent. The resulting product was further purified by reverse phase preparative high performance liquid chromatography [YMC-Pack ODS-A (trade name, manufactured by YMC Co.), using a 50:50:1:1 by volume mixture of acetonitrile, water, acetic acid and triethylamine as the eluent] to give 380 mg of the title compound as a pale yellow glassy solid having an Rf value of 0.29 (on silica gel thin layer chromatography, using a 5:1 by volume mixture of ethyl acetate and ethanol as the developing solvent).

EXAMPLE 18

5-{4-[2-(3-2'-Phenylethoxy-2-hydroxypropylamino)-propoxy]benzyl}thiazolidine-2,4-dione (Compound No. 1-69)

A procedure similar to that described in Example 2 was repeated, except that 0.70 g of 3-(2-phenylethoxy)-2-hydroxypropylamine (prepared as described in Preparation 57), 1.00 g of 5-[4-(2-oxopropoxy)benzyl]-thiazolidine-2,4-dione, 0.71 g of sodium cyanoborohydride and 20 ml of anhydrous methanol were used. The resulting crude product was purified by silica gel column chromatography, using ethyl acetate as the eluent, to give 0.92 g of the title compound having a melting point of 46 to 49° C. (softening).

EXAMPLE 19

5-{4-[2-(3-4'-Phenylbutoxy-2-hydroxypropylamino)-propoxy]benzyl}thiazolidine-2,4-dione (Compound No. 1-161).

A procedure similar to that described in Example 2 was repeated, except that 1.20 g of 3-(4-phenylbutoxy)-2-hydroxypropylamine (prepared as described in Preparation 60), 1.00 g of 5-[4-(2-oxopropoxy)benzyl]-thiazolidine-2,4-dione, 0.71 g of sodium cyanoborohydride and 20 ml of anhydrous methanol were used. The resulting crude product was purified by silica gel column chromatography, using an 8:1 by volume mixture of ethyl acetate and ethanol as the eluent, to give 1.34 g of the title compound having a melting point of 32 to 37° C. (softening).

EXAMPLE 20

5-{4-[2-(3-6'-Phenylhexyloxy-2-hydroxypropylamino)-propoxy]benzyl}thiazolidine-2,4-dione (Compound No. 1-162)

A procedure similar to that described in Example 2 was repeated, except that 864 mg of 3-(6-phenylhexyloxy)-2-hydroxypropylamine (prepared as described in Preparation 63), 800 mg of 5-[4-(2-oxopropoxy)benzyl]-thiazolidine-2,4-dione, 540 mg of sodium cyanoborohydride and 50 ml of anhydrous methanol were used. The resulting crude product was purified by silica gel column chromatography, using a gradient elution method, with mixtures of ethyl acetate and ethanol in ratios ranging from 1:0 to 5:1 by volume as the eluent, to give 500 mg of the title compound, as a pale yellow oil having an Rf value of 0.42 (on silica gel thin layer chromatography, using a 5:1 by volume mixture of ethyl acetate and ethanol as the developing solvent).

EXAMPLE 21

5-{4-[2-(3-8'-Phenyloctyloxy-2-hydroxypropylamino)-propoxy]benzyl}thiazolidine-2,4-dione (Compound No. 1-163)

A procedure similar to that described in Example 2 was repeated, except that 0.96 g of 3-(8-phenyloctyloxy)-2-hydroxypropylamine (prepared as described in Preparation 66), 0.80 g of 5-[4-(2-oxopropoxy)benzyl]-thiazolidine-2,4-dione, 0.54 g of sodium cyanoborohydride and 50 ml of anhydrous methanol were used. The resulting crude product was purified by silica gel column chromatography, using a gradient elution method, with mixtures of ethyl acetate and ethanol in ratios ranging from 10:1 to 5:1 by volume as the eluent, to give 360 mg of the title compound having an Rf value of 0.43 (on silica gel thin layer chromatography, using a 5:1 by volume mixture of ethyl acetate and ethanol as the developing solvent).

EXAMPLE 22

5-{4-[2-(5-Benzyloxymethyl-2-oxooxazolidin-3-yl)propoxy]benzyl}thiazolidine-2,4-dione (Compound No. 1-164)

A procedure similar to that described in Example 4 was repeated, except that 200 mg of 5-{4-[2-(3-benzyloxy-2-hydroxypropylamino)propoxy]benzyl}thiazolidine-2,4-dione (prepared as described in Example 15), 73 mg of N,N'-carbonyldiimidazole and 20 ml of anhydrous dimethylformamide were used. The resulting crude product was purified by silica gel column chromatography, using a gradient elution method, with mixtures of ethyl acetate and hexane in ratios ranging from 2:1 to 3:1 by volume as the eluent, to give 160 mg of the title compound as a pale yellow glassy solid which was a mixture of a less polar diastereomer having an Rf value of 0.49 (on silica gel thin layer chromatography, using a 3:1 by volume mixture of ethyl acetate and hexane as the developing solvent) and a polar diastereomer having an Rf value of 0.38 (on silica gel thin layer chromatography, using a 3:1 by volume mixture of ethyl acetate and hexane as the developing solvent).

EXAMPLE 23

5-{4-[2-(5-2'-Phenylethoxymethyl-2-oxooxazolidin-3-yl)propoxy]benzyl}thiazolidine-2,4-dione
(Compound No. 1-165)

A procedure similar to that described in Example 4 was repeated, except that 700 mg of 5-{4-[2-(3-2'-phenylethoxy-2-hydroxypropylamino)propoxy]benzyl}-thiazolidine-2,4-dione (prepared as described in Example 18), 250 mg of N,N'-carbonyldiimidazole and 10 ml of anhydrous dimethylformamide were used. The resulting crude product was purified by silica gel column chromatography using a 1:1 by volume mixture of hexane and ethyl acetate as the eluent, to give 650 mg of the title compound as a 1:1 mixture of a polar diastereomer having an Rf value of 0.74 (on silica gel thin layer chromatography, using ethyl acetate as the eluent) and a less polar diastereomer having an Rf value of 0.80 (on silica gel thin layer chromatography, also ethyl acetate as the eluent).

EXAMPLE 24

5-{4-[2-(5-3-Phenylpropoxymethyl-2-oxooxazolidin-3-yl)propoxy]benzyl}thiazolidine-2,4-dione (Compound No. 1-166)

A procedure similar to that described in Example 4 was repeated, except that 600 mg of 5-{4-[2-(3-3'-phenylpropoxy-2-hydroxypropylamino)propoxy]benzyl}-thiazolidine-2,4-dione (prepared as described in Example 17), 206 mg of N,N'-carbonyldiimidazole and 60 ml of anhydrous dimethylformamide were used. The resulting crude product was applied to a silica gel chromatography column, and eluted using a gradient elution method, with mixtures of ethyl acetate and hexane in ratios ranging from 1:1 to 3:2 as the eluent, to give a polar diastereomer and a less polar diastereomer separately. The respective diastereomers were purified by reverse phase preparative high performance liquid chromatography [YMC-Pack ODS-A (trade name, manufactured by YMC Co.), using a 1:1 by volume mixture of acetonitrile and water as the eluent] to give 98 mg of the title compound having an Rf value of 0.46 (on silica gel thin layer chromatography, using a 2:1 by volume mixture of ethyl acetate and hexane as the developing solvent) from the polar diastereomer and 189 mg of the title compound having an Rf value of 0.52 (on silica gel thin layer chromatography, using a 2:1 by volume mixture of ethyl acetate and hexane as the developing solvent) from the less polar diastereomer.

EXAMPLE 25

5-{4-[2-(5-4'-Phenylbutoxymethyl-2-oxooxazolidin-3-yl)propoxy]benzyl}thiazolidine-2,4-dione (Compound No. 1-79)

A procedure similar to that described in Example 4 was repeated, except that 550 mg of 5-{4-[2-(3-4'-phenylbutoxy-2-hydroxypropylamino)propoxy]benzyl}-thiazolidine-2,4-dione (prepared as described in Example 9), 180 mg of N,N'-carbonyldiimidazole and 10 ml of anhydrous dimethylformamide were used. The resulting crude product was purified by silica gel column chromatography, using a 2:1 by volume mixture of hexane and ethyl acetate as the eluent. The product was then further purified by reverse phase preparative high performance liquid chromatography [YMC-Pack ODS-A (trade name, manufactured by YMC Co.), using a 100:100:1:1 by volume mixture of acetonitrile, water, acetic acid and triethylamine as the eluent], to give a polar diastereomer and a less polar diastereomer separately. 170 mg of the title compound having an Rf value of 0.71 (on silica gel thin layer chromatography, using ethyl acetate as the developing solvent) were obtained from the polar diastereomer and 160 mg of the title compound having an Rf value of 0.79 (on silica gel thin layer chromatography, using ethyl acetate as the developing solvent) were obtained from the less polar diastereomer.

EXAMPLE 26

5-{4-[2-(5-5'-Penylpentyloxymethyl-2-oxooxazolidin-3-yl) propoxy]benzyl}thiazolidine-2,4-dione (Compound No. 1-167)

A procedure similar to that described in Example 4 was repeated, except that 600 mg of 5-{4-[2-(3-5'-phenylpentyloxy-2-hydroxypropylamino)propoxy]benzyl}-thiazolidine-2,4-dione (prepared as described in Example 16), 194.3 mg of N,N'-carbonyldiimidazole and 60 ml of anhydrous dimethylformamide were used. The resulting crude product was purified by silica gel column chromatography, using a 2:1 by volume mixture of ethyl acetate and hexane as the eluent, to give 520 mg of the title compound as a pale yellow oil, which was a mixture of a less polar diastereomer having an Rf value of 0.61 (on silica gel thin layer chromatography, using a 2:1 by volume mixture of ethyl acetate and hexane as the developing solvent) and a polar diastereomer having an Rf value of 0.52 (on silica gel thin layer chromatography, using a 2:1 by volume mixture of ethyl acetate and hexane as the developing solvent).

EXAMPLE 27

5-{4-[2-(5-6'-Phenylhexyloxymethyl-2-oxooxazolidin-3-yl)propoxy]benzyl}thiazolidine-2,4-dione (Compound No. 1-168)

A procedure similar to that described in Example 4 was repeated, except that 690 mg of 5-{4-[2-(3-6'-phenylhexyloxy)-2-hydroxypropylamino)propoxy]benzyl}-thiazolidine-2,4-dione (prepared as described in Example 20), 217 mg of N,N'-carbonyldiimidazole and 20 ml of anhydrous dimethylformamide were used. The resulting crude product was purified by silica gel column chromatography, using a gradient elution method, with mixtures of ethyl acetate and hexane in ratios ranging from 1:1 to 3:2 by volume as the eluent, to give 502 mg of the title compound as a pale yellow oil, which was a mixture of a less polar diastereomer having an Rf value of 0.63 (on silica gel thin layer chromatography, using a 3:2 by volume mixture of ethyl acetate and hexane as the developing solvent) and a polar diastereomer having an Rf value of 0.56 (on silica gel thin layer chromatography, using a 3:2 by volume mixture of ethyl acetate and hexane as the developing solvent).

EXAMPLE 28

5-{4-[2-(5-8'-Pheyloctyloxymethyl-2-oxooxazolidin-3-yl)propoxy]benzyl}thiazolidine-2,4-dione (Compound No. 1-169)

A procedure similar to that described in Example 4 was repeated, except that 660 mg of 5-{4-[2-(3-8'-phenyloctyloxy)-2-hydroxypropylamino)propoxy]benzyl}-thiazolidine-2,4-dione (prepared as described in Example 21), 197 mg of N,N'-carbonyldiimidazole and 20 ml of anhydrous dimethylformamide were used. The resulting crude product was purified by silica gel column chromatography, using a 1:1 by volume mixture of ethyl acetate and hexane as the eluent, to give 550 mg of the title compound as a mixture of a polar diastereomer and a less polar diastereomer having Rf values of 0.58 and 0.65 (on silica gel thin layer chromatography, using a 3:2 by volume mixture of ethyl acetate and hexane as the developing solvent), respectively.

EXAMPLE 29

5-{4-[2-(5-7'-Phenylheptyloxymethyl-2-oxooxazolidin-3-yl)propoxy]benzyl}thiazolidine-2,4-dione (Compound No. 1-170)

A procedure similar to that described in Example 4 was repeated, except that 590 mg of 5-{4-[2-(3-7'-phenylheptyloxy-2-hydroxypropylamino)propoxy]benzyl}- thiazolidine-2,4-dione (prepared as described in Example 56), 181 mg of N,N'-carbonyldiimidazole and 15 ml of anhydrous dimethylformamide were used. The resulting crude product was purified by silica gel column chromatography, using a 1:1 by volume mixture of ethyl acetate and hexane as the eluent, to give 383 mg of the title compound as a mixture of a polar diastereomer and a less polar diastereomer having Rf values of 0.29 and 0.37 (on silica gel thin layer chromatography, using a 1:1 by volume mixture of ethyl acetate and hexane as the developing solvent), respectively.

EXAMPLE 30

5-{4-[2-(5-3-Fluorophenoxymethyl-2-oxooxazolidin-3-yl)propoxy]benzyl}thiazolidine-2,4-dione (Compound No. 1-171)

A procedure similar to that described in Example 1 was repeated, except that 390 mg of 5-{4-[2-(5-3'-fluorophenoxymethyl)-2-oxooxazolidin-3-yl)propoxy]-benzyl}-3-triphenylmethylthiazolidine-2,4-dione (prepared as described in Preparation 74), 2 ml of trifluoroacetic acid and 2 ml of methylene chloride were used, to give 200 mg of the title compound, melting at 50° C. to 53° C.

EXAMPLE 31

5-{4-[2-(5-4'-Methoxyphenoxymethyl-2-oxooxazolidin-3-yl)propoxy]benzyl}thiazolidine-2,4-dione (Compound No. 1-173)

(a) A procedure similar to that described in Example 1 was repeated, except that 0.68 g of 5-{4-[2-(5-4'-methoxyphenoxymethyl-2-oxooxazolidin-3-yl)propoxy]benzyl}-3-triphenylmethylthiazolidine-2,4-dione (less polar isomer) obtained as described in Preparation 78(a), 2 ml of trifluoroacetic acid and 2 ml of methylene chloride were used, to give 280 mg of the title compound having a melting point of 49° C. to 52° C. from the less polar diastereomer.

(b) A procedure similar to that described in Example 1 was repeated, except that 840 mg of 5-{4-[2-(5-4'-methoxyphenoxymethyl-2-oxooxazolidin-3-yl)propoxy]benzyl}-3-triphenylmethylthiazolidine-2,4-dione (polar isomer) obtained as described in Preparation 78(b), 2 ml of trifluoroacetic acid and 2 ml of methylene chloride were used, to give 440 mg of the title compound, melting at 54° C. to 58° C. from the polar diastereomer.

EXAMPLE 32

5-{4-[2-(3-3'-Dimethylaminophenoxy-2-hydroxypropylamino)propoxy]benzyl}thiazolidine-2,4-dione (Compound No. 1-176)

A procedure similar to that described in Example 2 was repeated, except that 1.20 g of 3-(3-dimethylaminophenoxy)-2-hydroxypropylamine (prepared as described in Preparation 81), 1.81 g of 5-[4-(2-oxopropoxy)benzyl]-thiazolidine-2,4-dione, 0.96 g of sodium cyanoborohydride and 50 ml of anhydrous methanol were used. The resulting crude product was purified by silica gel column chromatography, using a 20:1 by volume mixture of ethyl acetate and ethanol as the eluent, and was recrystallized from ethanol, to give 0.74 g of the title compound, melting at 92.1° to 98° C.

EXAMPLE 33

5-{4-[2-(5-3'-Dimethylaminophenoxymethyl-2-oxooxazolidin-3-yl)propoxy]benzyl}thiazolidine-2,4-dione (Compound No. 1-177)

A procedure similar to that described in Example 4 was repeated, except that 500 mg of 5-{4-[2-(3-3'-dimethylaminophenoxy-2-hydroxypropylamino)propoxy]benzyl}thiazolidine-2,4-dione (prepared as described in Example 32), 195 mg of N,N'-carbonyldiimidazole and 5 ml of anhydrous dimethylformamide were used. The resulting crude product was purified by silica gel column chromatography, using a 2:1 by volume mixture of ethyl acetate and hexane as the eluent, to give 380 mg of the title compound, melting at 55.5° to 57.1° C.

EXAMPLE 34

5-{4-[2-(3-4'-Phenylphenoxy-2-hydroxypropylamino)-propoxy]benzyl}thiazolidine-2,4-dione (Compound No. 1-179)

A procedure similar to that described in Example 2 was repeated, except that 1.00 g of 3-(4-phenylphenoxy)-2-hydroxypropylamine (prepared as described in Preparation 84), 1.46 g of 5-[4-(2-oxopropoxy)benzyl]-thiazolidine-2,4-dione, 0.52 g of sodium cyanoborohydride and 40 ml of anhydrous methanol were used. The resulting crude product was purified by silica gel column chromatography, using a gradient elution method, with mixtures of ethyl acetate and methanol in ratios ranging from 1:0 to 10:1 by volume as the eluent. It was then further purified by reverse phase liquid chromatography (using a 1:1 by volume mixture of acetonitrile and water as the eluent) as described in Example 10, to give 174 mg of the title compound having a melting point of 76.7° to 80.3° C.

EXAMPLE 35

5-{4-[2-(5-4'-Phenylphenoxymethyl-2-oxooxazolidin-3-yl)propoxy]benzyl}thiazolidine-2,4-dione (Compound No. 1-180)

A procedure similar to that described in Example 4 was repeated, except that 500 mg of 5-{4-[2-(3-4'-phenylphenoxy-2-hydroxypropylamino)propoxy]benzyl}-thiazolidine-2,4-dione (prepared as described in Example 34), 195 mg of N,N'-carbonyldiimidazole and 10 ml of anhydrous dimethylformamide were used. The resulting crude product was purified by silica gel column chromatography, using a 3:2 by volume mixture of ethyl acetate and hexane as the eluent, to give 0.44 g of the title compound, melting at 73.1° to 75.4° C.

EXAMPLE 36

5-{4-[2-(5-4'-Phenylphenoxymethyl-2-thioxooxazolidin-3-yl)propoxy]benzyl}thiazolidine-2,4-dione (Compound No. 1-181)

218 mg of N,N'-thiocarbonyldiimidazole were added to a solution of 500 mg of 5-{4-[2-(3-4'-phenylphenoxy-2-hydroxypropylamino)propoxy]benzyl}thiazolidine-2,4-dione (prepared as described in Example 34) in 10 ml of anhydrous methylene chloride, and the mixture was stirred at room temperature for 1 hour. At the end of this time, water was added to the reaction mixture, which was then extracted with ethyl acetate. The extract was dried over anhydrous sodium sulfate, and then the ethyl acetate was removed by evaporation under reduced pressure. The resulting residue was purified by silica gel column chromatography, using a 2:3 by volume mixture of ethyl acetate and hexane as the eluent. It was then further purified by reverse phase liquid chromatography (using a 60:40 by volume mixture of acetonitrile and water as the eluent) as described in Example 10, to give 136 mg of the title compound, melting at 58.7° to 60.8° C., from a polar diastereomer and 165 mg of the title compound, melting at 177.6° to 180.3° C., from a less polar diastereomer.

EXAMPLE 37

5-{4-[2-(3-Phenylthio-2-hydroxypropylamino)-propoxy]benzyl}thiazolidine-2,4-dione (Compound No. 1-182)

A procedure similar to that described in Example 2 was repeated, except that 2.95 g of 3-phenylthio-2-hydroxypropylamine (prepared as described in Preparation 87), 3 g of 5-[4-(2-oxopropoxy)benzyl]thiazolidine-2,4-dione, 1.0 g of sodium cyanoborohydride and 100 ml of anhydrous methanol were used, to give 1.74 g of the title compound, melting at 176° C. to 177° C.

EXAMPLE 38

5-{4-[-2-(5-Phenylthiomethyl-2-oxooxazolidin-3-yl) propoxy]benzyl}thiazolidine-2,4-dione (Compound No. 1-128)

A procedure similar to that described in Example 4 was repeated, except that 1.2 g of 5-{4-[2-(3-phenylthio-2-hydroxypropylamino)propoxy]benzyl}thiazolidine-2,4-dione (prepared as described in Example 37), 0.52 g of N,N'-carbonyldiimidazole and 20 ml of anhydrous dimethylformamide were used, to give 1.15 g of the title compound as a 1:1 mixture of two kinds of diastereomers having an Rf value of 0.30 (polar) and an Rf value of 0.38 (less polar) (on silica gel thin layer chromatography, using a 1:1 by volume mixture of ethyl acetate and hexane as the developing solvent).

EXAMPLE 39

5-[4-{2-[3-(N-Methyl-N-phenylamino)-2-hydroxypropylamino]propoxy}benzyl]thiazolidine-2,4-dione (Compound No. 1-183)

A procedure similar to that described in Example 2 was repeated, except that 1.55 g of 3-(N-methyl-N-phenylamino)-2-hydroxypropylamine (prepared as described in Preparation 90), 1.6 g of 5-[4-(2-oxopropoxy)benzyl]-thiazolidine-2,4-dione, 0.4 g of sodium cyanoborohydride and 50 ml of anhydrous methanol were used, to give 1.39 g of the title compound, melting at 115° C. to 125° C.

EXAMPLE 40

5-[4-{2-[5-(N-Methyl-N-phenylaminomethyl)-2-oxooxazolidin-3-yl]propoxy}benzyl]thiazolidine-2,4-dione (Compound No. 1-184)

A procedure similar to that described in Example 4 was repeated, except that 0.9 g of 5-[4-{2-[3-(N-methyl-N-phenylamino)-2-hydroxypropylamino]propoxy}-benzyl] thiazolidine-2,4-dione (prepared as described in Example 39), 0.36 g of N,N'-carbonyldiimidazole and 20 ml of anhydrous dimethylformamide were used, to give 0.6 g of the title compound having an Rf value of 0.24 (on silica gel thin layer chromatography, using a 1:1 by volume mixture of ethyl acetate and hexane as the developing solvent).

EXAMPLE 41

5-{4-[2-(3-3'-Chlorobenzyloxy-2-hydroxypropylamino)propoxy]benzyl}thiazolidine-2,4-dione (Compound No. 1-186)

A procedure similar to that described in Example 2 was repeated, except that 3.00 g of 3-(3-chlorobenzyloxy)-2-hydroxypropylamine (purity: 57%—prepared as described in Preparation 93), 5.00 g of 5-[4-(2-oxopropoxy)benzyl] thiazolidine-2,4-dione, 2.64 g of sodium cyanoborohydride and 100 ml of anhydrous methanol were used. The resulting crude product was purified by silica gel column chromatography, using a gradient elution method, with mixtures of ethyl acetate and ethanol in ratios ranging from 10:1 to 4:1 by volume as the eluent. It was then further purified by reverse phase column chromatography (using a 3:7 by volume mixture of acetonitrile and water as the eluent), to give 302 mg of the title compound having a melting point of 52° to 53° C. (softening).

EXAMPLE 42

5-{4-[2-(5-3'-Chlorobenzylomethyl-2-oxooxazolidin-3-yl)propoxy]benzyl}thiazolidine-2,4-dione (Compound No. 1-187)

A procedure similar to that described in Example 4 was repeated, except that 300 mg of 5-{4-[2-(3-3'-chlorobenzyloxy-2-hydroxypropylamino)propoxy]benzyl}-thiazolidine-2,4-dione (prepared as described in Example 41), 115 mg of N,N'-carbonyldiimidazole and 5 ml of anhydrous dimethylformamide were used. The resulting crude product was applied to a silica gel chromatography column, and eluted using a gradient elution method, with mixtures of ethyl acetate and hexane in ratios ranging from 3:2 to 2:1 by volume as the eluent, to give 206 mg of the title compound having an Rf value of 0.25 (on silica gel thin layer chromatography, using a 2:1 by volume mixture of ethyl acetate and hexane as the developing solvent).

EXAMPLE 43

5-{4-[2-(5-3'-Chlorobenzyloxymethyl-2-thioxooxazolidin-3-yl)propoxy]benzyl}thiazolidine-2,4-dione (Compound No. 1-188)

A procedure similar to that described in Example 36 was repeated, except that 300 mg of 5-{4-[2-(3-3'-chlorobenzyloxy)-2-hydroxypropylamino)propoxy] benzyl}-thiazolidine-2,4-dione (prepared as described in Example 41), 125 mg of N,N'-thiocarbonyldiimidazole and 5 ml of anhydrous methylene chloride were used. The resulting crude product was purified by silica gel column chromatography, using a 2:3 by volume mixture of ethyl acetate and hexane as the eluent, to give 191 mg of the title compound having an Rf value of 0.35 (on silica gel thin layer chromatography, using a 2:1 by volume mixture of ethyl acetate and hexane as the developing solvent).

EXAMPLE 44

5-{4-[2-(5-3'-Chlorobenzylomethyl-2-thioxooxazolidin-3-yl)propoxyl]benzyl}thiazolidine-2,4-dione sodium salt (Compound No. 1-189)

68 mg of 5-{4-[2-(5-3'-chlorobenzyloxymethyl-2-thioxooxazolidin-3-yl)propoxy]benzyl}thiazolidine-2,4-dione (prepared as described in Example 43) were dissolved in 2 ml of methanol, and to the resulting solution was added a solution obtained by diluting 24 mg of sodium methoxide (as a 28% w/v methanol solution) with 1 ml of methanol. The mixture was then stirred at room temperature for 1 hour. At the end of this time, the solvent was removed by evaporation under reduced pressure, to give 50 mg of the title compound, melting at 238.7° to 240° C. (with decomposition).

EXAMPLE 45

5-{4-[2-5-3'-Chlorophenoxymethyl-2-thioxooxazolidin-3-yl)propoxyl]benzyl}thiazolidine-2,4-dione (Compound No. 1-95)

A procedure similar to that described in Example 36 was repeated, except that 300 mg of 5-{4-[2-(3-3'-chlorophenoxy-2-hydroxypropylamino)propoxy]benzyl}-thiazolidine-2,4-dione (prepared as described in Example 2), 127 mg of N,N'-thiocarbonyldiimidazole and 5 ml of anhydrous dimethylformamide were used. The resulting crude product was purified by silica gel column chromatography, using a 2:3 by volume mixture of ethyl acetate and hexane as the eluent. It was then further purified by reverse phase column chromatography (using a 1:1 by volume mixture of acetonitrile and water as the eluent) as described in Example 10, to give 87 mg of the title compound, melting at 50.3° to 52.8° C., from a polar diastereomer and 78 mg of the title compound, melting at 50.6° to 53.1° C., from a less polar diastereomer.

EXAMPLE 46

5-{4-[2-(3-3'-Chlorophenoxy-2-hydroxypropylamino)-butoxy]benzyl}thiazolidine-2,4-dione (Compound No. 1-190)

A procedure similar to that described in Example 2 was repeated, except that 1.50 g of 3-(3-chlorophenoxy)-2-hydroxypropylamine (prepared as described in Preparation 13), 2.61 g of 5-[4-(2-oxobutoxy)benzyl]-thiazolidine-2,4-dione (prepared as described in Preparation 95), 1.40 g of sodium cyanoborohydride and 40 ml of anhydrous methanol were used. The resulting crude product was purified by silica gel column chromatography, using a gradient elution method, with mixtures of ethyl acetate and ethanol in ratios ranging from 1:0 to 10:1 by volume as the eluent. It was then further purified by reverse phase column chromatography (using a 3:7 by volume mixture of acetonitrile and water as the eluent) as described in Example 10, to give 2.97 g of the title compound having a melting point of 49.5° to 52.8° C. (softening).

EXAMPLE 47

5-{4-[2-(5-3'-Chlorophenoxymethyl-2-oxooxazolidin-3-yl)butoxy]benzyl}thiazolidine-2,4-dione (Compound No. 1-191)

A procedure similar to that described in Example 4 was repeated, except that 5.48 g of 5-{4-[2-(3-3'-chlorophenoxy-2-hydroxypropylamino)butoxy]benzyl}-thiazolidine-2,4-dione (prepared as described in Example 46), 2.11 g of N,N'-carbonyldiimidazole and 60 ml of anhydrous dimethylformamide were used. The resulting crude product was purified by silica gel column chromatography, using a gradient elution method, with mixtures of ethyl acetate and hexane in ratios ranging from 2:3 to 2:1 by volume as the eluent. It was then further purified by reverse phase column chromatography (using a 9:11 by volume mixture of acetonitrile and water as the eluent) as described in Example 10, to give 1.91 g of the title compound, melting at 150.5° to 154.4° C., from a polar diastereomer and 1.90 g of the title compound having a melting point of 54.4° to 55.4° C. (softening) from a less polar diastereomer.

EXAMPLE 48

5-{4-[2-(5-3'-Chlorophenoxymethyl-2-thioxooxazolidin-3-yl)butoxy]benzyl}thiazolidine-2,4-dione (Compound No. 1-192)

A procedure similar to that described in Example 36 was repeated, except that 250 mg of 5-{4-[2-(3-3'-chlorophenoxy)-2-hydroxypropylamino)butoxy]benzyl}-thiazolidine-2,4-dione (prepared as described in Example 46), 102 mg of N,N'-thiocarbonyldiimidazole and 5 ml of methylene chloride were used. The resulting crude product was applied to a silica gel chromatography column, and was eluted using a 2:3 by volume mixture of ethyl acetate and hexane as the eluent. It was then further purified by reverse phase column chromatography (using a 1:1 by volume mixture of acetonitrile and water as the eluent) as described in Example 10, to give 87 mg of the title compound, melting at 54.1° to 56.0° C., from a polar diastereomer and 85 mg of the title compound, melting at 57.7° to 59.0° C., from a less polar diastereomer.

EXAMPLE 49

5-{4-[2-(5-Phenoxymethyl-2-thioxooxaolidin-3-yl)-propoxy]benzyl}thiazolidine-2,4-dione (Compound No. 1-51)

A procedure similar to that described in Example 36 was repeated, except that 205 mg of 5-{4-[2-(3-phenoxy-2-hydroxypropylamino)propoxy]benzyl}thiazolidine-2,4-dione (prepared as described in Example 3), 95 mg of N,N'-thiocarbonyldiimidazole and 5 ml of anhydrous dimethylformamide were used. The resulting crude product was purified by silica gel column chromatography, using a 1:1 by volume mixture of hexane and ethyl acetate as the eluent, to give 190 mg of the title compound having a melting point of 53° C. to 58° C. (softening).

EXAMPLE 50

5-{4-[2-(5-3'-Chlorophenoxymethyl-2-oxooxazolidin-3-yl)pentyloxy]benzyl}thiazolidine-2,4-dione (Compound No. 1-193)

(a) A procedure similar to that described in Example 1 was repeated, except that 1.58 g of 5-{4-[2-(5-3'-chlorophenoxymethyl-2-oxooxazolidin-3-yl)pentyloxy]benzyl}-3-triphenylmethylthiazolidine-2,4-dione (less polar isomer) obtained as described in Preparation 100, 2 ml of trifluoroacetic acid and 4 ml of methylene chloride were used, to give 516 mg of the title compound, melting at 50° C. to 52° C. from the less polar diastereomer.

(b) A procedure similar to that described in Example 1 was repeated, except that 1.45 g of 5-{4-[2-(5-3'-chlorophenoxymethyl-2-oxooxazolidin-3-yl)pentyloxy]benzyl}-3-triphenylmethylthiazolidine-2,4-dione (polar isomer) obtained as described in Preparation 100, 2 ml of trifluoroacetic acid and 4 ml of methylene chloride were used, to give 314 mg of the title compound, melting at 53° C. to 55° C. from the polar diastereomer.

EXAMPLE 51

5-{4-[2-(5-3'-Chlorophenoxymethyl-2-oxooxazolidin-3-yl)-3-methylbutoxy]benzyl}thiazolidine-2,4-dione (Compound No. 1-195)

(a) A procedure similar to that described in Example 1 was repeated, except that 0.92 g of 5-{4-[2-(5-3'-chlorophenoxymethyl-2-oxooxazolidin-3-yl)-3-methylbutoxy]benzyl}-3-triphenylmethyl-thiazolidine-2,4-dione (less polar isomer) [obtained as described in Preparation 101(a)], 2 ml of trifluoroacetic acid and 4 ml of methylene chloride were used, to give 145 mg of the title compound, melting at 51° C. to 53° C., from the less polar diastereomer.

(b) A procedure similar to that described in Example 1 was repeated, except that 1.18 g of 5-{4-[2-(5-3'-chlorophenoxymethyl-2-oxooxazolidin-3-yl)-3-methylbutoxy]benzyl}-3-triphenylmethyl-thiazolidine-2,4-dione (polar isomer) [obtained as described in Preparation 101(b)], 2 ml of trifluoroacetic acid and 4 ml of methylene chloride were used, to give 177 mg of the title compound, melting at 57° C. to 58° C., from the polar diastereomer.

EXAMPLE 52

5-{4-[2-(5-3'-Chlorophenoxymethyl-2-oxooxazolidin-3-yl)-2-methylpropoxy]benzyl}thiazolidine-2,4-dione (Compound No. 1-197)

4 ml of methanol were added to 1.50 g of a mixture of 5-{4-[2-(5-3'-chlorophenoxymethyl-2-oxooxazolidin-3-yl)-2-methylpropoxy]benzyl}-2-iminothiazolidin-4-one and thiourea [obtained as described in Preparation 111] and 15 ml of 6N aqueous hydrochloric acid, and the mixture was heated under reflux for 5 hours. At the end of this time, the reaction mixture was neutralized by adding an aqueous solution of sodium hydrogencarbonate, and the mixture was extracted with ethyl acetate. The extract was washed with an aqueous solution of sodium chloride and dried over anhydrous sodium sulfate. The ethyl acetate was removed from the extract by evaporation under reduced pressure, and the resulting residue was applied to a silica gel chromatography column, and eluted using a 1:1 by volume mixture of ethyl acetate and hexane as the eluent. It was then further purified by reverse phase preparative high performance liquid chromatography [YMC-Pack ODS-A (trade name, manufactured by YMC Co.), using a 1:1 by volume mixture of acetonitrile and water as the eluent), to give 454 mg of the title compound, melting at 55° C. to 58° C.

EXAMPLE 53

5-{4-[3-Phenoxymethyl-2-oxooxazolidin-3-yl)-propoxy]benzyl}thiazolidine-2,4-dione (Compound No. 1-49)

A procedure similar to that described in Example 1 was repeated, except that 1.98 g of 5-{4-[3-(5-phenoxymethyl-2-oxooxazolidin-3-yl)propoxy]benzyl}-3-triphenylmethylthiazolidine-2,4-dione (prepared as described in Preparation 115), 2 ml of trifluoroacetic acid and 4 ml of methylene chloride were used, to give 1.18 g of the title compound, melting at 41° C. to 43° C.

EXAMPLE 54

5-{4-[4-(5-3'-Chlorophenoxymethyl-2-oxooxazolidin-3-yl)butoxy]benzyl}thiazolidine-2,4-dione (Compound No. 1-200)

A procedure similar to that described in Example 1 was repeated, except that 1.42 g of 5-{4-[4-(5-3'-chlorophenoxymethyl-2-oxooxazolidin-3-yl)butoxy]benzyl}-3-triphenylmethylthiazolidine-2,4-dione (prepared as described in Preparation 118), 2 ml of trifluoroacetic acid and 4 ml of methylene chloride were used, to give 910 mg of the title compound, melting at 40° C. to 42° C.

EXAMPLE 55

5-{4-[2-(2-3'-Chlorophenoxymethylmorpholino)-propoxy]benzyl}thiazolidine-2,4-dione (Compound No. 1-201)

A procedure similar to that described in Example 1 was repeated, except that 1.24 g of 5-{4-[2-(2-3'-chlorophenoxymethylmorpholino)propoxy]benzyl}-3-triphenylmethylthiazolidine-2,4-dione (prepared as described in Preparation 122), 4 ml of trifluoroacetic acid and 2 ml of methylene chloride were used, to give 181 mg of the title compound, melting at 51° C. to 52° C.

EXAMPLE 56

5-{4-[2-(3-7'-Phenylheptyloxy-2-hydroxypropylamino)-propoxy]benzyl}thiazolidine-2,4-dione (Compound No. 1-204)

A procedure similar to that described in Example 2 was repeated, except that 836 mg of 3-(7-phenylheptyloxy)-2-hydroxypropylamine (prepared as described in Preparation 69), 800 mg of 5-[4-(2-oxopropoxy)benzyl]-thiazolidine-2,4-dione, 540 mg of sodium cyanoborohydride and 50 ml of anhydrous methanol were used, to give 74 mg of the title compound having an Rf value of 0.21 (on silica gel thin layer chromatography, using a 5:1 by volume mixture of ethyl acetate and ethanol as the developing solvent).

EXAMPLE 57

5-[4-{2-[N-(3-3'-Chlorophenoxy-2-hydroxypropyl)-N-methylamino]propoxy}benzyl]thiazolidine-2,4-dione (Compound No. 1-206)

180 mg of paraformaldehyde and 30 mg of p-toluenesulfonic acid were added to 300 mg of 5-{4-[2-(3-3'-chlorophenoxy-2-hydroxypropylamino)propoxy]benzyl}-thiazolidine-2,4-dione (prepared as described in Example 2) in 20 ml of a 1:1 by volume mixture of toluene and dioxane, and the mixture was heated under reflux for 3 hours. The mixture was then stirred for 2 days, after which a further 180 mg of paraformaldehyde and 30 mg of p-toluenesulfonic acid were added, and the mixture was heated under reflux for 8 hours. At the end of this time, the solvent was removed from the reaction mixture by evaporation under reduced pressure. An aqueous solution of sodium hydrogencarbonate was added to the residue, and the mixture was extracted with ethyl acetate. The extract was washed with a saturated aqueous solution of sodium chloride and dried over anhydrous sodium sulfate. The ethyl acetate was removed from the extract by evaporation under reduced pressure, and the resulting residue was purified by reverse phase preparative high performance liquid chromatography [YMC-Pack ODS-A (trade name, manufactured by YMC Co.), using a 1:1 by volume mixture of acetonitrile and water as the eluent), to give 78 mg of the title compound having a melting point of 64° C. to 67° C. (softening).

EXAMPLE 58

5-{4-[2-(3-4'-phenylphenoxy-2-hydroxypropylamino)-ethoxy]benzyl}thiazolidine-2,4-dione (Compound No. 1-207)

A procedure similar to that described in Example 2 was repeated, except that 0.42 g of 3-(4-phenylphenoxy)-2-hydroxypropylamine, 10 ml of absolute methanol, 0.21 g of sodium cyanoborohydride and 0.52 g of 5-[4-(2-oxoethoxy)benzyl]thiazolidine-2,4-dione were used, to give a crude product, which was then purified by silica gel column chromatography using a gradient elution method, with mixtures of ethyl acetate and methanol in ratios ranging from 1:0 to 3:1 by volume as the eluent, and subsequent reverse preparative high performance liquid chromatography [YMC-Pack ODS-A (trade name), using a mixture of acetonitrile and water ranging from 3:7 to 7:13 by volume as the eluent], to give 222 mg of the title compound melting at 83° C. to 86° C.

EXAMPLE 59

5-{4-[2-(5-4'-phenylphenoxymethyl-2-thioxooxazolidin-3-yl)ethoxy]benzyl}thiazolidine-2,4-dione (Compound No. 1-209)

A procedure similar to that described in Example 4 was repeated, except that 50 mg of 5-{4-[2-(3-4'-phenylphenoxy-2-hydroxypropylamino)ethoxy]benzyl}-thiazolidine-2,4-dione, 1 ml of anhydrous methylene chloride and 22 mg of N,N'-thiocarbonyldiimidazole were used, to give a crude product which was then purified by reverse preparative high performance liquid chromatography [YMC-Pack ODS-A, using a mixture of acetonitrile and water ranging from 1:1 to 11:9 by volume], to give 42 mg of the title compound melting at 68° C. to 70° C.

PREPARATION 1

3-Chlorophenoxymethyloxirane 50 ml of a solution of 40.96 g of epibromohydrin in anhydrous dimethylformamide were added dropwise to a mixture of 35.70 g of 3-chlorophenol, 47.67 g of potassium carbonate and 200 ml of anhydrous dimethylformamide, and the mixture was heated at 62° C. for 3.5 hours. At the end of this time, the dimethylformamide was removed from the reaction mixture by evaporation under reduced pressure, and water was added to the resulting residue, which was then extracted with ethyl acetate. The extract was then washed with an aqueous solution of sodium chloride and dried over anhydrous sodium sulfate. The ethyl acetate was removed from the extract by evaporation under reduced pressure, and the resulting residue was purified by silica gel column chromatography, using a 1:4 by volume mixture of ethyl acetate and hexane as the eluent, to give 43.43 g of the title compound having an Rf value of 0.45 (on silica gel thin layer chromatography, using a 1:4 by volume mixture of ethyl acetate and hexane as the developing solvent).

PREPARATION 2

5-(3-Chlorophenoxymethyl)-3-t-butoxycarbonyloxazolidin-2-one 2.18 g of sodium hydride (as a 55% by weight dispersion in mineral oil) were washed with hexane, 50 ml of dimethylformamide were added, and then a solution of 13.3 g of di-t-butyliminodicarboxylate in 60 ml of dimethylformamide was added dropwise to the mixture, whilst ice-cooling. When this addition was complete, a further 50 ml of dimethylformamide was added to the mixture. The reaction mixture was then stirred at the same temperature for 1 hour after which it was stirred at room temperature for 2 hours. At the end of this time, 350 ml of dimethylformamide and then 9.2 g of 3-chlorophenoxymethyloxirane (prepared as described in Preparation 1) were added to the reaction mixture. The mixture was then stirred for 2 days at room temperature, after which it was heated at 70° C. for 3 hours. At the end of this time, the reaction mixture was adjusted to a pH value of 4 by adding 2N aqueous hydrochloric acid, whilst ice-cooling. The solvent was then removed from the reaction mixture by evaporation under reduced pressure, and water was added to the residue, which was then extracted with ethyl acetate. The extract was washed with an aqueous solution of sodium chloride and dried over anhydrous sodium sulfate. The ethyl acetate was then removed from the extract by evaporation under reduced pressure, and the resulting residue was purified by silica gel column chromatography, using a gradient elution method, with mixtures of ethyl acetate and hexane ranging from 1:3 to 3:1 by volume as the eluent, to give 9.80 g of the title compound, melting at 116.2° C. to 124.0° C.

PREPARATION 3

5-(3-Chlorophenoxymethyl)oxazolidin-2-one 4 ml of trifluoroacetic acid were added, whilst ice-cooling, to a solution of 1.97 g of 5-(3-chlorophenoxymethyl)-3-t-butoxycarbonyloxazolidin-2-one (prepared as described in Preparation 2) in 4 ml of anhydrous tetrahydrofuran, and the mixture was stirred at room temperature for 1 hour. At the end of this time, the tetrahydrofuran and trifluoroacetic acid were removed from the reaction mixture by evaporation under reduced pressure, to give 1.23 g of the title compound having an Rf value of 0.43 (on silica gel thin layer chromatography, using ethyl acetate as the developing solvent).

PREPARATION 4

Ethyl 2-[5-(3-chlorophenoxymethyl)-2-oxooxazolidin-3-yl]propionate 0.17 g of sodium hydride (as a 55% by weight dispersion in mineral oil) was washed with hexane, and then 15 ml of dimethylformamide were added. A solution of 1.85 g of 5-(3-chlorophenoxymethyl)oxazolidin-2-one (prepared as described in Preparation 3) in 10 ml of dimethylformamide was added dropwise to the mixture, whilst ice-cooling, and then a further 50 ml of dimethylformamide was added to the mixture. The resulting mixture was stirred at room temperature for 2 hours. Subsequently, a solution of 1.76 g of ethyl 2-bromopropionate in 5 ml of dimethylformamide was added to the reaction mixture, whilst ice-cooling, and the mixture was stirred at room temperature for 1 hour. At the end of this time, the dimethylformamide was removed from the reaction mixture by evaporation under reduced pressure, and water was added to the resulting residue, which was then extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a 1:1 by volume mixture of ethyl acetate and hexane as the eluent, to give 1.05 g of the title compound having an Rf value of 0.38 (on silica gel thin layer chromatography, using a 1:1 by volume mixture of ethyl acetate and hexane as the developing solvent).

PREPARATION 5

2-[5-(3-Chlorophenoxymethyl)-2-oxooxazolidin-3-yl]propanol (a) 0.4 g of lithium borohydride was added, whilst ice-cooling, to a solution of 2.95 g of ethyl 2-[5-(3-chlorophenoxymethyl)-2-oxooxazolidin-3-yl]propionate (prepared as described in Preparation 4) in 25 ml of tetrahydrofuran, and then a mixture of 0.37 ml of methanol and 5 ml of tetrahydrofuran was added dropwise to the resulting mixture. The reaction mixture was then stirred at room temperature for 2 hours. At the end of this time, the tetrahydrofuran was removed from the reaction mixture by evaporation under reduced pressure, and an aqueous solution of sodium chloride was added to the resulting residue, which was then extracted with ethyl acetate. The extract was dried over anhydrous sodium sulfate. The ethyl acetate was then removed from the extract by evaporation under reduced pressure, and the resulting residue was recrystallized from ethyl acetate, to give 0.93 g of the title compound, melting at 114° C. to 115° C.

(b) 1.2 ml of a 26% w/v solution of tetrabutyl ammonium fluoride in tetrahydrofuran were added, whilst ice-cooling, to a solution of 152 mg of 3-(2-t-butyldimethylsilyloxy-1-methylethyl)-5-(3-chlorophenoxymethyl)oxazolidin-2-one (prepared as described in Preparation 11) in 1 ml of anhydrous tetrahydrofuran, and the mixture was stirred at room temperature for 1.5 hours. At the end of this time, a saturated aqueous solution of sodium chloride was added to the reaction mixture, and the mixture was extracted with ethyl acetate. The extract was dried over anhydrous sodium sulfate. The ethyl acetate was removed from the extract by evaporation under reduced pressure, and the resulting residue was purified by silica gel column chromatography, using a gradient elution method, with mixtures of ethyl acetate and ethanol ranging from 1:0 to 20:1 by volume as the eluent, to give 97 mg of the title compound, whose physico-chemical properties were the same as those of the product of Preparation 5(a).

PREPARATION 6

5-{4-[2-(5-3'-Chlorophenoxymethyl-2-oxooxazolidin-3-yl)propoxy]benzyl}-3-triphenylmethylthiazolidine-2,4-dione A mixture of 344 mg of tributylphosphine, 15 ml of anhydrous benzene, 654 mg of 5-(4-hydroxybenzyl)-3-triphenylmethylthiazolidine-2,4-dione and 429 mg of azodicarbonyldipiperidine was stirred at room temperature for 30 minutes. Subsequently, a solution of 500 mg of 2-[5-(3-chlorophenoxymethyl)-2-oxooxazolidin-3-yl]propanol (prepared as described in Preparation 5) in 10 ml of benzene was added to the mixture, which was then stirred overnight. At the end of this time, the solvent was removed from the reaction mixture by distillation under reduced pressure, and insolubles were removed by filtration. The resulting filtrate was evaporated to dryness under reduced pressure, and the resulting residue was purified by silica gel column chromatography, using a 2:3 by volume mixture of ethyl acetate and hexane as the eluent, to give 0.33 g of the title compound, melting at 90.9° C. to 94.0° C.

PREPARATION 7

2-Benzyloxycarbonylaminopropanol 31.3 ml of triethylamine were added to a solution of 16.9 g of DL-alaninol in 100 ml of anhydrous tetrahydrofuran, after which 100 g of benzyloxycarbonyl chloride (as a 30% to 35% w/v solution in toluene) were added dropwise, whilst ice-cooling. The reaction mixture was then stirred at room temperature overnight. At the end of this time, the tetrahydrofuran was removed from the reaction mixture by evaporation under reduced pressure, and water was added to the resulting residue, which was then extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a 2:1 by volume mixture of ethyl acetate and hexane as the eluent, to give 18.07 g of the title compound, melting at 52.2° C. to 56.6° C.

PREPARATION 8

Benzyl N-(2-t-Butyldimethylsilyloxy-1-methylethyl)-carbamate

A solution of 13.72 g of t-butyldimethylsilyl chloride in 50 ml of dimethylformamide was added dropwise, whilst ice-cooling, to a mixture of 16.0 g of 2-benzyloxycarbonylaminopropanol (prepared as described in Preparation 7), 12.39 g of imidazole and 150 ml of dimethylformamide. The mixture was then stirred at room temperature for 6.5 hours. At the end of this time, the dimethylformamide was removed from the reaction mixture by evaporation under reduced pressure, and water was added to the resulting residue, which was then extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a 1:6 by volume mixture of ethyl acetate and hexane as the eluent, to give 23.89 g of the title compound, melting at 68.0° C. to 70.2° C.

PREPARATION 9

2-t-Butyldimethylsilyloxy-1-methylethylamine

Hydrogen was introduced into a mixture of 4.0 g of benzyl N-(2-t-butyldimethylsilyloxy-1-methylethyl)-carbamate (prepared as described in Preparation 8), 0.80 g of 10% w/w palladium-on-carbon and 40 ml of ethanol for 1 hour. At the end of this time, the atmosphere was replaced by nitrogen, the palladium-on-carbon was removed by filtration from the reaction mixture, and the filtrate was concentrated by evaporation under reduced pressure, to give 1.88 g of the title compound having an Rf value of 0.27 (on silica gel thin layer chromatography, using a 1:3 by volume mixture of ethyl acetate and hexane as the developing solvent).

PREPARATION 10

1-(3-Chlorophenoxymethyl)-2-(2-t-butyldimethylsilyloxy-1-methylethylamino)ethanol.

A mixture of 1.48 g of 2-t-butyldimethylsilyloxy-1-methylethylamine (prepared as described in Preparation 9), 1.44 g of 3-chlorophenoxymethyloxirane (prepared as described in Preparation 1) and 16 ml of ethanol was heated under reflux for 24 hours. At the end of this time, the ethanol was removed from the reaction mixture by evaporation under reduced pressure, and the resulting residue was purified by silica gel column chromatography, using a gradient elution method, with mixtures of ethyl acetate and ethanol in ratios ranging from 1:0 to 10:1 by volume as the eluent, to give 1.53 g of the title compound having an Rf value of 0.30 (on silica gel thin layer chromatography, using a 10:1 by volume mixture of ethyl acetate and ethanol as the developing solvent).

PREPARATION 11

3-(2-t-Butyldimethylsilyloxy-1-methyletyl)-5-(3-cholorophenoxymethyl)-oxazolidin-2-one 146 mg of N,N'-carbonyldiimidazole were added to a solution of 300 mg of 1-(3-chlorophenoxymethyl)-2-(2-t-butyldimethylsilyloxy-1-methylethylamino)ethanol (prepared as described in Preparation 10) in 5 ml of dimethylformamide, and then the mixture was stirred at room temperature overnight. At the end of this time, the reaction mixture was purified by silica gel column chromatography, using a 1:4 by volume mixture of ethyl acetate and hexane as the eluent, to give 287 mg of the title compound (a mixture of diastereomers) having Rf values of 0.30 and 0.17 (on silica gel thin layer chromatography, using a 1:3 by volume mixture of ethyl acetate and hexane as the developing solvent).

PREPARATION 12

3-3-Chlorophenoxy-2-hydroxypropylazide 0.65 g of sodium azide and 3 ml of methyl formate were added to 12 ml of a solution of 0.37 g of 3-chlorophenoxymethyloxirane (prepared as described in Preparation 1) in an 8:1 by volume mixture of methanol and water, after which the mixture was stirred whilst heating at 50° C. for 9 hours. At the end of this time, the solvent was removed from the reaction mixture by evaporation under reduced pressure, and water was added to the resulting residue, which was then extracted with ethyl acetate. The extract was dried over anhydrous sodium sulfate, and then the solvent was removed from the extract by evaporation under reduced pressure, to give 0.40 g of the title compound as a colorless oil having an Rf value of 0.19 (on silica gel thin layer chromatography, using a 1:4 by volume mixture of ethyl acetate and hexane as the developing solvent).

PREPARATION 13

3-(3-Chlorophenoxy)-2-hydroxypropylamine 0.19 g of lithium aluminum hydride was gradually added, whilst ice-cooling and under a stream of nitrogen gas, to a solution of 0.39 g of 3-(3-chlorophenoxy)-2-hydroxypropylazide (prepared as described in Preparation 12) in 5 ml of anhydrous tetrahydrofuran. The mixture was then stirred for a further 1.5 hours under the same conditions, after which excess lithium aluminum hydride was decomposed by adding water. Insolubles were then removed by filtration from the reaction mixture, using a Celite (trade name) filter aid, and the filtrate was dried over anhydrous sodium sulfate. The solvent was then removed from the reaction mixture by evaporation under reduced pressure, to give 0.15 g of the title compound as white crystals, melting at 55° C. to 58° C.

PREPARATION 14

3-Phenoxy-2-hydroxypropylazide

A procedure similar to that described in Preparation 12 was repeated, except that 1.00 g of phenoxymethyloxirane, 1.94 g of sodium azide, 10 ml of methyl formate and 45 ml of an 8:1 by volume mixture of methanol and water were used, to give 1.30 g of the title compound as a pale yellow oil having an Rf value of 0.26 (on silica gel thin gel thin layer chromatography, using a 1:4 by volume mixture of ethyl acetate and hexane as the developing solvent).

PREPARATION 15

3-Phenoxy-2-hydroxypropylamine

A procedure similar to that described in Preparation 13 was repeated, except that 1.17 g of 3-phenoxy-2-hydroxypropylazide (prepared as described in Preparation 14), 0.46 g of lithium aluminum hydride and 20 ml of anhydrous tetrahydrofuran were used, to give 1.09 g of the title compound, melting at 82° C. to 84° C.

PREPARATION 16

3-Phenyl-2-hydroxypropylazide

A procedure similar to that described in Preparation 12 was repeated, except that 5 g of (±)-(2,3-epoxypropyl) benzene, 12.1 g of sodium azide, 60 ml of methyl formate and 270 ml of an 8:1 by volume mixture of methanol and water were used, to give 6.03 g of the title compound as a colorless oil having an Rf value of 0.3 (on silica gel thin layer chromatography, using a 1:4 by volume mixture of ethyl acetate and hexane as the developing solvent).

PREPARATION 17

3-Phenyl-2-hydropropylamine

A procedure similar to that described in Preparation 13 was repeated, except that 6.0 g of 3-phenyl-2-hydroxypropylazide (prepared as described in Preparation 16), 2.6 g of lithium aluminum hydride and 300 ml of anhydrous tetrahydrofuran were used, to give 5.26 g of the title compound, melting at 64° C. to 66° C.

PREPARATION 18

5-[4-(2-Oxopropylthio)benzyl]thiazolidine-2,4-dione 1.28 g of sodium hydride (as a 55% by weight dispersion in mineral oil) were washed with toluene, and then 30 ml of dimethylformamide were added. A solution of 3.2 g of 5-(4-mercaptobenzyl)thiazolidine-2,4-dione in 20 ml of dimethylformamide was then added dropwise to the mixture, whilst ice-cooling, and the resulting mixture was stirred at room temperature for 30 minutes. At the end of this time, 1.69 ml of bromoacetone were added to the reaction mixture, whilst ice-cooling, and the mixture was stirred at room temperature for 2 hours. The reaction mixture was then left to stand overnight, after which the dimethylformamide was removed by evaporation under reduced pressure. Water was added to the resulting residue, and the mixture was adjusted to a pH value within the range from 2 to 3 by the addition of 1N aqueous hydrochloric acid and then extracted with ethyl acetate. The extract was washed with a saturated aqueous solution of sodium chloride and dried over anhydrous sodium sulfate. The ethyl acetate was removed from the extract by evaporation under reduced pressure, and the resulting residue was purified by silica gel column chromatography, using a 2:3 by volume mixture of ethyl acetate and hexane as the eluent, to give 1.68 g of the title compound, melting at 96° C. to 102° C.

PREPARATION 19

5-[4-(2,2-diethoxyethoxy)benzyl]thiazolidine-2,4-dione 260 mg of sodium hydride (as a 55% by weight dispersion in mineral oil) was washed with toluene, and then 5 ml of dimethylformamide were added. 530 mg of 5-(4-hydroxybenzyl)thiazolidine-2,4-dione were added to the resulting mixture, whilst ice-cooling, and the mixture was then stirred at room temperature for 30 minutes. At the end of this time, 0.73 ml of bromoacetaldehyde diethyl acetal was added to the reaction mixture, whilst ice-cooling, and the mixture was stirred at 50° C. for 3 hours. The dimethylformamide was then removed by evaporation under reduced pressure. Water was added to the resulting residue, and the mixture was adjusted to a pH within the range of from 2 to 3 by the addition of 1N aqueous hydrochloric acid and then extracted with ethyl acetate. The extract was washed with a saturated aqueous solution of sodium chloride and dried over anhydrous sodium sulfate. The ethyl acetate was removed from the extract by evaporation under reduced pressure, and the resulting residue was purified by silica gel column chromatography, using a 1:2 by volume mixture of ethyl acetate and hexane as the eluent, to give 600 mg of the title compound having an Rf value of 0.46 (on silica gel thin layer chromatography, using a 1:2 by volume mixture of ethyl acetate and hexane as the developing solvent).

PREPARATION 20

5-[4-(2-Oxoethoxy)benzyl]thiazolidine-2,4-dione 10.07 g of 5-[4-(2,2-diethoxyethoxy)benzyl]-thiazolidine- 2,4-dione (prepared as described in Preparation 19) were dissolved in 80 ml of tetrahydrofuran, and then 20 ml of 6N aqueous hydrochloric acid were added to the resulting solution. The mixture was then left to stand at room temperature overnight. At the end of this time, the solvent was removed from the reaction mixture by evaporation under reduced pressure, and water was added to the resulting residue, which was then extracted with ethyl acetate. The extract was dried over anhydrous sodium sulfate. The ethyl acetate was removed from the extract by evaporation under reduced pressure, and the resulting residue was purified by silica gel column chromatography, using a 3:2 by volume mixture of ethyl acetate and hexane as the eluent, to give 5.92 g of the title compound having an Rf value of 0.37 (on silica gel thin layer chromatography, using a 2:1 by volume mixture of ethyl acetate and hexane as the developing solvent).

PREPARATION 21

2-[5-(3-Chlorophenoxymethyl)-2-oxooxazolidin-3-yl]-propanol 1.2 ml of a 1.0M solution of tetrabutyl ammonium fluoride in tetrahydrofuran were added dropwise to a solution of 152 mg of 3-(2-t-butyldimethylsilyloxy-1-methylethyl)-5-(3-chlorophenoxymethyl)oxazolidin-2-one (prepared as described in Preparation 11) in 1 ml of tetrahydrofuran, whilst ice-cooling. The mixture was then stirred at room temperature for 1.5 hours. At the end of this time, water and sodium chloride were added to the reaction mixture, and the mixture was extracted with ethyl acetate. The extract was dried over anhydrous sodium sulfate, and then the ethyl acetate was removed from the extract by evaporation under reduced pressure. The resulting residue was purified by silica gel column chromatography, using a gradient elution method, with mixtures of ethyl acetate and ethanol in ratios ranging from 1:0 to 20:1 by volume as the eluent, to give 97 mg of the title compound having an Rf value of 0.28 (on silica gel thin layer chromatography, using ethyl acetate as the developing solvent).

PREPARATION 22

(S)-3-Chlorophenoexymethyloxirane 5.22 g of diethyl azodicarboxylate were added dropwise to a mixture of 2.57 g of 3-chlorophenol, 7.86 g of triphenylphosphine and 30 ml of anhydrous benzene, and the mixture was stirred at room temperature for 1 hour. 2.01 g of (E)-glycidol were then added dropwise to the mixture, and the resulting mixture was left to stand at room temperature for 14 hours. At the end of this time, benzene was removed from the reaction mixture by evaporation under reduced pressure, and the resulting residue was purified by silica gel column chromatography, using a 1:3 by volume mixture of ethyl acetate and hexane as the eluent, to give 3.11 g of the title compound having an Rf value of 0.42 (on silica gel thin layer chromatography, using a 1:3 by volume mixture of ethyl acetate and hexane as the developing solvent).

PREPARATION 23

(R)-2-Benzyloxycarbonylaminopropanol 11.42 g of benzyloxycarbonyl chloride were added dropwise to a mixture of 5.00 g of D-alaninol, 18.49 g of potassium carbonate, 15 ml of ethyl acetate and 15 ml of water, and the mixture was stirred at room temperature for 1.5 hours. At the end of this time, the ethyl acetate layer was separated, and the aqueous layer was extracted with ethyl acetate. The ethyl acetate layer and the extract were combined, dried over anhydrous sodium sulfate and then concentrated by evaporation under reduced pressure. The crude crystals which precipitated were collected by filtration and washed with hexane, to give 13.68 g of the title compound, melting at 78° C. to 80° C.

PREPARATION 24

Benzyl N-[2-t-Butyldimethylsilyloxy-1(R)-methylethyl]-carbamate

A procedure similar to that described in Preparation 8 was repeated, except that 12.54 g of (R)-2-benzyloxycarbonylaminopropanol (prepared as described in Preparation 23), 9.97 g of t-butyldimethylsilyl chloride, 4.90 g of imidazole and 150 ml of anhydrous dimethylformamide were used, to give 16.43 g of the title compound having an Rf value of 0.54 (on silica gel thin layer chromatography, using a 1:4 by volume mixture of ethyl acetate and hexane as the developing solvent).

PREPARATION 25

2-t-Butyldimethylsilyloxy-1(R)-methylethylamine

A procedure similar to that described in Preparation 9 was repeated, except that 16.4 g of benzyl N-[2-t-butyldimethylsilyloxy-1(R)-methylethyl]carbamate (prepared as described in Preparation 24), 3.5 g of 10% w/w palladium-on-carbon and 100 ml of ethanol were used, to give 8.55 g of the title compound having an Rf value of 0.27 (on silica gel thin layer chromatography, using a 1:3 by volume mixture of ethyl acetate and hexane as the developing solvent) and having $[\alpha]_D=-10.1°$ (methanol, c=1.155).

PREPARATION 26

1(S)-(3-Chlorophenoxymethyl)-2-(2-t-butyldimethylsilyloxy-1(R)-methylethylamino)ethanol A procedure similar to that described in Preparation 10 was repeated, except that 1.48 g of 2-t-butyldimethylsilyloxy-1(R)-methylethylamine (prepared as described in Preparation 25), 0.72 g of (S)-3-chlorophenoxymethyloxirane (prepared as described in Preparation 22) and 10 ml of absolute ethanol were used, to give 1.00 g of the title compound having an Rf value of 0.24 (on silica gel thin layer chromatography, using ethyl acetate as the developing solvent) and having $[\alpha]_D=-14.3°$ (methanol, c=1.025).

PREPARATION 27

3-[2-Butyldimethylsilyloxy-1(R)-methylethyl]-5(S)-(3-chlorophenoxymethyl)oxazolidin-2-one A procedure similar to that described in Preparation 11 was repeated, except that 0.92 g of 1(S)-(3-chlorophenoxymethyl)-2-[2-t-butyldimethylsilyloxy-1(R)-methylethylamino]ethanol (prepared as described in Preparation 26), 0.48 g of N,N'-carbonyldiimidazole and 10 ml of anhydrous dimethylformamide were used, to give 0.92 g of the title compound having an Rf value of 0.25 (on silica gel thin layer chromatography, using a 1:2 by volume mixture of ethyl acetate and hexane as the developing solvent) and having $[\alpha]_D=+34.1°$ (methanol, c=0.960).

PREPARATION 28

2(R)-[5-(3-Chlorophenoxymethyl-2-oxooxazolidin-3-yl]propanol

A procedure similar to that described in Preparation 5 was repeated, except that 0.88 g of 3-(2-t-butyldimethylsilyloxy-1(R)-methylethyl)-5(S)-(3-chlorophenoxymethyl)oxazolidin-2-one (prepared as described in Preparation 27), 6.6 ml of tetrabutylammonium fluoride (26% w/v in tetrahydrofuran) and 10 ml of anhydrous tetrahydrofuran were used, to give 0.58 g of the title compound having an Rf value of 0.45 (on silica gel thin layer chromatography, using ethyl acetate as the developing solvent) and having $[\alpha]_D=+45.6°$ (methanol, c=1.000).

PREPARATION 29

5-{4-[2(R)-(5(S)-(3-Chlorophenoxymethyl)-2-oxooxazolidin-3-yl)propoxy]benzyl}-3-triphenylmethylthiazolidine-2,4-dione A procedure similar to that described in Preparation 6 was repeated, except that 0.52 g of 2(R)-[5(S)-(3-chlorophenoxymethyl)-2-oxooxazolidin-3-yl]propanol (prepared as described in Preparation 28), 1.01 g of 5-(4-hydroxybenzyl)-3-triphenylmethylthiazolidine-2,4-dione, 0.44 g of tributylphosphine, 0.55 g of azodicarbonyldipiperidine and 30 ml of anhydrous benzene were used, to give 1.02 g of the title compound having an Rf value of 0.26 (on silica gel thin layer chromatography, using a 1:1 by volume mixture of ethyl acetate and hexane as the developing solvent) and having $[\alpha]_D=+35.9°$ (methanol, c=1.000).

PREPARATION 30

(R)-3-Chlorophenoxymethyloxirane

A procedure similar to that described in Preparation 22 was repeated, except that 5.14 g of 3-chlorophenol, 4.44 g of (S)-glycidol, 15.72 g of triphenylphosphine, 10.44 g of diethyl azodicarboxylate and 50 ml of anhydrous benzene were used, to give 6.43 g of the title compound having an Rf value of 0.42 (on silica gel thin layer chromatography, using a 1:3 by volume mixture of ethyl acetate and hexane as the developing solvent).

PREPARATION 31

(S)-2-Benzyloxycarbonylaminopropanol

A procedure similar to that described in Preparation 7 was repeated, except that 14.55 g of L-alaninol, 126 ml of a 30–35% w/v solution of benzyloxycarbonyl chloride in toluene, 29.6 ml of triethylamine and 100 ml of anhydrous tetrahydrofuran were used, to give 8.15 g of the title compound, melting at 79° C. to 80° C.

PREPARATION 32

Benzyl N-[2-t-Butyldimethylsilyloxy-1 (S)-methylethyl]carbamate

A procedure similar to that described in Preparation 8 was repeated, except that 7.00 g of (S)-2-benzyloxycarbonylaminopropanol (prepared as described in Preparation 31), 6.03 g of t-butyldimethylsilyl chloride, 5.45 g of imidazole and 100 ml of anhydrous dimethylformamide were used, to give 10.52 g of the title compound having an Rf value of 0.48 (on silica gel thin layer chromatography, using a 1:7 by volume mixture of ethyl acetate and hexane as the developing solvent).

PREPARATION 33

2-t-Butyldimethylsilyloxy-1(S)-methylethylamine

A procedure similar to that described in Preparation 9 was repeated, except that 10.22 g of benzyl N-[2-t-butyldimethylsilyloxy-1(S)-methylethyl]carbamate (prepared as described in Preparation 32), 2.00 g of 10% w/w palladium-on-carbon and 80 ml of ethanol were used, to give 5.69 g of the title compound having an Rf value of 0.27 (on silica gel thin layer chromatography, using a 1:3 by volume mixture of ethyl acetate and hexane as the developing solvent) and having $[\alpha]_D=+9.7°$ (methanol, c=1.040).

PREPARATION 34

1(R)-(3-Chlorophenoxymethyl)-2-[2-t-butyldimethylsilyloxy-1(S)-methylethylamino]ethanol A procedure similar to that described in Preparation 10 was repeated, except that 1.51 g of 2-t-butyldimethylsilyloxy-1(S)-methylethylamine (prepared as described in Preparation 33), 0.74 g of (E)-3-chlorophenoxymethyloxirane (prepared as described in Preparation 30) and 10 ml of absolute ethanol were used, to give 0.88 g of the title compound having an Rf value of 0.24 (on silica gel thin layer chromatography, using ethyl acetate as the developing solvent) and having $[\alpha]_D=+15.1°$ (methanol, c=1.075).

PREPARATION 35

3-[2-t-Butyldimethylsilyloxy-1(S)-methylethyl]5(R)-3-chlorophenoxymethyl)oxazolidin-2-one A procedure similar to that described in Preparation 11 was repeated, except that 0.82 g of 1(R)-(3-chlorophenoxymethyl)-2-[2-t-butyldimethylsilyloxy-1(S)-methylethylamino]ethanol (prepared as described in Preparation 34), 0.43 g of N,N'-carbonyldiimidazole and 10 ml of anhydrous dimethylformamide were used, to give 0.85 g of the title compound having an Rf value of 0.25 (on silica gel thin layer chromatography, using a 1:2 by volume mixture of ethyl acetate and hexane as the developing solvent) and having [α]$_D$=−33.4° (methanol, c=1.040).

PREPARATION 36

2(S)-[5(R)-(3-Chlorophenoxymethyl)-2-oxooxazolidin-3-yl]propanol

A procedure similar to that described in Preparation 5 was repeated, except that 0.78 g of 3-[2-t-butyldimethylsilyloxy-1(S)-methylethyl]-5(R)-(3-chlorophenoxymethyl) oxazolidin-2-one (prepared as described in Preparation 35), 5.85 ml of tetrabutylammonium fluoride (26% w/v in tetrahydrofuran) and 10 ml of anhydrous tetrahydrofuran were used, to give 0.52 g of the title compound, melting at 92° C. to 94° C. and having [α]$_D$=−47.8° (methanol, c=0.980).

PREPARATION 37

5-[4-{2(S)-[5(R)-3-Chlorophenoxymethyl-2-oxooxazolidin-3yl-]propoxy}benzyl]3-triphenylmethylthiazolidine-2,4-dione A procedure similar to that described in Preparation 6 was repeated, except that 0.46 g of 2(S)-[5(R)-(3-chlorophenoxymethyl)-2-oxooxazolidin-3-yl]propanol (prepared as described in Preparation 36), 0.90 g of 5-(4-hydroxybenzyl)-3-triphenylmethylthiazolidine-2,4-dione, 0.39 g of tributylphosphine, 0.49 g of azodicarbonyldipiperidine and 30 ml of anhydrous benzene were used, to give 0.79 g of the title compound having an Rf value of 0.26 (on silica gel thin layer chromatography, using a 1:1 by volume mixture of ethyl acetate and hexane as the developing solvent) and having [α]$_D$=−35.3° (methanol, c=1.015).

PREPARATION 38

1(S)-(3-Chlorophenoxymethyl)-2-(2-t-butyldimethylsilyloxy-1(S)-methylethylamino)ethanol A procedure similar to that described in Preparation 10 was repeated, except that 2.00 g of 2-t-butyldimethylsilyloxy-1(S)-methylethylamine, 1.92 g of (S)-3-chlorophenoxymethyloxirane (prepared as described in Preparation 22) and 20 ml of ethanol were used, to give 2.22 g of the title compound having an Rf value of 0.24 (on silica gel thin layer chromatography, using ethyl acetate as the developing solvent) and having [α]$_D$=+14.7° (methanol, c=0.995).

PREPARATION 39

3-[2-t-Butyldimethylsilyloxy-1(S)-methylethyl]-5(S)-(3-chlorophenoxymethyl)oxazolidin-2-one A procedure similar to that described in Preparation 11 was repeated, except that 2.06 g of 1(S)-(3-chlorophenoxymethyl)-2-[2-t-butyldimethylsilyloxy-1(S)-methylethylamino]ethanol (prepared as described in Preparation 38), 1.07 g of N,N'-carbonyldiimidazole and 20 ml of anhydrous dimethylformamide were used, to give 2.11 g of the title compound having an Rf value of 0.18 (on silica gel thin layer chromatography, using a 1:4 by volume mixture of ethyl acetate and hexane as the developing solvent) and having [α]$_D$=+51.7° (methanol, c=1.03).

PREPARATION 40

2(S)-[5(S)-(3-Chlorophenoxymethyl)-2-oxooxazolidin-3-yl]propanol

A procedure similar to that described in Preparation 5(b) was repeated, except that 2.00 g of 3-[2-t-butyldimethylsilyloxy-1(S)-methylethyl]-5(S)-(3-chlorophenoxymethyl)oxazolidin-2-one (prepared as described in Preparation 39), 15 ml of tetrabutylammonium fluoride (26% w/v in tetrahydrofuran) and 20 ml of anhydrous tetrahydrofuran were used, to give 0.85 g of the title compound, melting at 67° C. to 70° C. and having [α]$_D$=+57.0° (methanol, c=1.055).

PREPARATION 41

5-[4-{2(S)-[5(S)-(3-Chlorophenoxymethyl)-2-oxooxazolidin-3-yl]propoxy}benzyl]-3-triphenylmethylthiazolidine-2,4-dione A procedure similar to that described in Preparation 6 was repeated, except that 405 mg of tributylphosphine, 25 ml of anhydrous benzene, 700 mg of 2(S)-[5(S)-(3-chlorophenoxymethyl)-2-oxooxazolidin-3-yl]propanol (prepared as described in Preparation 40), 505 mg of azodicarbonyldipiperidine and 745 mg of 5-(4-hydroxybenzyl)-3-triphenylmethylthiazolidine-2,4-dione were used, to give 340 mg of the title compound, melting at 80° C. to 84° C. and having [α]$_D$=+25.9° (methanol, c=0.96).

PREPARATION 42

1(R)-(3-Chlorophenoxymethyl)-2-(2-t-butyldimethylsilyloxy-1 (R)-methylethylamino)ethanol A procedure similar to that described in Preparation 10 was repeated, except that 3.00 g of 2-t-butyldimethylsilyloxy-1(R)-methylethylamine, 2.95 g of (R)-3-chlorophenoxymethyloxirane (prepared as described in Preparation 30) and 30 ml of ethanol were used, to give 3.73 g of the title compound having an Rf value of 0.23 (on silica gel thin layer chromatography, using ethyl acetate as the developing solvent) and having [α]$_D$=−15.6° (methanol, c=0.990).

PREPARATION 43

3-[2-t-Butyldimethylsilyloxy-1(R)-methyl]5(R)-(3-chlorophenoxymethyl)oxazolidin-2-one A procedure similar to that described in Preparation 11 was repeated, except that 3.45 g of 1(R)-(3-chlorophenoxymethyl)-2-(2-t-butyldimethylsilyloxy-1(R)-methylethylamino)ethanol (prepared as described in Preparation 42), 1.78 g of N,N'-carbonyldiimidazole and 30 ml of anhydrous dimethylformamide were used, to give 3.52 g of the title compound having an Rf value of 0.74 (on silica gel thin layer chromatography, using a 1:1 by volume mixture of ethyl acetate and hexane as the developing solvent) and having [α]$_D$=−53.3° (methanol, c =1.020).

PREPARATION 44

2(R)-[5(R)-3-Chlorophenoxymethyl)-2-oxooxazolidin-3yl]propanol

A procedure similar to that described in Preparation 5(b) was repeated, except that 3.25 g of 3-[2-t-butyldimethylsilyloxy-1(R)-methylethyl]-5(R)-(3-chlorophenoxymethyl)oxazolidin-2-one (prepared as described in Preparation 43), 24 ml of tetrabutylammonium fluoride (26% w/v in tetrahydrofuran) and 30 ml of anhydrous tetrahydrofuran were used, to give 2.28 g of the title compound, melting at 76° C. to 78° C. and having [α]$_D$=−65.4° (methanol, c=1.060).

PREPARATION 45

5-[4-{2(R)-[5(R)-(3-Chlorophenoxymethyl)-2-oxooxazolidin-3-yl]propoxy}benzyl]3-triphenylmethylthiazolidine-2 4-dione A procedure similar to that described in Preparation 6 was repeated, except that 526 mg of tributylphosphine, 25 ml of anhydrous benzene, 900 mg of 2(R)-[5(R)-(3-chlorophenoxymethyl)-2-oxooxazolidin-3-yl]propanol (prepared as described in Preparation 44), 656 mg of azodicarbonyldipiperidine and 1.21 g of 5-(4-hydroxybenzyl)-3-triphenylmethylthiazolidine-2,4-dione were used, to give 0.65 g of the title compound, melting at 74° C. to 81° C. and having $[\alpha]_D 29.0°$ (methanol, c=1.000).

PREPARATION 46

Benzyloxymethyloxirane 4.03 g of sodium hydride (as a 55% by weight dispersion in mineral oil) were washed with hexane, and then 200 ml of anhydrous dimethylformamide were added. 20 g of anhydrous benzyl alcohol were then added dropwise, whilst ice-cooling. The resulting mixture was stirred at room temperature for 1 hour, after which 15.2 ml of epibromohydrin were added dropwise to the reaction mixture, whilst ice-cooling. The resulting mixture was stirred for 1.5 hours and then left to stand overnight. At the end of this time, dimethylformamide was removed from the reaction mixture by evaporation under reduced pressure, water was added to the resulting residue, and the mixture was extracted with ethyl acetate. The extract was then washed with an aqueous solution of sodium chloride and dried over anhydrous sodium sulfate. The ethyl acetate was removed from the extract by evaporation under reduced pressure, and the resulting residue was purified by silica gel column chromatography, using a gradient elution method, with mixtures of ethyl acetate and hexane ranging from 1:6 to 1:5 by volume, to give 13 g of the title compound having an Rf value of 0.39 (on silica gel thin layer chromatography, using a 1:5 by volume mixture of ethyl acetate and hexane as the developing solvent).

PREPARATION 47

3-Benzyloxy-2-hydroxypropylazide

A procedure similar to that described in Preparation 12 was repeated, except that 4.92 g of benzyloxymethyloxirane (prepared as described in Preparation 46), 160 ml of an 8:1 by volume mixture of methanol and water, 9.75 g of sodium azide and 40 ml of methyl formate were used, to give 5.7 g of the title compound having an Rf value of 0.22 (on silica gel thin layer chromatography, using a 1:5 by volume mixture of ethyl acetate and hexane as the developing solvent) as a pale yellow oil.

PREPARATION 48

3-Benzyloxy-2-hydroxypropylamine

A procedure similar to that described in Preparation 13 was repeated, except that 5.7 g of 3-benzyloxy-2-hydroxypropylazide (prepared as described in Preparation 47), 2.09 g of lithium aluminum hydride and 250 ml of anhydrous tetrahydrofuran were used, to give 3.5 g of the title compound as white crystals, melting at 72° C. to 74° C.

PREPARATION 49

5-Phenylpentyloxymethyloxirane

A procedure similar to that described in Preparation 46 was repeated, except that 5 g of 5-phenyl-1-pentanol, 4.99 ml of epibromohydrin, 1.31 g of sodium hydride (as a 55% by weight dispersion in mineral oil) and 80 ml of anhydrous dimethylformamide were used. The resulting crude product was purified by silica gel column chromatography, using a 1:6 by volume mixture of ethyl acetate and hexane as the eluent, to give 4.2 g of the title compound as a colorless oil having an Rf value of 0.49 (on silica gel thin layer chromatography, using a 1:4 by volume mixture of ethyl acetate and hexane as the developing solvent).

PREPARATION 50

3-(5-Phenylpentyloxy)-2-hydroxypropylazide

A procedure similar to that described in Preparation 12 was repeated, except that 4.0 g of 5-phenylpentyloxymethyloxirane (prepared as described in Preparation 49), 5.9 g of sodium azide, 160 ml of an 8:1 by volume mixture of methanol and water and 40 ml of methyl formate were used, to give 4.5 g of the title compound as a pale yellow oil having an Rf value of 0.25 (on silica gel thin layer chromatography, using a 1:4 by volume mixture of ethyl acetate and hexane as the developing solvent).

PREPARATION 51

3-(5-Phenylpentyloxy)-2-hydroxypropylamine

A procedure similar to that described in Preparation 13 was repeated, except that 4.5 g of 3-(5-phenylpentyloxy)-2-hydroxypropylazide (prepared as described in Preparation 50), 1.3 g of lithium aluminum hydride and 250 ml of anhydrous tetrahydrofuran were used, to give 4.3 g of the title compound as a pale yellow oil having an Rf value of 0.09 (on silica gel thin layer chromatography, using a 10:2:1 by volume mixture of ethyl acetate, ethanol and triethylamine as the developing solvent).

PREPARATION 52

3-Phenylproxymethyloxirane

A procedure similar to that described in Preparation 46 was repeated, except that 8 g of 3-phenyl-1-propanol, 9.64 ml of epibromohydrin, 2.56 g of sodium hydride (as a 55% by weight dispersion in mineral oil) and 100 ml of anhydrous dimethylformamide were used. The resulting crude product was purified by silica gel column chromatography, using a 1:6 by volume mixture of ethyl acetate and hexane as the eluent, to give 7.2 g of the title compound as a colorless oil having an Rf value of 0.36 (on silica gel thin layer chromatography, using a 1:5 by volume mixture of ethyl acetate and hexane as the developing solvent).

PREPARATION 53

3-(3-Phenylpropoxy)-2-hydroxypropylazide

A procedure similar to that described in Preparation 12 was repeated, except that 5.77 g of 3-phenylpropoxymethyloxirane (prepared as described in Preparation 52), 9.75 g of sodium azide, 160 ml of an 8:1 by volume mixture of methanol and water and 40 ml of methyl formate were used, to give 6.6 g of the title compound as a pale yellow oil having an Rf value of 0.27 (on silica gel thin layer chromatography, using a 1:5 by volume mixture of ethyl acetate and hexane as the developing solvent).

PREPARATION 54

3-(3-Phenylpropoxy)-2-hydroxypropylamine

A procedure similar to that described in Preparation 13 was repeated, except that 6.5 g of 3-(3-phenylpropoxy)-2- hydroxypropylazide (prepared as described in Preparation 53), 2.1 g of lithium aluminum hydride and 250 ml of anhydrous tetrahydrofuran were used, to give 6 g of the title compound as a pale yellow oil having an Rf value of 0.09 (on silica gel thin layer chromatography, using a 10:2:1 by volume mixture of ethyl acetate, ethanol and triethylamine as the developing solvent).

PREPARATION 55

2-Phenylethoxymethyloxirane

A procedure similar to that described in Preparation 46 was repeated, except that 4.28 g of 2-phenylethanol, 1.68 g of sodium hydride (as a 55% by weight dispersion in mineral oil), 4.1 ml of epibromohydrin and 100 ml of anhydrous dimethylformamide were used. The resulting crude product was purified by silica gel column chromatography, using a 8:1 by volume mixture of hexane and ethyl acetate as the eluent, to give 4.68 g of the title compound as a colorless oil having an Rf value of 0.77 (on silica gel thin layer chromatography, using a 2:1 by volume mixture of hexane and ethyl acetate as the developing solvent).

PREPARATION 56

3-(2-Phenylethoxy)-2-hydroxypropylazide

A procedure similar to that described in Preparation 12 was repeated, except that 4.50 g of 2-phenylethoxymethyloxirane (prepared as described in Preparation 55), 8.20 g of sodium azide, 45 ml of methyl formate and 180 ml of an 8:1 by volume mixture of methanol and water were used, to give 5.49 g of the title compound as a colorless oil having an Rf value of 0.70 (on silica gel thin layer chromatography, using a 2:1 by volume mixture of hexane and ethyl acetate as the developing solvent).

PREPARATION 57

3-(2-Phenylethoxy-2-hydroxypropylamine

A procedure similar to that described in Preparation 13 was repeated, except that 5.30 g of 3-(2-phenylethoxy)-2-hydroxypropylazide (prepared as described in Preparation 56), 1.85 g of lithium aluminum hydride and 120 ml of anhydrous tetrahydrofuran were used, to give 4.47 g of the title compound as a colorless oil having an Rf value of 0.09 (on silica gel thin layer chromatography, using a 10:1 by volume mixture of ethyl acetate and methanol as the developing solvent).

PREPARATION 58

4-Phenylbutoxymethyloxirane

A procedure similar to that described in Preparation 46 was repeated, except that 5.00 g of 4-phenyl-1-butanol, 1.58 g of sodium hydride (as a 55% by weight dispersion in mineral oil), 3.9 ml of epibromohydrin and 110 ml of anhydrous dimethylformamide were used. The resulting crude product was purified by silica gel column chromatography, using an 8:1 by volume mixture of hexane and ethyl acetate as the eluent, to give 3.83 g of the title compound as a colorless oil having an Rf value of 0.77 (on silica gel thin layer chromatography, using a 2:1 by volume mixture of hexane and ethyl acetate as the developing solvent).

PREPARATION 59

3-(4-Phenylbutoxy)-2-hydroxypropylazide

A procedure similar to that described in Preparation 12 was repeated, except that 3.70 g of 4-phenylbutoxymethyloxirane (prepared as described in Preparation 58), 5.83 g of sodium azide, 37 ml of methyl formate and 135 ml of an 8:1 by volume mixture of methanol and water were used, to give 4.46 g of the title compound as a colorless oil having an Rf value of 0.67 (on silica gel thin layer chromatography, using a 2:1 by volume mixture of hexane and ethyl acetate as the developing solvent).

PREPARATION 60

3-(4-Phenylbutoxy)-2-hydroxypropylamine

A procedure similar to that described in Preparation 13 was repeated, except that 4.30 g of 3-(4-phenylbutoxy)-2-hydroxypropylazide (prepared as described in Preparation 59), 1.31 g of lithium aluminum hydride and 120 ml of anhydrous tetrahydrofuran were used, to give 3.70 g of the title compound as a colorless oil having an Rf value of 0.08 (on silica gel thin layer chromatography, using a 10:1 by volume mixture of ethyl acetate and methanol as the developing solvent).

PREPARATION 61

6-Phenylhexyloxymethyloxirane

A procedure similar to that described in Preparation 46 was repeated, except that 5 g of 6-phenyl-1-hexanol, 4.6 ml of epibromohydrin, 1.23 g of sodium hydride (as a 55% by weight dispersion in mineral oil) and 80 ml of anhydrous dimethylformamide were used. The resulting crude product was purified by silica gel column chromatography, using a 1:7 by volume mixture of ethyl acetate and hexane as the eluent, to give 4.35 g of the title compound as a colorless oil having an Rf value of 0.60 (on silica gel thin layer chromatography, using a 1:5 by volume mixture of ethyl acetate and hexane as the developing solvent).

PREPARATION 62

3-(6-Phenylhexyloxy-2-hydroxypropylazide

A procedure similar to that described in Preparation 12 was repeated, except that 4 g of 6-phenylhexyloxymethyloxirane (prepared as described in Preparation 61), 5.5 g of sodium azide, 100 ml of an 8:1 by volume mixture of methanol and water and 25 ml of methyl formate were used, to give 4.5 g of the title compound as a pale yellow oil having an Rf value of 0.39 (on silica gel thin layer chromatography, using a 1:5 by volume mixture of ethyl acetate and hexane as the developing solvent).

PREPARATION 63

3-(6-Phenylhexyloxy)-2-hydroxypropylamine

A procedure similar to that described in Preparation 13 was repeated, except that 4.5 g of 3-(6-phenylhexyloxy)-2-hydroxypropylazide (prepared as described in Preparation 62), 1.23 g of lithium aluminum hydride and 150 ml of anhydrous tetrahydrofuran were used, to give 3.14 g of the title compound as a pale yellow oil having an Rf value of 0.12 (on silica gel thin layer chromatography, using a 5:1:1 by volume mixture of ethyl acetate, ethanol and triethylamine as the developing solvent).

PREPARATION 64

8-Phenyloctyloxymethyloxirane

A procedure similar to that described in Preparation 46 was repeated, except that 4 g of 8-phenyloctyl alcohol, 3.18 ml of epibromohydrin, 0.85 g of sodium hydride (as a 55% by weight dispersion in mineral oil) and 80 ml of anhydrous dimethylformamide were used, to give 2.42 g of the title compound having an Rf value of 0.51 (on silica gel thin layer chromatography, using a 1:6 by volume mixture of ethyl acetate and hexane as the developing solvent).

PREPARATION 65

3-(8-Phenyloctyloxy)-2-hydroxypropylazide

A procedure similar to that described in Preparation 12 was repeated, except that 2.4 g of 8-phenyloctyloxymethyloxirane (prepared as described in Preparation 64), 2.97 g of sodium azide, 20 ml of methyl formate and 80 ml of an 8:1 by volume mixture of methanol and water were used, to give 2.7 g of the title compound having an Rf value of 0.29 (on silica gel thin layer chromatography, using a 1:5 by volume mixture of ethyl acetate and hexane as the developing solvent).

PREPARATION 66

3-(8-Phenyloctyloxy)-2-hydroxypropylamine

A procedure similar to that described in Preparation 13 was repeated, except that 2.6 g of 3-(8-phenyloctyloxy)-2-hydroxypropylazide (Prepared as described in Preparation 65), 0.65 g of lithium aluminum hydride and 80 ml of anhydrous tetrahydrofuran were used, to give 2.11 g of the title compound, melting at 50° C. to 54° C.

PREPARATION 67

7-Phenylheptyloxymethyloxirane

A procedure similar to that described in Preparation 46 was repeated, except that 2 g of 7-phenylheptyl alcohol, 1.7 ml of epibromohydrin, 0.44 g of sodium hydride (as a 55% by weight dispersion in mineral oil) and 50 ml of anhydrous dimethylformamide were used, to give 1.15 g of the title compound having an Rf value of 0.49 (on silica gel thin layer chromatography, using a 1:6 by volume mixture of ethyl acetate and hexane as the developing solvent).

PREPARATION 68

3-(7-Phenylheptyloxy)-2-hydroxypropylazide

A procedure similar to that described in Preparation 12 was repeated, except that 1.1 g of 7-phenylheptyloxymethyloxirane (prepared as described in Preparation 67), 1.4 g of sodium azide, 15 ml of methyl formate and 60 ml of an 8:1 by volume mixture of methanol and water were used, to give 1.27 g of the title compound having an Rf value of 0.45 (on silica gel thin layer chromatography, using a 1:3 by volume mixture of ethyl acetate and hexane as the developing solvent).

PREPARATION 69

3-(7-Phenylheptyloxy)-2-hydroxypropylamine

A procedure similar to that described in Preparation 13 was repeated, except that 1.1 g of 3-(7-phenylheptyloxy)-2-hydroxypropylazide (prepared as described in Preparation 68), 0.287 g of lithium aluminum hydride and 50 ml of anhydrous tetrahydrofuran were used, to give 0.82 g of the title compound having an Rf value of 0.12 (on silica gel thin layer chromatography, using a 5:1:1 by volume mixture of ethyl acetate, ethanol and triethylamine as the developing solvent).

PREPARATION 70

3-Fluorophenoxymethyloxirane

A procedure similar to that described in Preparation 46 was repeated, except that 4.00 g of 3-fluorophenol, 1.88 g of sodium hydride (as a 55% by weight dispersion in mineral oil), 6.66 g of epibromohydrin and 50 ml of anhydrous dimethylformamide were used, to give 5.33 g of the title compound having an Rf value of 0.48 (on silica gel thin layer chromatography, using a 1:4 by volume mixture of ethyl acetate and hexane as the developing solvent).

PREPARATION 71

1-(3-Fluorophenoxymethyl)-2-(2-t-butyldimethylsilyloxy-1-methylethylamino)ethanol A procedure similar to that described in Preparation 10 was repeated, except that 2.00 g of 2-t-butyldimethylsilyloxy-1-methylethylamine, 1.77 g of 3-fluorophenoxymethyloxirane (prepared as described in Preparation 70) and 20 ml of ethanol were used, to give 2.13 g of the title compound having an Rf value of 0.17 (on silica gel thin layer chromatography, using ethyl acetate as the developing solvent).

PREPARATION 72

3-(2-t-Butyldimethylsilyloxy-1-methylethyl)-5-(3-fluorophenoxymethyl)oxazolidin-2-one A procedure similar to that described in Preparation 11 was repeated, except that 2.00 g of 1-(3-fluorophenoxymethyl)-2-(2-t-butyldimethylsilyloxy-1-methylethylamino)ethanol (prepared as described in Preparation 71), 20 ml of anhydrous dimethylformamide and 1.09 g of N,N'-carbonyldiimidazole were used, to give 0.74 g of the title compound having an Rf value of 0.29 (on silica gel thin layer chromatography, using a 1:3 by volume mixture of ethyl acetate and hexane as the developing solvent) from a polar diastereomer and 1.03 g of the title compound, melting at 54° C. to 58° C. from a less polar diastereomer.

PREPARATION 73

2-[5-(3-Fluorophenoxymethyl)-2-oxooxazolidin-3-yl]propanol

A procedure similar to that described in Preparation 5(b) was repeated, except that 0.93 g of 3-(2-t-butyldimethylsilyloxy-1-methylethyl)-5-(3-fluorophenoxymethyl)oxazolidin-2-one (prepared as described in Preparation 72), 9 ml of anhydrous tetrahydrofuran and 7.2 ml of tetrabutylammonium fluoride (26% w/v in tetrahydrofuran) were used, to give 0.63 g of the title compound having an Rf value of 0.18 (on silica gel thin layer chromatography, using ethyl acetate as the developing solvent).

PREPARATION 74

5-{4-[2-(5-3'-Fluorophenoxymethyl-2-oxooxazolidin-3-yl)propoxy]benzyl}-3-triphenylmethylthiazolidine-2,4-dione A procedure similar to that described in Preparation 6 was repeated, except that 364 mg of tributylphosphine, 5 ml of anhydrous benzene, 698 mg of 5-(4-hydroxybenzyl)-3- triphenylmethylthiazolidine-2,4-dione, 454 mg of azodicarbonyldipiperidine and 489 mg of 2-[5-(3-fluorophenoxymethyl)-2-oxooxazolidin-3-yl]propanol (prepared as described in Preparation 73) were used, to give 0.52 g of the title compound, melting at 70° C. to 77° C.

PREPARATION 75

1-(4-Methoxyphenoxymethyl)-2-(2-t-butyldimethylsilyloxy-1-methylethylamino)ethanol A procedure similar to that described in Preparation 10 was repeated, except that 3.22 g of 2-t-butyldimethylsilyloxy-1-methylethylamine, 3.00 g of 4-methoxyphenoxymethyloxirane and 30 ml of ethanol were used, to give 3.58 g of the title compound having an Rf value of 0.15 (on silica gel thin layer chromatography, using ethyl acetate as the developing solvent).

PREPARATION 76

3-(2-t-Butyldimethylsilyloxy-1-methylethyl)-5-(4-methoxyphenoxymethyl)oxazolidin-2-one A procedure similar to that described in Preparation 11 was repeated, except that 3.36 g of 1-(4-methoxyphenoxymethyl)-2-(2-t-butyldimethylsilyloxy-1-methylethylamino)ethanol (prepared as described in Preparation 75), 1.78 g of N,N'-carbonyldiimidazole and 30 ml of anhydrous dimethylformamide were used, to give 1.42 g of the title compound having an Rf value of 0.41 (on silica gel thin layer chromatography, using a 1:2 by volume mixture of ethyl acetate and hexane as the developing solvent) from a polar diastereomer and 1.62 g of the title compound, melting at 81° C. to 85° C. from a less polar diastereomer.

PREPARATION 77

2-[5-(4-Methoxyphenoxymethyl)-2-oxooxazolidin-3-yl]propanol (a) A procedure similar to that described in Preparation 5(b) was repeated, except that 1.52 g of 3-(2-t-butyldimethylsilyloxy-1-methylethyl)-5-(4-methoxyphenoxymethyl)oxazolidin-2-one (less polar isomer), obtained as described in Preparation 76, 12 ml of tetrabutylammonium fluoride (26% w/v in tetrahydrofuran) and 10 ml of anhydrous tetrahydrofuran were used, to give 1.20 g of the title compound, melting at 80° C. to 88° C., from the less polar diastereomer.

(b) A procedure similar to that described in Preparation 5(b) was repeated, except that 1.26 g of 3-(2-t-butyldimethylsilyloxy-1-methylethyl)-5-(4-methoxyphenoxymethyl)oxazolidin-2-one (polar isomer), obtained as described in Preparation 76, 9.6 ml of tetrabutylammonium fluoride (26% w/v in tetrahydrofuran) and 10 ml of anhydrous tetrahydrofuran were used, to give 0.86 g of the title compound, melting at 62° C. to 67° C., from the polar diastereomer.

PREPARATION 78

5-{4-[2-(5-4'-Methoxyphenoxymethyl-2-oxooxazolidin-3-yl)propoxy]benzyl}-3-triphenylmethylthiazolidine-2,4-dione (a) A procedure similar to that described in Preparation 6 was repeated, except that 800 mg of 2-[5-(4-methoxyphenoxymethyl)-2-oxooxazolidin-3-yl]propanol (less polar isomer), obtained as described in Preparation 77(a), 688 mg of tributylphosphine, 30 ml of anhydrous benzene, 1.30 g of 5-(4-hydroxybenzyl)-3-triphenylmethylthiazolidine-2,4-dione and 858 mg of azodicarbonyldipiperidine were used, to give 0.75 g of the title compound, melting at 60° C. to 66° C., from the less polar diastereomer.

(b) A procedure similar to that described in Preparation 6 was repeated, except that 0.85 g of 2-[5-(4-methoxyphenoxymethyl)-2-oxooxazolidin-3-yl]propanol (polar isomer), obtained as described in Preparation 77(b), 0.73 g of tributylphosphine, 50 ml of anhydrous benzene, 1.68 g of 5-(4-hydroxybenzyl)-3-triphenylmethylthiazolidine-2,4-dione and 0.91 g of azodicarbonyldipiperidine were used, to give 0.93 g of the title compound, melting at 85° C. to 94° C., from the polar diastereomer.

PREPARATION 79

3-Dimethylaminophenoxymethyloxirane

A procedure similar to that described in Preparation 46 was repeated, except that 4.00 g of 3-dimethylaminophenol, 4.5 ml of epibromohydrin, 1.53 g of sodium hydride (as a 55% by weight dispersion in mineral oil) and 50 ml of dimethylformamide were used. The resulting crude product was purified by silica gel column chromatography, using a 1:4 by volume mixture of ethyl acetate and hexane as the eluent, to give 4.18 g of the title compound having an Rf value of 0.36 (on silica gel thin layer chromatography, using a 1:4 by volume mixture of ethyl acetate and hexane as the developing solvent).

PREPARATION 80

3-(3-Dimethylaminophenoxy)-2-hydroxypropylazide

A procedure similar to that described in Preparation 12 was repeated, except that 2.0 g of 3-dimethylaminophenoxymethyloxirane (prepared as described in Preparation 79), 3.25 g of sodium azide; 20 ml of methyl formate and 90 ml of an 8:1 by volume mixture of methanol and water were used, to give 2.34 g of the title compound having an Rf value of 0.35 (on silica gel thin layer chromatography, using a 1:4 by volume mixture of ethyl acetate and hexane as the developing solvent).

PREPARATION 81

3-(3-Dimethylaminophenoxy)-2-hydroxypropylamine

A procedure similar to that described in preparation 13 was repeated, except that 2.41 g of 3-(3-dimethylaminophenoxy)-2-hydroxypropylazide (prepared as described in Preparation 80), 0.76 g of lithium aluminum hydride and 50 ml of anhydrous tetrahydrofuran were used, to give 1.80 g of the title compound having an Rf value of 0.9 (on silica gel thin layer chromatography, using a 4:1 by volume mixture of ethyl acetate and ethanol as the developing solvent).

PREPARATION 82

4-Phenylphenoxymethyloxirane

A procedure similar to that described in preparation 46 was repeated, except that 4.00 g of 4-phenylphenol, 3.97 g of epibromohydrin, 1.27 g of sodium hydride (as a 55% by weight dispersion in mineral oil) and 80 ml of anhydrous dimethylformamide were used, to give 4.43 g of the title compound, melting at 80.2° to 82.9° C.

PREPARATION 83

3-(4-Phenylphenoxy)-2-hydroxypropylazide

A procedure similar to that described in Preparation 12 was repeated, except that 3.00 g of 4-phenylphenoxymethyloxirane (prepared as described in Preparation 82), 4.23 g of sodium azide, 15 ml of methyl formate and 90 ml of an 8:1 by volume mixture of methanol and water were used, to give 3.09 g of the title compound, melting at 72.2° to 73.9° C.

PREPARATION 84

3-(4-Phenylphenoxy)-2-hydroxypropylamine

Hydrogen was introduced into a mixture of 2.94 g of 3-(4-phenylphenoxy)-2-hydroxypropylazide (prepared as described in Preparation 83), 0.3 g of 10% w/w palladium-on-carbon and 60 ml of ethanol for 3 hours. At the end of this time, insolubles were removed by filtration, and the filtrate was concentrated by evaporation under reduced pressure, to give 2.84 g of the title compound, melting at 137.7° to 146.8° C.

PREPARATION 85

Phenylthiomethyloxirane

A solution of 5.0 g of thiophenol in 30 ml of 1,4-dioxane was added dropwise at room temperature to a mixture of 6 ml of epibromohydrin, 5.45 g of sodium hydroxide and 30 ml of 1,4-dioxane, and then the mixture was stirred at room temperature for 36 hours. At the end of this time, insoluble solids were removed by filtration, the 1,4-dioxane was evaporated from the filtrate, water was added to the resulting residue, and the mixture was extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a 1:10 by volume mixture of ethyl acetate and hexane as the eluent, to give 6.78 g of the title compound as a colorless oil having an Rf value of 0.60 (on silica gel thin layer chromatography, using a 1:10 by volume mixture of ethyl acetate and hexane as the developing solvent).

PREPARATION 86

3-Phenylthio-2-hydroxypropylazide

A procedure similar to that described in Preparation 12 was repeated, except that 7.2 g of phenylthiomethyloxirane (prepared as described in Preparation 85), 14 g of sodium azide, 65 ml of methyl formate and 270 ml of an 8:1 by volume mixture of methanol and water were used, to give 8.33 g of the title compound as a colorless oil having an Rf value of 0.23 (on silica gel thin layer chromatography, using a 1:10 by volume mixture of ethyl acetate and hexane as the developing solvent).

PREPARATION 87

3-Phenylthio-2-hydroxypropylamine

A procedure similar to that described in Preparation 13 was repeated, except that 8 g of 3-phenylthio-2-hydroxypropylazide (prepared as described in Preparation 86), 2.9 g of lithium aluminum hydride and 400 ml of anhydrous tetrahydrofuran were used, to give 6.8 g of the title compound, melting at 57° C. to 61° C.

PREPARATION 88

N-Methyl-N-phenylaminomethyloxirane

A procedure similar to that described in Preparation 46 was repeated, except that 5 g of N-methylaniline, 7.65 ml of epibromohydrin, 2.44 g of sodium hydride (as a 55% by weight dispersion in mineral oil) and 100 ml of anhydrous dimethylformamide were used, to give 1.67 g of the title compound as a pale yellow oil having an Rf value of 0.33 (on silica gel thin layer chromatography, using a 1:10 by volume mixture of ethyl acetate and hexane as the developing solvent).

PREPARATION 89

3-(N-Methyl-N-phenylamino)-2-hydroxypropylazide

A procedure similar to that described in Preparation 12 was repeated, except that 1.65 g of N-methyl-N-phenylaminomethyloxirane (prepared as described in Preparation 88), 3.29 g of sodium azide, 15 ml of methyl formate and 63 ml of an 8:1 by volume mixture of methanol and water were used, to give 1.9 g of the title compound as a pale yellow oil having an Rf value of 0.09 (on silica gel thin layer chromatography, using a 1:15 by volume mixture of ethyl acetate and hexane as the developing solvent).

PREPARATION 90

3-(N-Methyl-N-phenylamino)-2-hydroxypropylamine

Hydrogen was introduced into a mixture of 1.85 g of 3-(N-methyl-N-phenylamino)-2-hydroxypropylazide (prepared as described in Preparation 89), 0.9 g of 10% w/w palladium-on-carbon and 30 ml of ethanol for 1.5 hours. At the end of this time, the atmosphere was replaced with nitrogen, the palladium-on-carbon catalyst was removed from the reaction mixture by filtration, and the filtrate was concentrated by evaporation under reduced pressure, to give 1.6 g of the title compound which decomposed at 136° C.

PREPARATION 91

3-Chlorobenzyloxymethyloxirane

A procedure similar to that described in Preparation 46 was repeated, except that 5.00 g of 3-chlorobenzyl alcohol, 1.83 g of sodium hydride (as a 55% by weight dispersion in mineral oil), 3.45 ml of epibromohydrin and 60 ml of anhydrous dimethylformamide were used, to give 5.45 g of the title compound having an Rf value of 0.31 (on silica gel thin layer chromatography, using a 1:6 by volume mixture of ethyl acetate and hexane as the developing solvent).

PREPARATION 92

3-(3-Chlorobenzyloxy)-2-hydroxypropylazide

A procedure similar to that described in Preparation 12 was repeated, except that 4.73 g of 3-chlorobenzyloxymethyloxirane (prepared as described in Preparation 91), 7.80 g of sodium azide, 24 ml of methyl formate, 135 ml of an 8:1 by volume mixture of methanol and water and 10 ml of water were used, to give 5.74 g of the title compound having an Rf value of 0.29 (on silica gel thin layer chromatography, using a 1:4 by volume mixture of ethyl acetate and hexane as the developing solvent).

PREPARATION 93

3-(3-Chlorobenzyloxy)-2-hydroxypropylamine

A procedure similar to that described in Preparation 13 was repeated, except that 6.22 g of 3-(3-chlorobenzyloxy)-2-hydroxypropylazide (prepared as described in Preparation 92), 1.97 g of lithium aluminum hydride and 120 ml of anhydrous tetrahydrofuran were used, to give 3.37 g of the title compound having an Rf value of 0.03 (on silica gel thin layer chromatography, using a mixture of ethyl acetate as the developing solvent).

PREPARATION 94

5-[4-(2-Oxobutoxy)benzyl]-3-triphenylmethylthiazolidin-2,4-dione

A mixture of 7.37 ml of 1-bromo-2-butanone, 20.0 g of 5-(4-hydroxybenzyl)-3-triphenylmethylthiazolidine-2,4-dione, 21.18 g of cesium carbonate and 200 ml of anhydrous acetone was stirred at room temperature for 3 hours. At the end of this time, the acetone was removed by evaporation under reduced pressure, water was added to the residue, and the mixture was extracted with ethyl acetate. The extract was washed with an aqueous solution of sodium chloride and then dried over anhydrous sodium sulfate. The ethyl acetate was removed by evaporation under reduced pressure, and the residue was recrystallized from a mixture of ethyl acetate, diethyl ether and diisopropyl ether, to give 19.36 g of the title compound, melting at 155.2° to 156.4° C.

PREPARATION 95

5-[4-(2-Oxobutoxy)benzyl]thiazolidine-2,4-dione 50 ml of trifluoroacetic acid were added to a solution of 19.3 g of 5-[4-(2-oxobutoxy)benzyl]-3-triphenylmethylthiazolidine-2,4-dione (prepared as described in Preparation 94) in 100 ml of methylene chloride, and the mixture was stirred at room temperature for 1.5 hours. At the end of this time, it was concentrated by evaporation under reduced pressure. Water was added to the residue, and the mixture was neutralized with sodium hydrogencarbonate and then extracted with ethyl acetate. The extract was washed with an aqueous solution of sodium chloride and dried over anhydrous sodium sulfate. The ethyl acetate was removed by evaporation under reduced pressure, and the resulting residue was applied to a silica gel chromatography column, and eluted, using a 1:2 by volume mixture of ethyl acetate and hexane as the eluent. It was then recrystallized from a mixture of ethyl acetate and diisopropyl ether, to give 9.55 g of the title compound, melting at 141.5° to 145.7° C.

PREPARATION 96

Ethyl 2-[5-(3-chlorophenoxymethyl)-2-oxooxazolidin-3-yl]pentanoate

A procedure similar to that described in Preparation 4 was repeated, except that 1.35 g of sodium hydride (as a 55% by weight dispersion in mineral oil), 6.00 g of 5-(3-chlorophenoxymethyl)oxazolidin-2-one, 100 ml of anhydrous dimethylformamide and 6.48 g of ethyl 2-bromovalerate were used. The resulting crude product was applied to a silica gel chromatography column, and eluted, using a 1:3 by volume mixture of ethyl acetate and hexane as the eluent, to give a polar diastereomer and a less polar diastereomer separately. From the polar diastereomer, 4.5 g of the title compound having an Rf value of 0.58 (on silica gel thin layer chromatography, using a 1:1 by volume mixture of ethyl acetate and hexane as the developing solvent) were obtained, and from the less polar diastereomer, 4.47 g of the title compound, melting at 43° C. to 49° C., were obtained.

PREPARATION 97

2-[5-(3-Chlorophenoxymethyl-2-oxooxazolidin-3-yl] pentanol (a) A procedure similar to that described in Preparation 5 was repeated, except that 4.38 g of ethyl 2-[5-(3-chlorophenoxymethyl)-2-oxooxazolidin-3-yl]-pentanoate (less polar isomer), obtained as described in Preparation 96, 40 ml of anhydrous tetrahydrofuran, 0.39 g of lithium borohydride and 0.29 g of anhydrous methanol were used, to give 2.22 g of the title compound, melting at 79° C. to 81° C., from the less polar diastereomer.

(b) A procedure similar to that described in Preparation 5 was repeated, except that 4.31 g of ethyl 2-[5-(3-chlorophenoxymethyl)-2-oxooxazolidin-3-yl]-pentanoate (polar isomer), obtained as described in Preparation 96, 40 ml of anhydrous tetrahydrofuran, 0.42 g of lithium borohydride and 0.31 g of anhydrous methanol were used, to give 2.03 g of the title compound, melting at 98° C. to 102° C., from the polar diastereomer.

PREPARATION 98

5-{4-[2-(5-3'-Chlorophenoxymethyl-2-oxooxazolidin-3-yl)pentyloxy]benzyl}-3-triphenylmethylthiazolidine-2,4-dione (a) A procedure similar to that described in Preparation 6 was repeated, except that 1.00 g of 2-[5-(3-chlorophenoxymethyl)-2-oxooxazolidin-3-yl]-pentanol (less polar isomer), obtained as described in Preparation 97(a), 1.07 g of 5-(4-hydroxybenzyl)-3-triphenylmethylthiazolidine-2,4-dione, 0.74 g of triphenylphosphine, 0.49 g of diethyl azodicarboxylate and 30 ml of anhydrous tetrahydrofuran were used, to give 1.58 g of the title compound having an Rf value of 0.6 (on silica gel thin layer chromatography, using a 1:1 by volume mixture of ethyl acetate and hexane as the developing solvent) from the less polar diastereomer.

(b) A procedure similar to that described in Preparation 6 was repeated, except that 1.00 g of 2-[5-(3-chlorophenoxymethyl)-2-oxooxazolidin-3-yl]-pentanol (polar isomer), obtained as described in Preparation 97(b), 0.88 g of 5-(4-hydroxybenzyl)-3-triphenylmethylthiazolidine-2,4-dione, 0.73 g of triphenylphosphine, 30 ml of anhydrous tetrahydrofuran and 0.49 g of diethyl azodicarboxylate were used, to give 1.22 g of the title compound having an Rf value of 0.57 (on silica gel thin layer chromatography, using a 1:1 by volume mixture of ethyl acetate and hexane as the developing solvent) from the polar diastereomer.

PREPARATION 99

Methyl 2-[5-(3-chlorophenoxymethyl)-2-oxooxazolidin-3-yl]-3-methylbutanoate

A procedure similar to that described in Preparation 4 was repeated, except that 0.92 g of sodium hydride (as a 55% by weight dispersion in mineral oil), 80 ml of anhydrous dimethylformamide, 4.10 g of 5-(3-chlorophenoxymethyl) oxazolidin-2-one and 4.16 g of methyl 2-bromoisobutyrate were used. The resulting crude product was purified by silica gel column chromatography, using a gradient elution method, with mixtures of ethyl acetate and hexane in ratios ranging from 1:3 to 1:2 by volume as the eluent, to give 1.05 g of the title compound having an Rf value of 0.39 (on silica gel thin layer chromatography, using a 1:1 by volume mixture of ethyl acetate and hexane as the developing solvent) from a polar diastereomer and 1.23 g of the title compound having an Rf value of 0.48 (on silica gel thin layer chromatography, using a 1:1 by volume mixture of ethyl acetate and hexane as the developing solvent) from a less polar diastereomer.

PREPARATION 100

2-[5-(3-Chlorophenoxymethyl)-2-oxooxazolidin-3-yl]-3-methylbutanol (a) A procedure similar to that described in Preparation 5 was repeated, except that 1.14 g of methyl 2-[5-(3-chlorophenoxymethyl)-2-oxooxazolidin-3-yl]-3-methylbutanoate (less polar isomer), obtained as described in Preparation 99, 144 mg of lithium borohydride, 12 ml of anhydrous tetrahydrofuran and 105 mg of anhydrous methanol were used, to give 1.02 g of the title compound having an Rf value of 0.26 (on silica gel thin layer chromatography, using a 1:1 mixture of ethyl acetate and hexane as the developing solvent) from the less polar diastereomer.

(b) A procedure similar to that described in Preparation 5 was repeated, except that 0.93 g of methyl 2-[5-(3-chlorophenoxymethyl)-2-oxooxazolidin-3-yl]-3-methylbutanoate (polar isomer), obtained as described in Preparation 99, 118 mg of lithium borohydride, 10 ml of anhydrous tetrahydrofuran and 87 mg of anhydrous methanol were used, to give 0.47 g of the title compound having an Rf value of 0.48 (on silica gel thin layer chromatography, using a 2:1 by volume mixture of ethyl acetate and hexane as the developing solvent) from the polar diastereomer.

PREPARATION 101

5-{4-[2-(5-3'-Chlorophenoxymethyl-2-oxooxazolidin-3-yl)-3-methylbutoxy]benzyl}-3-triphenylmethylthiazolidine-2,4-dione (a) A procedure similar to that described in Preparation 6 was repeated, except that 800 mg of 2-[5-(3-chlorophenoxymethyl)-2-oxooxazolidin-3-yl]-3-methylbutanol (less polar isomer), obtained as described in Preparation 100(a), 656 mg of triphenylphosphine, 20 ml of anhydrous tetrahydrofuran, 791 mg of 5-(4-hydroxybenzyl)-3-triphenylmethylthiazolidine-2,4-dione and 435 mg of diethyl azodicarboxylate were used, to give 0.92 g of the title compound, melting at 60° C. to 66° C., from the less polar diastereomer.

(b) A procedure similar to that described in Preparation 6 was repeated, except that 0.90 g of 2-[5-(3-chlorophenoxymethyl)-2-oxooxazolidin-3-yl]-3-methylbutanol (polar isomer), obtained as described in Preparation 100(b), 0.76 g of triphenylphosphine, 0.88 g of 5-(4-hydroxybenzyl)-3-triphenylmethylthiazolidine-2,4-dione, 20 ml of anhydrous tetrahydrofuran and 0.49 g of diethyl azodicarboxylate were used, to give 1.22 g of the title compound having an Rf value of 0.55 (on silica gel thin layer chromatography, using a 1:1 by volume mixture of ethyl acetate and hexane as the developing solvent) from the polar diastereomer.

PREPARATION 102

2-Benzyloxycarbonylamino-2-methylpropanol

A procedure similar to that described in Preparation 7 was repeated, except that 7.00 g of 2-amino-2-methylpropanol, 13.47 g of benzyloxycarbonyl chloride, 13.13 g of potassium carbonate, 35 ml of ethyl acetate and 35 ml of water were used, to give 17.59 g of the title compound having an Rf value of 0.72 (on silica gel thin layer chromatography, using a 3:1 by volume mixture of ethyl acetate and hexane as the developing solvent).

PREPARATION 103

Benzyl N-[2-t-Butyldimethylsilyloxy-1,1-dimethylethyl]-carbamate

A procedure similar to that described in Preparation 8 was repeated, except that 10.00 g of 2-benzyloxycarbonylamino-2-methylpropanol, 7.35 g of imidazole, 150 ml of anhydrous dimethylformamide and 8.14 g of t-butyldimethylsilyl chloride were used, to give 14.68 g of the title compound having an Rf value of 0.73 (on silica gel thin layer chromatography, using a 1:4 by volume mixture of ethyl acetate and hexane as the developing solvent).

PREPARATION 104

2-t-Butyldimethylsilyloxy-1,1-dimethylethylamine

A procedure similar to that described in Preparation 9 was repeated, except that 8.00 g of benzyl N-[2-t-butyldimethylsilyloxy-1,1-dimethylethyl]carbamate (prepared as described in Preparation 103), 1.60 g of 10% w/w palladium-on-carbon and 80 ml of ethanol were used, to give 4.02 g of the title compound having an Rf value of 0.14 (on silica gel thin layer chromatography, using ethyl acetate as the eluent).

PREPARATION 105

1-(3-Chlorophenoxymethyl)-2-(2-t-butyldimethylsilyloxy-1,1-dimethylethylamino) ethanol A procedure similar to that described in Preparation 10 was repeated, except that 3.36 g of 2-t-butyldimethylsilyloxy-1,1-dimethylethylamine, 3.05 g of 3-chlorophenoxymethyloxirane and 30 ml of ethanol were used, to give 4.54 g of the title compound, melting at 70.5° C. to 77.3° C.

PREPARATION 106

3-(2-t-Butyldimethylsilyloxy-1,1-dimethylethyl-5-(3-chlorophenoxymethyl)oxazolidin-2-one A procedure similar to that described in Preparation 11 was repeated, except that 5.13 g of 1-(3-chlorophenoxymethyl)-2-(2-t-butyldimethylsilyloxy-1,1-dimethylethylamino)ethanol (prepared as described in Preparation 105), 50 ml of anhydrous dimethylformamide and 2.59 g of N,N'-carbonyldiimidazole were used, to give 5.27 g of the title compound having an Rf value of 0.33 (on silica gel thin layer chromatography, using a 1:4 by volume mixture of ethyl acetate and hexane as the developing solvent).

PREPARATION 107

5-(3-Chlorophenoxymethyl)-3-(2-hydroxy-1,1-dimethylethyl)-oxazolidin-2-one 7 ml of a 5% w/v solution of hydrogen fluoride in acetonitrile were added dropwise to a solution of 3.84 g of 3-(2-t-butyldimethylsilyloxy-1,1-dimethylethyl)-5-(3-chlorophenoxymethyl)oxazolidin-2-one (prepared as described in Preparation 106) in 40 ml of acetonitrile, and then the mixture was stirred at room temperature for 1 hour. At the end of this time, the solvent was removed from the reaction mixture by evaporation under reduced pressure to give 2.71 g of the title compound, melting at 81° C. to 82° C.

PREPARATION 108

5-(3-Chlorophenoxymethyl)-3-[2-(4-nitrophenoxy)-1,1-dimethylethyl]oxazolidin-2-one A total of 35 mg of sodium hydride (as a 55% by weight dispersion in mineral oil) was added in three portions, whilst ice-cooling, to a solution of 200 mg of 5-(3-chlorophenxoymethyl)-3-(2-hydroxy-1,1-dimethylethyl)oxazolidin-2-one and 288 mg of 4-fluoronitrobenzene in 5 ml of dimethylformamide, and the mixture was stirred at the same temperature for 30 minutes. The mixture was then stirred at room temperature for 7 hours, after which the solvent was removed from the reaction mixture by evaporation under reduced pressure. Water was added to the resulting residue, and the mixture was extracted with ethyl acetate. The extract was further washed with an aqueous solution of sodium chloride and dried over anhydrous sodium sulfate. The ethyl acetate was removed from the extract by evaporation under reduced pressure, after which the resulting residue was purified by silica gel column chromatography, using a 2:3 by volume mixture of ethyl acetate and hexane as the eluent, to give 262 mg of the title compound, melting at 108° C. to 112° C.

PREPARATION 109

3-[2-(4-Aminophenoxy)-1,1-dimethylethyl]-5-(3-chlorophenoxymethyl)oxazolidin-2-one 6.32 g of stannous chloride dihydrate were added to a solution of 2.34 g of 5-(3-chlorophenoxymethyl)-3-[2-(4-nitrophenoxy)-1,1-dimethylethyl]oxazolidin-2-one (prepared as described in Preparation 108) in 70 ml of a 9:1 by volume mixture of ethyl acetate and t-butanol. 0.11 g of sodium borohydride was then added to the mixture over an oil bath at 66° C. The mixture was stirred at the same temperature for 6 hours. At the end of this time, the solvent was removed from the reaction mixture by evaporation under reduced pressure, and the residue was neutralized by adding an aqueous sodium hydrogencarbonate solution. The insolubles which had precipitated were removed by filtration, and the filtrate was extracted with ethyl acetate. The extract was washed with an aqueous solution of sodium chloride and dried over anhydrous sodium sulfate. The ethyl acetate was removed from the extract by evaporation under reduced pressure, to give 1.96 g of the title compound having an Rf value of 0.34 (on silica gel thin layer chromatography, using a 4:1 by volume mixture of ethyl acetate and hexane as the developing solvent).

PREPARATION 110

Butyl 2-bromo-3-{4-[2-(5-3'-chlorophenoxymethyl-2-oxooxazolidin-3-yl)-2-methylpropoxy]phenyl}-propionate 4.82 g of a 47% w/v aqueous solution of hydrogen bromide was added dropwise, whilst ice-cooling, to a solution of 2.20 g of 3-[2-(4-aminophenoxy)1,1-dimethylethyl]-5-(3-chlorophenoxymethyl)oxazolidin-2-one in 25 ml of acetone, and then 2 ml of an aqueous solution of 462 mg of sodium nitrite was added to the resulting mixture. The mixture was stirred at the same temperature for 15 minutes, and then 7.18 g of butyl acrylate, followed by 157 mg of copper(I) oxide, were added at room temperature. The mixture was stirred at room temperature for 2.5 hours, and then the solvent was removed from the reaction mixture by evaporation under reduced pressure. The residue was neutralized by adding an aqueous sodium hydrogencarbonate solution thereto, and the mixture was extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a gradient elution method, with mixtures of ethyl acetate and hexane in ratios ranging from 1:3 to 1:1 by volume as the eluent, to give 2.24 g of the title compound having an Rf value of 0.44 (on silica gel thin layer chromatography, using a 1:2 by volume mixture of ethyl acetate and hexane as the developing solvent).

PREPARATION 111

5-{4-[2-(5-3'-Chlorophenoxymethyl-2-oxooxazolidin-3-yl)-2-methylpropoxy]benzyl}-2-iminothiazolidin-4-one 0.5 g of thiourea was added to a solution of 2.07 g of butyl 2-bromo-3-{4-[2-(5-3'-chlorophenoxymethyl-2-oxooxazolidin-3-yl)-2-methylpropoxy]phenyl}propionate (prepared as described in Preparation 110) in 30 ml of methanol, and then 0.49 g of sodium acetate was added to the resulting mixture. The mixture was then heated under reflux for 5 hours, after which the solvent was removed from the reaction mixture by evaporation under reduced pressure. A saturated aqueous solution of sodium chloride was added to the residue, and the mixture was extracted with ethyl acetate. The extract was dried over anhydrous sodium sulfate, and the ethyl acetate was removed by evaporation under reduced pressure. The resulting residue was purified by silica gel column chromatography, using a gradient elution method, with mixtures of ethyl acetate and tetrahydrofuran in ratios ranging from 1:0 to 3:1 by volume as the eluent, to give 1.50 g of a mixture of the title compound having an Rf value of 0.19 (on silica gel thin layer chromatography, using ethyl acetate as the developing solvent) and thiourea.

PREPARATION 112

5-Phenoxymethyloxazolidin-2-one 422 mg of N,N'-carbonyldiimidazole were added, whilst ice-cooling, to a solution of 500 mg of 3-phenoxy-2-hydroxypropylamine in 5 ml of anhydrous dimethylformamide, and the mixture was stirred at room temperature overnight. At the end of this time, the solvent was removed from the reaction mixture by evaporation under reduced pressure, and water was added to the resulting concentrate. The mixture was then extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using ethyl acetate as the eluent, to give 490 mg of the title compound, melting at 110° C. to 111° C.

PREPARATION 113

Ethyl 3-(5-phenoxymethyl-2-oxooxazolidin-3-yl-propionate

A procedure similar to that described in Preparation 4 was repeated, except that 113 mg of sodium hydride (as a 55% by weight dispersion in mineral oil), 10 ml of anhydrous dimethylformamide, 420 mg of 5-phenoxymethyloxazolidin-2-one (prepared as described in Preparation 112) and 471 mg of ethyl 3-bromopropionate were used, to give 463 mg of the title compound having an Rf value of 0.34 (on silica gel thin layer chromatography, using a 2:1 by volume mixture of ethyl acetate and hexane as the developing solvent).

PREPARATION 114

3-(5-Phenoxymethyl-2-oxooxazolidin-3-yl)propanol

A procedure similar to that described in Preparation 5(a) was repeated, except that 1.64 g of ethyl 3-(5-phenoxymethyl-2-oxooxazolidin-3-yl)propionate (prepared as described in Preparation 113), 15 ml of anhydrous tetrahydrofuran, 244 mg of lithium borohydride and 179 mg of anhydrous methanol were used, to give 1.41 g of the title compound having an Rf value of 0.28 (on silica gel thin layer chromatography, using ethyl acetate as the developing solvent).

PREPARATION 115

5-{4-(3-(5-Phenoxymethyl-2-oxooxazolidin-3-yl)-propoxy]benzyl}-3-triphenylmethylthiazolidine-2,4-dione A procedure similar to that described in Preparation 6 was repeated, except that 1.29 g of tributylphosphine, 30 ml of anhydrous benzene, 2.98 g of 5-(4-hydroxybenzyl)-3-triphenylmethylthiazolidine-2,4-dione, 1.61 g of azodicar-bonyldipiperidine and 1.33 g of 3-(5-phenoxymethyl-2-oxooxazolidin-3-yl)propanol (prepared as described in Preparation 114) were used, to give 2.04 g of the title compound, melting at 70° C. to 73° C.

PREPARATION 116

Ethyl 4-[5-(3-chlorophenoxymethyl)-2-oxooxazolidin-3-yl]butyrate

A procedure similar to that described in Preparation 4 was repeated, except that 0.52 g of sodium hydride (as a 55% by weight dispersion in mineral oil), 30 ml of anhydrous dimethylformamide, 2.00 g of 5-(3-chlorophenoxymethyl)oxazolidin-2-one and 2.34 g of ethyl 4-bromobutyrate were used, to give 1.50 g of the title compound having an Rf value of 0.39 (on silica gel thin layer chromatography, using a 2:1 by volume mixture of ethyl acetate and hexane as the developing solvent).

PREPARATION 117

4-[5-(3-Chlorophenoxymethyl)-2-oxooxazolidin-3-yl]butanol

A procedure similar to that described in Preparation 5 was repeated, except that 1.43 g of ethyl 4-[5-(3-chlorophenoxymethyl)-2-oxooxazolidin-3-yl]butyrate (prepared as described in Preparation 116), 183 mg of sodium borohydride, 20 ml of anhydrous tetrahydrofuran and 135 mg of anhydrous methanol were used, to give 1.26 g of the title compound having an Rf value of 0.31 (on silica gel thin layer chromatography, using ethyl acetate as the developing solvent).

PREPARATION 118

5-{4-[4-(5-3'-Chlorophenoxymethyl-2-oxooxazolidin-3-yl)butoxy]benzyl}-3-triphenylmethylthiazolidine-2,4-dione A procedure similar to that described in Preparation 6 was repeated, except that 647 mg of tributylphosphine, 20 ml of anhydrous benzene, 1.49 g of 5-(4-hydroxybenzyl)-3-triphenylmethylthiazolidine-2,4-dione, 807 mg of azodicar-bonyldipiperidine and 800 mg of 4-[5-(3-chlorophenoxymethyl)-2-oxooxazolidin-3-yl]butanol (prepared as described in Preparation 117) were used, to give 1.49 g of the title compound, melting at 68° C. to 72° C.

PREPARATION 119

2-Chloroacetamido-1-(3-chlorophenoxymethyl)ethanol

A solution of 0.24 ml of triethylamine in 1 ml of anhydrous tetrahydrofuran was added to a solution of 300 mg of 3-(3-chlorophenoxy)-2-hydroxypropylamine in 4 ml of anhydrous tetrahydrofuran, whilst ice-cooling, and then 1 ml of a solution of 192 mg of chloroacetyl chloride in anhydrous tetrahydrofuran was added dropwise to the resulting mixture. The reaction mixture was then stirred at room temperature for 3 hours. At the end of this time, the solvent was removed from the reaction mixture by evaporation under reduced pressure, water was added to the residue, and the mixture was extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a 3:2 by volume mixture of ethyl acetate and hexane as the eluent, to give 310 mg of the title compound, melting at 74° C. to 77° C.

PREPARATION 120

Ethyl 2-[6-(3-chlorophenoxymethyl)-3-oxomorpholin-4-yl]propionate

A solution of 5.50 g of 2-chloroacetamido-1-(3-chlorophenoxymethyl)ethanol (prepared as described in Preparation 119) in 110 ml of dimethylformamide was added dropwise to a solution of 2.49 g of sodium hydride (as a 55% by weight dispersion in mineral oil) in 170 ml of dimethylformamide over an oil bath at 65° C. The reaction mixture was stirred at the same temperature for 1 hour. 5.25 g of ethyl 2-bromopropionate were then added dropwise to the reaction mixture, whilst ice-cooling, and the mixture was stirred for one day. At the end of this time, the solvent was removed from the reaction mixture by evaporation under reduced pressure, water was added to the residue, and the mixture was extracted with ethyl acetate. The extract was washed with an aqueous solution of sodium chloride and dried over anhydrous sodium sulfate. The ethyl acetate was removed from the extract by evaporation under reduced pressure, and the resulting residue was purified by silica gel column chromatography, using a gradient elution method, with mixtures of ethyl acetate and hexane in ratios ranging from 1:2 to 3:2 by volume as the eluent, to give 4.23 g of the title compound having an Rf value of 0.39 (on silica gel thin layer chromatography, using ethyl acetate as the developing solvent).

PREPARATION 121

2-[2-(3-Chlorophenoxymethyl)morpholino]propanol

A solution of 1.50 g of ethyl 2-[6-(3-chlorophenoxymethyl)-3-oxomorpholin-4-yl]propionate in 10 ml of anhydrous tetrahydrofuran was added dropwise to a suspension of 0.51 g of lithium aluminum hydride in 20 ml of anhydrous tetrahydrofuran, whilst ice-cooling. The mixture was stirred at room temperature for 2.5 hours, after which excess lithium aluminum hydride was decomposed by adding sodium sulfate decahydrate to the mixture. Insolubles were then removed from the reaction mixture by filtration with the help of a Celite (trade name) filter aid, and the solvent was removed from the filtrate by evaporation under reduced pressure, to give 0.97 g of the title compound having an Rf value of 0.19 (on silica gel thin layer chromatography, using a 3:1 by volume mixture of ethyl acetate and hexane as the developing solvent).

PREPARATION 122

5-{4-[2-(2-3'-Chlorophenoxymethylmorpholino)-propoxy]benzyl}-3-triphenylmethylthiazolidine-2,4-dione A procedure similar to that described in Preparation 6 was repeated, except that 1.21 g of triphenylphosphine, 20 ml of anhydrous tetrahydrofuran, 1.77 g of 5-(4-hydroxybenzyl)-3-triphenylmethylthiazolidine-2,4-dione, 0.81 g of diethyl azodicarboxylate and 1.32 g of 2-[2-(3-chlorophenoxymethyl)morpholino]propanol (prepared as described in Preparation 121) were used, to give 1.32 g of the title compound, melting at 48° C. to 53° C.

We claim:

1. A compound of formula (I):

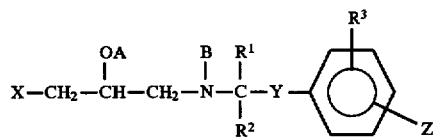

wherein:

$R^1$ and $R^2$ are the same or different and each represents a hydrogen atom or an alkyl group having from 1 to 8 carbon atoms, or $R^1$ and $R^2$ together represent a group of formula —(CH$_2$)$_k$—
wherein K represents an integer of from 2 to 6;

$R^3$ represents a hydrogen atom, an alkyl group having from 1 to 4 carbon atoms, an alkoxy group having from 1 to 4 carbon atoms, a halogen atom or a hydroxy group;

A and B are the same or different and each represents a hydrogen atom, an alkyl group having from 1 to 8 carbon atoms, an aralkyl group in which an alkyl group having from 1 to 5 carbon atoms is substituted by an aryl group as defined below, an aliphatic carboxylic acyl group having from 1 to 11 carbon atoms, an aliphatic carboxylic acyl group which has from 2 to 6 carbon atoms and which is substituted by an aryl group as defined below, an aromatic carboxylic acyl group in which the aryl part is as defined below, a carbamoyl group of formula —CONR$^6$R$^7$,
wherein R$^6$ and R$^7$ are the same or different and each represents a hydrogen atom, an alkyl group having from 1 to 11 carbon atoms, an aryl group as defined below or an aralkyl group in which an alkyl group having from 1 to 5 carbon atoms is substituted by an aryl group as defined below;

or A and B together represent a group of formula >C=O, a group of formula >C=S, a group of formula —C(=O)—C(=O)—, a group of formula —CH$_2$C(=O)—, a group of formula —CH$_2$CH$_2$—, a group of formula —SO$_2$— or a group of formula —CH$_2$SO$_2$—;

X represents a group of formula: W—(CH$_2$)$_m$—X$^1$—
wherein W represents
an aryl group as defined below, a heterocyclic group having 5 or 6 ring atoms of which from 1 to 3 are hetero-atoms selected from the group consisting of oxygen, sulfur and nitrogen hetero-atoms and being unsubstituted or being substituted by at least one substituent selected from the group consisting of substituents α as defined below or such a heterocyclic group which is fused to at least one ring system selected from the group consisting of carbocyclic and heterocyclic rings having 5 or 6 ring atoms and which is unsubstituted or is substituted by at least one substituent selected from the group consisting of substituents α as defined below, X$^1$ represents a single bond, an oxygen atom, a sulfur atom or a group of formula >NR$^4$
wherein R$^4$ represents a hydrogen atom, an alkyl group having from 1 to 8 carbon atoms, an alkyl group in which an alkyl group having from 1 to 5 carbon atoms is substituted by at least one aryl group as defined below or an aryl group as defined below, and m represents 0 or an integer of from 1 to 8;

Y represents a group of formula: —(CH$_2$)$_n$—Y$^1$—
wherein Y$^1$ represents a single bond, an oxygen atom or a sulfur atom, and n represents an integer of from 1 to 5;

Z represents a group of formula (iii) or (iv), (v) or (vi):

wherein R$^5$ represents a hydrogen atom, a carboxyalkyl group having from 2 to 5 carbon atoms, an alkanoyloxyalkyl group having a total of from 2 to 12 carbon atoms, a cycloalkyl-substituted alkanoyloxyalkyl group having a total of from 6 to 12 carbon atoms, a cycloalkylcarbonyloxyalkyl group having a total of from 5 to 17 carbon atoms, an alkoxycarbonyloxyalkyl group having a total of from 3 to 17 carbon atoms, a cycloalkyl-substituted alkoxycarbonyloxyalkyl group having a total of from 6 to 17 carbon atoms or a cycloalkyloxycarbonyloxyalkyl group having a total of from 5 to 17 carbon atoms;

said aryl groups are carbocyclic aromatic groups which have from 6 to 14 ring carbon atoms and which are unsubstituted or are substituted by at least one substituent selected from the group consisting of substituents α, defined below; and said substituents α are selected from the group consisting of alkyl groups having from 1 to 4 carbon atoms, alkoxy groups having from 1 to 4 carbon atoms, haloalkyl groups having from 1 to 4 carbon atoms, hydroxy groups, halogen atoms, phenyl groups, nitro groups and groups of formula —NR$^a$R$^b$, wherein R$^a$ and R$^b$ are independently selected from the group consisting of hydrogen atoms, alkyl groups having from 1 to 8 carbon atoms, aralkyl groups in which an alkyl group having from 1 to 5 carbon atoms is substituted by an aryl group as defined above, aryl groups as defined above, aliphatic carboxylic acyl groups having from 1 to 11 carbon atoms, aliphatic carboxylic acyl groups which have from 2 to 6 carbon atoms and which are substituted by an aryl group as defined above, and aromatic carboxylic acyl groups in which the aryl part is as defined above, provided that any aryl group represented by or included in a group represented by R$^a$ or R$^b$ is not itself further substituted by a group of formula —NR$^a$R$^b$;

or a salt or ester thereof.

2. The compound of claim 1, wherein R$^1$ and R$^2$ are the same or different and each represents a hydrogen atom or an alkyl group having from 1 to 6 carbon atoms.

3. The compound of claim 1, wherein R$^3$ represents a hydrogen atom, an alkyl group having from 1 to 4 carbon atoms, a methoxy, ethoxy or propoxy group or a halogen atom.

4. The compound of claim 1, wherein A and B are the same or different and each represents a hydrogen atom, an alkyl group having from 1 to 4 carbon atoms, an aliphatic acyl group having from 1 to 6 carbon atoms or a carbamoyl group, or A and B together form a group of formula —C(=O)—, —C(=S)—, —CH$_2$C(=O)—, —CH$_2$CH$_2$— or —S(=O) (=O)—.

5. The compound of claim 1, wherein X represents a group of formula W—(CH$_2$)$_m$—X'—, wherein W represents an aryl group which has from 6 to 10 ring carbon atoms and which is unsubstituted or is substituted by from 1 to 3 substituents selected from the group consisting of substituents α, X' represents a single bond, an oxygen atom, a sulfur atom or a group of formula —N(—R$^4$)— (in which R$^4$ represents a hydrogen atom or an alkyl group having from 1 to 4 carbon atoms) and m is 0 or an integer of from 1 to 8.

6. The compound of claim 1, wherein Z represents a group of formula (ix):

7. The compound of claim 1, wherein:

R$^1$ and R$^2$ are the same or different and each represents a hydrogen atom or an alkyl group having from 1 to 6 carbon atoms;

R$^3$ represents a hydrogen atom, an alkyl group having from 1 to 4 carbon atoms, a methoxy, ethoxy or propoxy group or a halogen atom;

A and B are the same or different and each represents a hydrogen atom, an alkyl group having from 1 to 4 carbon atoms, an aliphatic acyl group having from 1 to 6 carbon atoms or a carbamoyl group, or A and B together form a group of formula —C(=O)—, —C(=S)—, —CH$_2$C(=O)—, —CH$_2$CH$_2$— or —S(=O) (=O)—;

X represents a group of formula W—(CH$_2$)$_m$—X'—, wherein W represents an aryl group which has from 6 to 10 ring carbon atoms and which is unsubstituted or is substituted by from 1 to 3 substituents selected from the group consisting of substituents α, X' represents a single bond, an oxygen atom, a sulfur atom or a group of formula —N(—R$^4$)— (in which R$^4$ represents a hydrogen atom or an alkyl group having from 1 to 4 carbon atoms) and m is 0 or an integer of from 1 to 8;

Y is a group of formula —(CH$_2$)$_n$—Y'—, wherein Y' represents a single bond, a oxygen atom or a sulfur atom, and n is an integer of from 1 to 5; and Z represents a group of formula (ix):

8. The compound of claim 1, wherein R$^1$ and R$^2$ are the same or different and each represents a hydrogen atom or an alkyl group having from 1 to 4 carbon atoms.

9. The compound of claim 1, wherein R$^3$ represents a hydrogen atom, a methyl, ethyl, methoxy or ethoxy group or a fluorine or chlorine atom.

10. The compound of claim 1, wherein A and B are the same or different and each represents a hydrogen atom, a methyl, ethyl, propyl, acetyl, propionyl, butyryl or carbamoyl group, or A and B together form a group of formula —C(=O)—, —C(=S)—, or —CH$_2$CH$_2$—.

11. The compound of claim 1, wherein X represents a group of formula W—(CH$_2$)$_m$—X'—, wherein W represents a phenyl group which is unsubstituted or is substituted by from 1 to 3 substituents selected from the group consisting of substituents α, X' represents a single bond, an oxygen atom, a sulfur atom or a group of formula —N(—R$^4$)— (wherein R$^4$ represents a hydrogen atom, or a methyl, ethyl or propyl group) and m is 0 or an integer of from 1 to 6.

12. The compound of claim 1, wherein Y is a group of formula —(CH$_2$)$_n$—Y'—, wherein Y' represents a oxygen atom or a sulfur atom, and n is an integer of from 1 to 5.

13. The compound of claim 1, wherein R$^1$ and R$^2$ both represent hydrogen atoms, or one of them represents a hydrogen atom and the other represents an alkyl group having from 1 to 4 carbon atoms.

14. The compound of claim 1, wherein R$^3$ represents a hydrogen atom, a methyl or methoxy group or a chlorine atom.

15. The compound of claim 1, wherein A and B are the same or different and each represents a hydrogen atom, a methyl, ethyl, acetyl, propionyl or carbamoyl group, or A and B together form a group of formula —C(=O)—, —C(=S)— or —CH$_2$CH$_2$—.

16. The compound of claim 1, wherein X represents a group of formula W—(CH$_2$)$_m$—X'—, wherein w represents a phenyl group which is unsubstituted or is substituted by from 1 to 3 substituents selected from the group consisting of halogen atoms and methyl, ethyl, hydroxy, phenyl, amino, dimethylamino, methoxy and ethoxy groups, X' represents a single bond, an oxygen atom, a sulfur atom or a group of formula —NH— or —N(Me)—;

m is 0 or an integer of from 1 to 6.

17. The compound of claim 1, wherein Y represents a group of formula —(CH$_2$)$_n$—Y'—, wherein Y' represents a oxygen atom or a sulfur atom, and n is an integer of from 1 to 3.

18. The compound of claim 1, wherein R$^1$ and R$^2$ both represent hydrogen atoms or one of them represents a hydrogen atom and the other represents a methyl, ethyl, propyl or isopropyl group.

19. The compound of claim 1, wherein R$^3$ represents a hydrogen atom, a methyl group or a chlorine atom.

20. The compound of claim 1, wherein A represents a hydrogen atom and B represents a hydrogen atom, or a methyl, ethyl or acetyl group, or A and B together form a group of formula —C(=O)— or —C(=S)—.

21. The compound of claim 1, wherein X represents a group of formula W—(CH$_2$)$_m$—X'—, wherein W represents a halogen-substituted phenyl, phenylphenyl, methoxyphenyl or phenyl group, X' represents an oxygen atom or a sulfur atom;

m represents 0 or an integer of from 1 to 6.

22. The compound of claim 1, wherein Y represents a group of formula —CH$_2$O— or —(CH$_2$)$_2$—O—.

23. The compound of claim 1, wherein R$^1$ and R$^2$ both represent hydrogen atoms or one of them represents a hydrogen atom and the other represents a methyl or ethyl group.

24. The compound of claim 1, wherein R$^3$ represents a hydrogen atom.

25. The compound of claim 1, wherein A represents a hydrogen atom and B represents a hydrogen atom or a methyl group, or A and B together form a group of formula —C(=O)— or —C(=S)—.

26. The compound of claim 1, wherein X represents a group of formula W—(CH$_2$)$_m$—O—, wherein W represents a phenyl, 3-chlorophenyl, 4-chlorophenyl, 3-methoxyphenyl, 4-methoxyphenyl or 4-phenylphenyl group, and m represents 0 or an integer of from 1 to 6.

27. The compound of claim 1, wherein Y represents a group of formula —CH$_2$O—.

28. A pharmaceutical composition for the treatment or prophylaxis of diabetes or hyperlipemia, which composition comprises an effective amount of an active compound in admixture with a pharmaceutically acceptable carrier or diluent, wherein said active compound is selected from the group consisting of compounds of formula (I), as claimed in claim 1, and salts and esters thereof.

29. The composition of claim 28, wherein:

R$^1$ and R$^2$ are the same or different and each represents a hydrogen atom or an alkyl group having from 1 to 6 carbon atoms;

R$^3$ represents a hydrogen atom, an alkyl group having from 1 to 4 carbon atoms, a methoxy, ethoxy or propoxy group or a halogen atom;

A and B are the same or different and each represents a hydrogen atom, an alkyl group having from 1 to 4 carbon atoms, an aliphatic acyl group having from 1 to 6 carbon atoms or a carbamoyl group, or A and B together form a group of formula —C(=O)—, —C(=S)—, —CH$_2$C(=O)—, —CH$_2$CH$_2$— or —S(=O) (=O)—;

X represents a group of formula W—(CH$_2$)$_m$—X'—, wherein W represents an aryl group which has from 6 to 10 ring carbon atoms and which is unsubstituted or is substituted by from 1 to 3 substituents selected from the group consisting of substituents α, X' represents a single bond, an oxygen atom, a sulfur atom or a group of formula —N(—R$^4$)— (in which R$^4$ represents a hydrogen atom or an alkyl group having from 1 to 4 carbon atoms) and m is 0 or an integer of from 1 to 8;

Y is a group of formula —(CH$_2$)$_n$—Y'—, wherein Y' represents a single bond, a oxygen atom or a sulfur atom, and n is an integer of from 1 to 5; and Z represents a group of formula (ix):

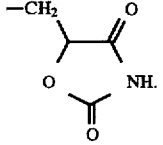

(ix)

30. A method for the treatment or prophylaxis of diabetes or hyperlipemia in a mammal, which method comprises administering to said mammal an effective amount of an active compound, wherein said active compound is selected from the group consisting of compounds of formula (I), as claimed in claim 1, and salts and esters thereof.

31. The method of claim 30, wherein:

R$^1$ and R$^2$ are the same or different and each represents a hydrogen atom or an alkyl group having from 1 to 6 carbon atoms;

R$^3$ represents a hydrogen atom, an alkyl group having from 1 to 4 carbon atoms, a methoxy, ethoxy or propoxy group or a halogen atom;

A and B are the same or different and each represents a hydrogen atom, an alkyl group having from 1 to 4 carbon atoms, an aliphatic acyl group having from 1 to 6 carbon atoms or a carbamoyl group, or A and B together form a group of formula —C(=O)—, —C(=S)—, —CH$_2$C(=O)—, —CH$_2$CH$_2$— or —S(=O) (=O)—;

X represents a group of formula W—(CH$_2$)$_m$—X'—, wherein W represents an aryl group which has from 6 to 10 ring carbon atoms and which is unsubstituted or is substituted by from 1 to 3 substituents selected from the group consisting of substituents α, X' represents a single bond, an oxygen atom, a sulfur atom or a group of formula —N(—R$^4$)— (in which R$^4$ represents a hydrogen atom or an alkyl group having from 1 to 4 carbon atoms) and m is 0 or an integer of from 1 to 8;

Y is a group of formula —(CH$_2$)$_n$—Y'—, wherein Y' represents a single bond, a oxygen atom or a sulfur atom, and n is an integer of from 1 to 5; and Z represents a group of formula (ix):

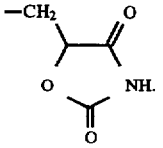

(ix)

* * * * *